US012637716B1

(12) United States Patent
Hughes et al.

(10) Patent No.: US 12,637,716 B1
(45) Date of Patent: May 26, 2026

(54) DETECTING CANCER RISK

(71) Applicant: Myriad Genetics, Inc., Salt Lake City, UT (US)

(72) Inventors: Elisha Hughes, Salt Lake City, UT (US); Alexander Gutin, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 1247 days.

(21) Appl. No.: 15/996,157

(22) Filed: Jun. 1, 2018

Related U.S. Application Data

(60) Provisional application No. 62/552,966, filed on Aug. 31, 2017, provisional application No. 62/529,259, filed on Jul. 6, 2017, provisional application No. 62/514,568, filed on Jun. 2, 2017.

(51) Int. Cl.
| | |
|---|---|
| *C12Q 1/6886* | (2018.01) |
| *C12Q 1/6827* | (2018.01) |
| *G16B 30/00* | (2019.01) |
| *G16H 50/20* | (2018.01) |
| *G16H 50/50* | (2018.01) |

(52) U.S. Cl.
CPC ......... *C12Q 1/6886* (2013.01); *C12Q 1/6827* (2013.01); *G16B 30/00* (2019.02); *G16H 50/20* (2018.01); *G16H 50/50* (2018.01); *C12Q 2600/106* (2013.01); *G01N 2800/52* (2013.01); *G01N 2800/56* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 5,310,893 | A | 5/1994 | Erlich et al. |
| 5,451,512 | A | 9/1995 | Apple et al. |
| 5,468,613 | A | 11/1995 | Erlich et al. |
| 5,593,839 | A | 1/1997 | Hubbell et al. |
| 5,604,099 | A | 2/1997 | Erlich et al. |
| 5,733,729 | A | 3/1998 | Lipshutz et al. |
| 5,744,305 | A | 4/1998 | Fodor et al. |
| 5,795,716 | A | 8/1998 | Chee |

(Continued)

FOREIGN PATENT DOCUMENTS

| | | |
|---|---|---|
| EP | 0 235 726 | 9/1987 |
| WO | WO-89/11548 | 11/1989 |

OTHER PUBLICATIONS

Susswein et al. Pathogenic and likely pathogenic variant prevalence among the first 10,000 patients referred for next-generation cancer panel testing. Genet Med 2016, published online Dec. 17, 2015, vol. 18, No. 8, pp. 823-832 (Year: 2015).*

(Continued)

*Primary Examiner* — Karlheinz R. Skowronek
*Assistant Examiner* — Mary C Leverett
(74) *Attorney, Agent, or Firm* — Foley & Lardner LLP

(57) ABSTRACT

Methods, kits, and systems for assessing the risk of a human subject for developing a cancer, including genetic risk assessment, clinical risk assessment, and combinations of both to improve risk analysis. Technologies utilize, among other things, analyzing a sample of DNA obtained or derived from a subject to detect the genotype for a plurality of test genomic loci.

26 Claims, 8 Drawing Sheets

(56) References Cited

U.S. PATENT DOCUMENTS

| 5,974,164 | A | 10/1999 | Chee |
| 6,066,454 | A | 5/2000 | Lipshutz et al. |
| 6,090,555 | A | 7/2000 | Fiekowsky et al. |
| 6,185,561 | B1 | 2/2001 | Balaban et al. |
| 6,188,783 | B1 | 2/2001 | Balaban et al. |
| 6,223,127 | B1 | 4/2001 | Berno |
| 6,229,911 | B1 | 5/2001 | Balaban et al. |
| 6,308,170 | B1 | 10/2001 | Balaban |
| 6,420,108 | B2 | 7/2002 | Mack et al. |
| 10,683,549 | B2 | 6/2020 | Allman |
| 2002/0183936 | A1 | 12/2002 | Kulp et al. |
| 2003/0097222 | A1 | 5/2003 | Craford et al. |
| 2003/0100995 | A1 | 5/2003 | Loraine et al. |
| 2003/0120432 | A1 | 6/2003 | Zhou et al. |
| 2004/0049354 | A1 | 3/2004 | Loraine et al. |
| 2015/0307947 | A1 | 10/2015 | Basu et al. |
| 2016/0222469 | A1* | 8/2016 | Allman .................. C40B 40/06 |

OTHER PUBLICATIONS

Xu et al. A fast and accurate SNP detection algorithm for next-generation sequencing data. Nature Communications 2012, 3:1258; pp. 1-9 (Year: 2012).*

Breast Cancer Care "Breast cancer in families", Jun. 2008, pp. 1-40 (Year: 2008).*

Chang et al. Review of the clinical applications and technological advances of circulating tumor DNA in cancer monitoring. Therapeutics and Clinical Risk Management, 1363-1374 (Year: 2017).*

Petric et al. Next Generation Sequencing Applications for Breast Cancer Research. Clujul Medical, vol. 88, No. 3, pp. 278-287 (Year: 2015).*

Shen et al. Clinical applications of next generation sequencing in cancer: from panels, to exomes, to genomes. vol. 6, No. 215, pp. 1-9. (Year: 2015).*

Yohe et al. Review of Clinical Next-Generation sequencing. Arch Pathol Lab Med. 141, 1544-1557 (Year: 2017).*

Abravaya et al., "Detection of point mutations with a modified ligase chain reaction", Nucleic Acids Research, vol. 23, No. 4, pp. 675-692.

Barany, "Genetic disease detection and DNA amplification using cloned thermostable ligase", PNAS, vol. 88, pp. 189-193.

Chee et al., "Accessing Genetic Information with High-Density DNA Arrays", Science, vol. 274, No. 5287, Oct. 25, 1996, pp. 610-614.

Chen et al., "Mapping translocation breakpoints by next-generation sequencing", Genome Research, vol. 18, Mar. 7, 2008, pp. 1143-1149.

Drmanac et al., "Accurate sequencing by hybridization for DNA diagnostics and individual genomics", Nature Biotechnology, vol. 16, Jan. 1998, pp. 54-58.

Drmanac et al., "DNA Sequencing Determination by Hybridization: A Strategy for Efficient Large-Scale Sequencing." Science, vol. 260, 1993, pp. 1649-1652.

Elliot et al., "Rapid Detection of the ACMG/ACOG-Recommended 23 CFTR Disease-Causing Mutations Using Ion Torrent Semiconductor Sequencing", Journal of Biomolecular Techniques, vol. 23, Issue 1, Jan. 2012, pp. 24-30.

Flusberg et al., "Direct detection of DNA methylation during single-molecule, real-time sequencing", Nature Methods, vol. 7, No. 6, Jun. 2010, pp. 461-465.

Fu et al., "Sequencing exons 5 to 8 of the p53 gene by MALDI-TOF mass spectrometry", Nature Biotechnology, vol. 16, Apr. 1998, pp. 381-384.

Kaji et al., :Nanopillar, nanoball, and nanofibers for highly efficient analysis of biomolecules, Chemical Society Reviews, vol. 39, 2010, pp. 948-956.

Kim et al., "DHPLC Analysis of Adenomatous Polyposis Coli (APC) Mutations Using Ready-to-Use APC Plates: Simple Detection of Multiple Base Pair Deletion Mutations", Genetic Testing, vol. 12, No. 12, 2008, pp. 295-298.

Landegren et al., "A Ligase-Mediated Gene Detection Technique", Science, vol. 241, No. 4869, Aug. 26, 1988, pp. 1077-1080.

Marras et al., "Multiplex detection of single-nucleotide variations using molecular beacons", Genetic Analysis: Biomolecular Engineering, vol. 14, 1999, pp. 151-156.

Maskos et al., "A novel method for the parallel analysis of multiple mutations in multiple mutations in multiple samples", Nucleic Acids Research, vol. 23, No. 9, Mar. 25, 1993, pp. 2269-2270.

Mavaddat et al., "Prediction of Breast Cancer Risk Based on Profiling With Common Genetic Variants", JNCI J Natl Cancer Inst, vol. 107, No. 5, 2015, pp. 1-15.

Michalidou et al., "Large-scale genotyping identifies 41 new loci associated with breast cancer risk", Nature Genetics, vol. 45, No. 4, Apr. 2013, pp. 353-363.

Moller et al., "The Heritability of Breast Cancer among Women in the Nordic Twin Study of Cancer", Cancer Epidemiology, Biomarkers & Prevention, vol. 25, No. 1, Jan. 2016, pp. 145-150.

Myers et al., "Detection of Single Base Substitutions by Ribonuclease Cleavage at Mismatches in RNA: DNA Duplexes", Science, vol. 230, No. 4731, Dec. 13, 1985, pp. 1242-1246.

Nikiforov et al., "Genetic Bit Analysis: a solid phase method for typing single nucleotide polymorphisms", Nucleic Acids Research, vol. 22, No. 20, Sep. 7, 1994, pp. 4167-4175.

Orita et al., "Rapid and Sensitive Detection of Point Mutations and DNA Polymorphisms Using the Polymerase Chain Reaction", Genomics, vol. 5, Aug. 1, 1989, pp. 874-879.

Piatek et al., "Molecular beacon sequence analysis for detecting drug resistance in Mycobacterium tuberculosis", Nature Biotechnology, vol. 16, Apr. 1998, pp. 359-363.

Porreca et al., "Polony DNA Sequencing" Current Protocols in Molecular Biology, Supplement 76, Chapter 7, Unit 7.8, 2006, 22 pages.

Saiki et al., "Analysis of enzymatically amplified B-globin and HLA-DQ a DNA with allele-specific oligonucleotide probes", Nature, vol. 324, Nov. 13, 1986, pp. 163-166.

Saiki et al., "Genetic analysis of amplified DNA with immobilized sequence-specific oligonucleotide probes", Proc. Natl. Acad. Sci., Aug. 1989, vol. 86, pp. 6230-6234.

Sambrook et al, "Molecular Cloning. A Laboratory Manual", 2nd ed., Cold Spring Harbor Laboratory, New York, 1989.

Schneble et al., "Current Approaches and Challenges in Early Detection of Breast Cancer Recurrence", Journal of Cancer, vol. 5, Mar. 16, 2014, pp. 281-290.

Shendure et al., "Next-generation DNA sequencing", Nature Biotechnology, vol. 26, No. 10, Oct. 2008, pp. 1135-1145.

Srivatsan et al., "High-Precision, Whole-Genome Sequencing of Laboratory Strains Facilitates Genetic Studies", PLoS Genetics, vol. 4, Issue 8, Aug. 2008, pp. 1-14.

Stoneking et al., "Population Variation of Human mtDNA Control Region Sequences Detected by Enzymatic Amplification and Sequence-specific Oligonucleotide Probes", Am. J. Hum. Genet., 1991, vol. 48, pp. 370-382.

Tapp et al., "Homogeneous Scoring of Single-Nucleotide Polymorphisms: Comparison of the 5'—Nuclease TaqMan Assay and Molecular Beacon Probes", BioTechniques, vol. 28, Apr. 2000, pp. 732-738.

Tyagi et al., "Molecular Beacons: Probes that Fluoresce upon Hybridization", Nature Biotechnology, vol. 14, Mar. 1996, pp. 303-308.

Tyagi et al., "Multicolor molecular beacons for allele discrimination", Nature Biotechnology, vol. 16, Jan. 1998, pp. 49-53.

Visvanathan et al., "American Society of Clinical Oncology Clinical Practice Guideline Update on the Use of Pharmacologic Interventions Including Tamoxifen, Raloxifene, and Aromatase Inhibition for Breast Cancer Risk Reduction", Journal Of Clinical Oncology, vol. 27, No. 19, Jul. 1, 2009, pp. 3235-3258.

Wallace et al., "Hybridization of synthetic oligodeoxyribonucleotides to 174 DNA: the effect of single base pair mismatch", Nucleic Acids Research, vol. 6, No. 11, 1978, pp. 3543-3557.

Wanunu, Meni, "Nanopores: A journey towards DNA sequencing", vol. 9, May 2012, pp. 125-158.

(56)            References Cited

OTHER PUBLICATIONS

Zimmerman et al., "Methods in Molecular and Cellular Biology", vol. 3, No. 1, 1992, pp. 39-42.

Michailidou et al., "Genome-wide association analysis of more than 120,000 individuals identifies 15 new susceptibility loci for breast cancer," Nature Genetics, 2015, 47(4):373-380, Online Methods, and Supplemental material, 81 pages.

Trujillano et al., "Next-Generation Sequencing of the BRCA1 and BRCA2 Genes for the Genetic Diagnostics of Hereditary Breast and/or Ovarian Cancer," The Journal of Molecular Diagnostics, Mar. 2015, 17(2):162-170.

Judkins et al., "Development and analytical validation of a 25-gene next generation sequencing panel that includes the BRCA1 and BRCA2 genes to assess hereditary cancer risk," BMC Cancer, 15:215, 11 pages (2015).

Campa et al., "Genetic risk variants associated with in situ breast cancer", Breast Cancer Research, 2015, vol. 17, No. 82, pp. 1-10.

Gerhardus et al. "Diagnostic accuracy of methods for the detection of BRCA 1 and BRCA2 mutations: a systematic review", European Journal of Human Genetics, 2007, vol. 15, pp. 619-627.

Kuchenbaecker et al. "Associations of common breast cancer susceptibility alleles with risk of breast cancer subtypes in BRCA 1 and BRCA2 mutation carriers", Breast Cancer Research, 2014, vol. 16, No. 3416, pp. 1-27.

Langdahl et al. "Osteoporotic Fractures Are Associated with an 86-Base Pair Repeat Polymorphism in the Interleukin- I-Receptor Antagonist Gene But Not with Polymorphisms in the Interleukin-1 f3 Gene", Journal of Bone and Mineral Research, 2000 vol. 15, No. 3, pp. 402-414.

Liang et al., "GWAS in cancer: progress and challenges", Molecular Genetics and Genomics, 2020, vol. 295, pp. 537-561.

Wall et al., "Haplotype blocks and linkage disequilibrium in the human genome", Nature Reviews Genetics, 2003, vol. 4, pp. 587-597.

* cited by examiner

DETECTING CANCER RISK

RELATED APPLICATIONS

This application claims priority to U.S. provisional application Nos. 62/514,568 (filed Jun. 2, 2017), 62/529,259 (filed Jul. 6, 2017), and 62/552,966 (filed Aug. 31, 2017), the entire contents of each of which are hereby incorporated by reference.

FIELD OF THE DISCLOSURE

The present disclosure relates to methods, kits, and systems for assessing the risk of a human subject for developing a cancer, including genetic risk assessment, clinical risk assessment, and combinations of both to improve risk analysis.

BACKGROUND OF THE DISCLOSURE

Cancer is a major public health problem, accounting for roughly 25% of all deaths in the United States. *American Cancer Society, Facts and Figures* 2010. Early detection and treatment of cancer, in particular breast cancer, can significantly improve a patient's chances of long-term survival. Schneble et al., J. CANCER (2014) 5:281-290. For breast cancer, for example, patients and clinicians have several useful tools for early detection, but some of these (e.g., MRI) can be quite costly. There is therefore a compelling need to identify patients at increased risk for disease so that limited detection resources can be focused on these patients.

As a fundamentally genetic disease, a significant proportion of cancer cases have a strong hereditary or familial basis. It has been estimated that 50% of cancer is sporadic and the other half is caused by some heritable factor(s). Moller et al., CANCER EPIDEMIOL. BIOMARKERS PREV. (2016) 25:145-145. In 5-10% of cancers, this heritable factor is a variant in a gene where pathogenic variants have been shown to be of high-to-moderate penetrance (i.e., such variants are independent drivers of a significant increase in disease risk). There is a strong need to decipher the driver(s) in the other 40-45% of cancers attributable to heredity.

BRIEF SUMMARY OF THE DISCLOSURE

The present disclosure relates to specific loci (single nucleotide polymorphisms or "SNPs") within the genome, and combinations thereof, the detection and analysis of which is useful for assessing the risk of a human subject for developing cancer. This document therefore discloses methods, kits, systems, etc. for quantifying risk for developing cancer.

Accordingly, one aspect of the present disclosure relates to a method for genotyping a subject comprising: analyzing a sample of DNA obtained or derived from the subject to detect the genotype for a plurality of genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test locus a locus in linkage disequilibrium with one or more thereof.

Another aspect of the present disclosure relates to a method for assessing risk for developing cancer comprising:
(1) analyzing a sample of DNA obtained or derived from a subject to detect the subject's genotype for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof; and
(2) determining (or estimating) the subject's risk for developing cancer based at least in part on the genotypes detected in (1).

Another aspect of the present disclosure relates to a method for assessing risk for developing cancer comprising:
(1) analyzing a sample of DNA obtained or derived from a subject to detect the subject's genotype for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;
(2) evaluating one or more clinical characteristics of the subject; and
(3) determining (or estimating) the subject's risk for developing cancer based at least in part on the genotypes detected in (1) and the clinical characteristic(s) evaluated in (2).

Another aspect of the present disclosure relates to a method for assessing risk for developing cancer comprising:
(1) analyzing a sample of DNA obtained or derived from a subject to detect the subject's genotype for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;
(2) calculating a test score incorporating the genotypes detected in (1); and
(3)(a) diagnosing a subject for whom the score in (2) exceeds a reference score as having a test likelihood of developing cancer that is higher than a reference likelihood of developing cancer; or
(3)(b) diagnosing a subject for whom the score in (2) does not exceed a reference score as having a test likelihood of developing cancer that is equal to or lower than a reference likelihood of developing cancer.

Another aspect of the present disclosure relates to a method for assessing risk for developing cancer comprising:
(1) analyzing a sample of DNA obtained or derived from a subject to detect the subject's genotype for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;
(2) evaluating one or more clinical characteristics of the subject;
(3) calculating a test score incorporating the genotypes detected in (1) and the clinical characteristic(s) evaluated in (2); and
(4)(a) diagnosing a subject for whom the score in (2) exceeds a reference score as having a test likelihood of developing cancer that is higher than a reference likelihood of developing cancer; or
(4)(b) diagnosing a subject for whom the score in (2) does not exceed a reference score as having a test likelihood of developing cancer that is equal to or lower than a reference likelihood of developing cancer.

Another aspect of the present disclosure relates to a method of screening for cancer in a subject comprising assessing the risk of the subject for developing cancer as disclosed in any aspect of the present disclosure, and screening for cancer in a subject determined to have a risk for developing breast cancer that is increased (e.g., over general population risk) or is above some threshold (e.g., greater than 15%, 20%, 25%, 30%, 35%, 40%, 50%, 60%, 70%, 80%, 90% or greater risk of developing cancer). For example, screening for breast cancer can involve screening the subject for breast cancer by mammography or MRI, performing (or administering, prescribing, or recommending) either or both of such screenings at some specific age (e.g., 30 years, 40 years, 5 or 10 years before the age of the earliest breast cancer diagnosis in the family) or predetermined interval (e.g., yearly, every two years, every three years, every four years, every five years, etc.), enrolling the subject in a screening breast MRIC and mammography program. Screening is often indicated for women with an approximately 20-25% lifetime risk of breast cancer (Saslow et al., 2007). Thus, in some embodiments, a subject with a risk (or a score corresponding to) greater than about 20% lifetime risk is screened as described above, e.g., screened for breast cancer by mammography or MRI, screened at some specific age (e.g., 30 years, 40 years, 5 or 10 years before the age of the earliest breast cancer diagnosis in the family) or predetermined interval (e.g., yearly, every two years, every three years, every four years, every five years, etc.), enrolled in a screening breast MRIC and mammography program.

Another aspect of the present disclosure relates to methods of treating subjects. This may include a method for treating a subject comprising:

(1) determining the subject's genotype for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;

(2) determining (or estimating) the subject's risk for developing cancer based at least in part on the genotypes determined in (1);

(3) prescribing or administering one or more treatment modalities indicated based at least in part on the risk determined (or estimated) in (2).

This may also include a method for preventing cancer in a subject comprising assessing the risk of the subject for developing cancer as disclosed in any aspect of the present disclosure, and administering an anti-cancer therapy (e.g., medical management that includes some action meant to prevent cancer) to a subject determined to have a risk for developing breast cancer that is increased (e.g., over general population risk) or is above some threshold (e.g., greater than 15%, 20%, 25%, 30%, 35%, 40%, 50%, 60%, 70%, 80%, 90% or greater risk of developing cancer). Pharmacological intervention is often indicated in women with a risk score greater than about 1.66% 5-year risk (Visvanathan et al., 2009). Thus, in some embodiments, a chemopreventative agent (e.g., estrogen receptor therapy, oral contraceptives, etc.) is prescribed or administered to a subject having a risk (or score corresponding to) greater than about 1.66% 5-year risk as determined herein.

This may also include an anti-breast cancer therapy for use in preventing breast cancer in a subject at risk thereof, wherein the risk of the subject for developing cancer is determined as disclosed in any aspect of the present disclosure. In some embodiments, the therapy inhibits estrogen.

Another aspect of the disclosure provides a kit for genotyping a subject comprising: a compartmentalized container; reagents for analyzing a sample of DNA obtained or derived from the subject to detect the genotype for a plurality of genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test locus a locus in linkage disequilibrium with one or more thereof; and instructions for use of the reagents.

Another aspect of the disclosure provides a system for genotyping a subject, comprising: (1) a sample analyzer for analyzing DNA in, extracted from or derived from a sample of the subject to detect the subject's genotype for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof, wherein the sample analyzer contains (a) the sample, (b) genomic DNA from the sample, (c) transcript RNA from the sample, or (d) DNA derived (e.g., synthesized or amplified) from said genomic DNA; (2) one or more computer programs for performing any one, all, or any combination of the following functions (a) a computer program for querying the subject's genotype data; (b) calculating the subject's risk for developing cancer based at least on the subject's genotype data; (c) calculating a test score based on or derived from the subject's genotype data; (d) comparing the test score to one or more reference scores; (e) concluding whether there is an increased risk of cancer based at least in part on the comparison in (d); and (f) outputting (e.g., displaying) the conclusion in (e).

Another aspect of the present disclosure provides computer program products comprising a computer-usable medium having computer-readable program codes or instructions embodied thereon for enabling a processor to carry out the methods of the disclosure. Generally speaking, the computer-usable medium comprises (1) a computer program for receiving, storing, and/or retrieving a subject's genotype data for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof; and (2) one or more computer programs for performing any one, all, or any combination of the following functions (a) a computer program for querying the subject's genotype data; (b) calculating the subject's risk for developing cancer based at least on the subject's genotype data; (c) calculating a test score based on or derived from the subject's genotype data; (d) comparing the test score to one or more reference scores; (e) concluding whether there is an increased risk of cancer based at least in part on the comparison in (d); and (f) outputting (e.g., displaying) the conclusion in (e). In some embodiments this program for outputting the conclusion may comprise a computer program for informing a health care professional of the conclusion.

Another aspect of the present disclosure relates to a computer implemented method for assessing the risk of a subject for developing cancer, the method operable in a computing system comprising a processor and a memory, the method comprising:

(1) receiving genetic risk data for the subject, wherein the genetic risk data was obtained by detecting, in a sample derived from the subject, the genotype for a plurality of test genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;

(2) optionally processing the data to combine the genetic risk data with clinical risk data to obtain the risk of the subject for developing cancer;

(3) outputting the risk of the subject for developing cancer.

In some embodiments, the clinical risk data and/or genetic risk data for the subject are received from a user interface coupled to the computing system. In some embodiments, the clinical risk data and/or genetic risk data for the subject are received from a remote device across a wireless communications network. In some embodiments, outputting comprises outputting information to a user interface coupled to the computing system. In some embodiments, outputting comprises transmitting information to a remote device across a wireless communications network.

Another aspect of the present disclosure relates to a system configured to perform the disclosed methods. This may include a system for assessing the risk of a subject for developing cancer comprising:

(a) system instructions for performing a genetic risk assessment of the subject according to any of the method aspects of the present disclosure; and (b) optionally system instructions for performing a clinical risk assessment of the subject;

(c) optionally system instructions for combining the clinical risk assessment with the genetic risk assessment to obtain the risk of a human female subject for developing breast cancer.

As will be apparent, at least some features of the methods, kits and systems can be used together in combination. For example, systems for identifying correlations between breast cancer susceptibility and polymorphisms can be used for practicing the methods herein. Kits can be used for practicing the methods herein. Thus, described features of the systems, methods and kits can be applied to the different systems, methods and kits herein.

The present disclosure includes numerous embodiments of each of the preceding aspects, including but not limited to:

(a) Embodiments further comprising assessing clinical characteristics of the subject and combining this assessment with genotyping to derive an improved assessment of cancer risk.

(b) Embodiments where the subject lacks or has been determined to not harbor a pathogenic variant in any high penetrance cancer predisposition gene.

(c) Embodiments where determining (or estimating) the subject's risk for developing cancer comprises determining (or estimating) the subject's percent probability of developing cancer within one or more specific periods of time. In some such embodiments, the period(s) of time may be the next five years; a plurality of five-, ten-, 15-, or 20-year intervals; the remainder of the subject's expected lifetime; any time before a specific age (e.g., 50, 55, 60, 65, 70, 75, 80, 85, 90 years of age); etc.

(d) Embodiments where determining (or estimating) the subject's risk for developing cancer comprises determining the subject's risk for developing cancer attributable or allocable to the detected or determined genotypes.

(e) Embodiments further comprising performing a clinical risk assessment. In some such embodiments the clinical risk assessment comprises obtaining information from the subject on one or more of the following: medical history of breast cancer, ductal carcinoma or lobular carcinoma, age, age of first menstrual period, age at which she first gave birth, family history of breast cancer, results of previous breast biopsies, breast density, and race/ethnicity.

(f) Embodiments where determining (or estimating) the subject's risk for developing cancer comprises combining the subject's risk for developing cancer attributable or allocable to the detected genotypes with a clinical risk assessment (e.g., as in (e) above) or other risk factors, calculations, scores, or estimations to yield a composite risk score or estimation. In some such embodiments the clinical risk assessment or other risk factors, calculations, scores or estimations include any of the following: a Gail Model, a Claus Model, Claus Tables, BOADICEA, a Jonker Model, a Claus Extended Formula, a Tyrer-Cuzick Model, BRCAPRO, or a Manchester Scoring System. In some such embodiments the other score or estimation is a score or risk estimation derived from a Tyrer-Cuzick Model (e.g., Tyrer-Cuzick version 7 or version 8).

(g) Embodiments where determining (or estimating) the subject's risk for developing cancer comprises calculating a test score incorporating or derived from the genotypes detected in (1). In some such embodiments, determining in (2) comprises comparing the test score to a reference score.

(h) Embodiments where risk of developing cancer is determined (or estimated) for breast cancer.

(i) Embodiments where the subject's race is Caucasian.

(j) Embodiments where, the subject has not had any previous cancer. In some embodiments the subject has not had breast cancer, lobular carcinoma or ductal carcinoma.

(k) Embodiments where a second locus is in linkage disequilibrium with a first locus in Table 1 if such second locus has linkage disequilibrium above 0.9 or 1.

(l) Embodiments where the sample is, or is derived from, a bodily fluid. In some embodiments, the sample is, or is derived from, known germline tissue (e.g., nucleated blood cells, fibroblasts, etc.).

The foregoing and other advantages and features of the disclosure, and the manner in which the same are accomplished, will become more readily apparent upon consideration of the following detailed description of the disclosure taken in conjunction with the accompanying examples and drawings.

DETAILED DESCRIPTION OF THE DISCLOSURE

Definitions

Figure 1:
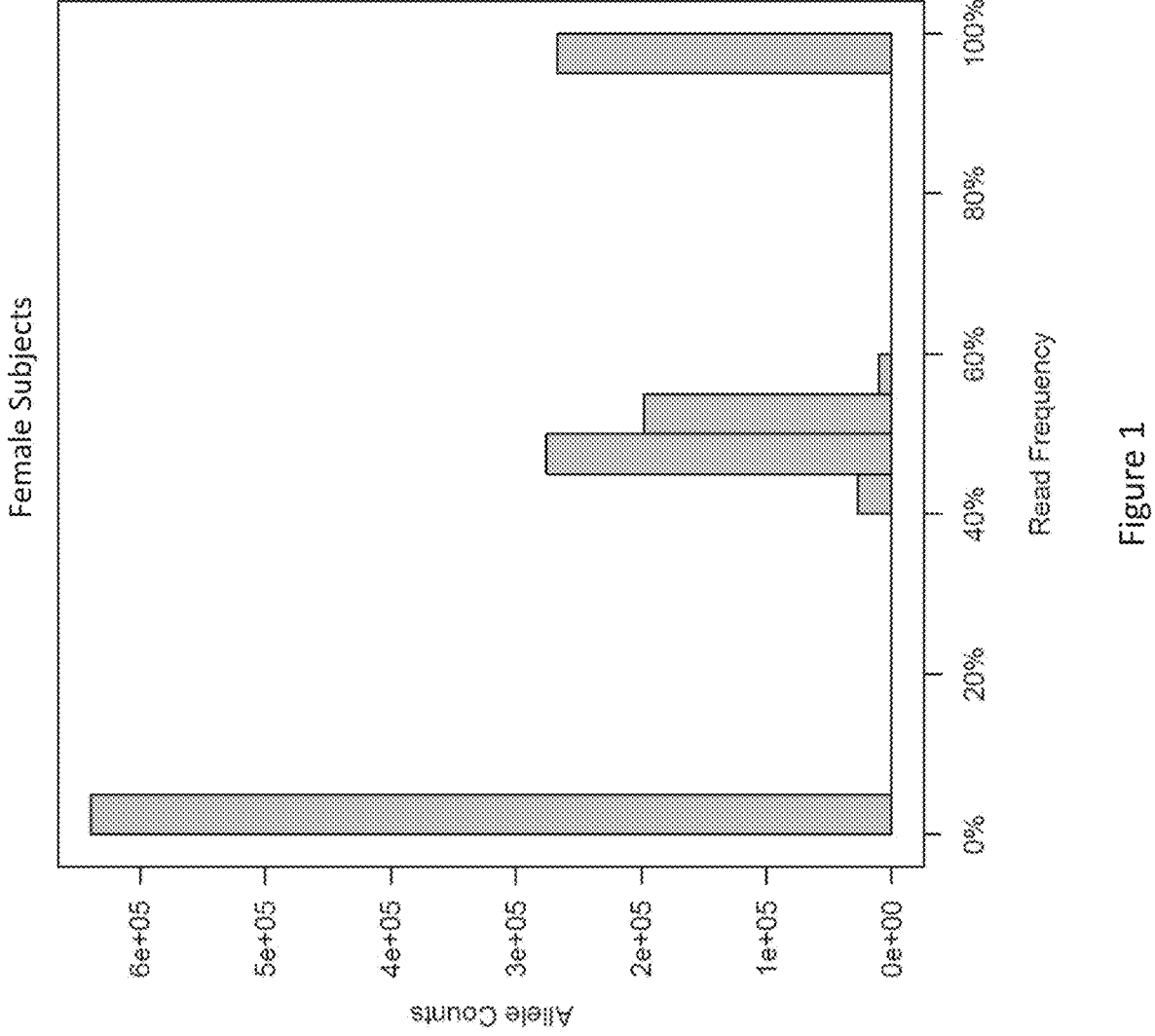
FIG. 1 shows an example of test locus (SNP) genotypes coded as the number of the effect (risk modifying) alleles detected at such test locus.

The following terms or definitions are provided solely to aid in the understanding of the disclosure. Additional definitions for other terms may be provided throughout this document. Further, terms given a general definition here in this section may be ascribed a more specific or different definition in another place of the disclosure that is applied to the indicated specific context. Unless specifically defined herein, all terms used herein have the same meaning as they would to one skilled in the art of the present disclosure. Practitioners are particularly directed to Sambrook et al., *Molecular Cloning: A Laboratory Manual, 2^{nd}* ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. Unless expressly defined otherwise herein, the terms used herein should not be construed to have a scope less than understood by a person of ordinary skill in the art.

As used herein, unless stated to the contrary, "about" means +/−10%, more preferably +/−5%, more preferably +/−1%, of the designated value.

As used herein, "algorithm" encompasses any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of mutation load as described herein are linear and non-linear equations and statistical classification analyses to determine the relationship between (a) the number of mutations detected in a subject sample and (b) the level of the respective subject's mutation load.

As used herein, "allele" means one of two or more different nucleotide sequences (DNA or RNA) that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. In the context of the genotype at a particular locus (e.g., a SNP locus), an allele generally refers to the nucleotide base present on chromosome (out of the expected two) at that specific locus. For example, at one particular SNP locus a patient may have an adenine (A) one chromosome and a guanine (G) one the other, in which case it can be said that the patient has one A allele and one G allele. As used herein, "homozygous" means an individual or subject has only one type of allele at a given locus (e.g., a diploid individual has a copy of the same allele at a locus for each of two homologous chromosomes, such as A/A in the preceding example). An individual is "heterozygous" if more than one allele type is present at a given locus (e.g., a diploid individual with one copy each of two different alleles, such as A/G in the preceding example). The term "homogeneity" indicates the degree to which members of a group have the same genotype at one or more specific loci. In contrast, the term "heterogeneity" is used to indicate the degree to which individuals within the group differ in genotype at one or more specific loci (e.g., all homozygous, all the same type of heterozygosity, etc.). An allele "positively" correlates with a trait when it is linked to it and when presence of the allele is an indicator that the trait or trait form will occur in an individual comprising the allele. An allele "negatively" correlates with a trait when it is linked to it and when presence of the allele is an indicator that a trait or trait form will not occur in an individual comprising the allele.

"Allele frequency" refers to the frequency (e.g., proportion or percentage) at which an allele (e.g., adenine versus guanine in the example above) is present at a locus within an individual, within a line or within a population (or subpopulation). In the above example, for an allele "A", diploid individuals of genotype "A/A", "A/G," or "G/G" have allele frequencies of 1.0, 0.5, or 0.0, respectively. One can estimate the allele frequency within a line or population (e.g., cases or controls) by averaging the allele frequencies of a sampling of individuals from that line or population. Similarly, one can calculate the allele frequency within a population of lines by averaging the allele frequencies of lines that make up the population. In some embodiments, the term "allele frequency" is used to define the minor allele frequency (MAF). MAF refers to the frequency at which the least common allele (where two alleles are observed) occurs in a given population, or the frequency at which the second most common allele (where more than two alleles are observed) occurs in a given population.

As used herein, "amplifying" in the context of nucleic acid amplification means any process or reaction whereby additional copies of a nucleic acid (or a transcribed form thereof) comprising a particular nucleotide sequence are produced. Amplification techniques include, but are not limited to, various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid (or population of such nucleic acids, e.g., in solution) that is (or are) produced by amplifying a template nucleic acid by an amplification technique (e.g., PCR, LCR, transcription, or the like).

As used herein, the term "analyze" or "analyzing" generally includes "measure," "measuring," "detect," "detecting," "identify," "identifying," "assay," "assaying," "quantify," or "quantifying," and refers to the process of evaluating a biological sample (or a sample derived there-from) for the presence, absence amount, level, or quality of some physical, chemical, or electromagnetic property(ies). This is often done by determining a value or set of values associated with such properties (e.g., number of sequencing reads in which a fluorescence signal indicating the presence of an adenine was observed at a particular position within the read corresponding to a particular position in a gene, chromosome or genome). Specific examples particularly relevant to the present disclosure include analyzing a sample to determining the sequence at one or more particular genomic loci in the sample, and may further comprise comparing test nucleotide sequence(s) detected in a patient's sample against reference nucleotide sequence(s) and/or comparing the test number of any such test sequences to one or more reference numbers of such reference sequences.

As used herein, "breast cancer" encompasses any type of breast cancer that can develop in a subject. For example, the breast cancer may be characterised as Luminal A (ER+ and/or PR+, HER2−, low Ki67), Luminal B (ER+ and/or PR+, HER2+ (or HER2− with high Ki67), Triple negative/basal-like (ER−, PR−, HER2−) or HER2 type (ER−, PR−, HER2+). In another example, the breast cancer may be resistant to therapy or therapies such as alkylating agents, platinum agents, taxanes, vinca agents, anti-estrogen drugs, aromatase inhibitors, ovarian suppression agents, endocrine/hormonal agents, bisphophonate therapy agents or targeted biological therapy agents.

A locus (e.g., SNP) or allele is "correlated" or "associ-ated" with a specified phenotype (e.g., increased risk of developing breast cancer) when it can be statistically linked (positively or negatively) to the phenotype. For example, a specified polymorphism may occur more commonly in a case population (e.g., breast cancer patients) than in a control population (e.g., individuals that do not have breast cancer). This correlation may suggest some natural or bio-logical causal link (e.g., a natural law or phenomenon), but it typically does not prove or require such a link (i.e., the correlation is not such a law or phenomenon per se). As used herein, "correlation" refers instead to an artificial statistical linkage between a locus and a trait that underlies the phenotype.

As used herein, the term "diagnosis" refers to methods by which a determination can be made as to whether an individual has or is likely to have a given clinical charac-teristic (e.g., risk of developing cancer). The skilled artisan often makes a diagnosis on the basis of one or more diagnostic indicators, e.g., a biomarker, the presence, absence, amount, or change in amount of which may indi-cate the presence, severity, or absence of the condition. Other diagnostic indicators can include patient history; physical symptoms, e.g., unexplained weight loss, fever, fatigue, pains, or skin anomalies; phenotype; genotype; or environmental or heredity factors. A skilled artisan will understand that the term "diagnosis" often refers to an increased probability or likelihood that given clinical char-acteristic is present or will occur; that is, that a clinical characteristic is more likely to be present or to occur in a patient exhibiting a given feature, e.g., the presence or level of a diagnostic indicator, when compared to individuals not exhibiting the feature. Diagnostic methods can be used independently, or in combination with other diagnosing methods known in the art to determine whether a clinical characteristic is present or is more likely to occur in a patient exhibiting a given feature.

As used herein, "disease" can encompass any disorder, condition, sickness, ailment, etc. that manifests in, e.g., a disordered or incorrectly functioning organ, part, structure, or system of the body, and results from, e.g., genetic or developmental errors, infection, poisons, nutritional defi-ciency or imbalance, toxicity, or unfavorable environmental factors.

As used herein, "genotype" means the genetic constitu-tion of an individual (or group of individuals) at one or more genetic loci. Genotype is defined by the allele(s) of one or more known loci of the individual, typically, the compilation of alleles inherited from its parents. In most aspects and embodiments of the present disclosure, the genotype will be the nucleotide (adenine, thymine (or uracil), cytosine, gua-nine) at a particular locus in either one or both (typically both) alleles of a subject's genome or chromosomes. With respect to a particular nucleotide position or locus, the nucleotide(s) at that locus or equivalent thereof in one or both alleles form the genotype of the locus. A genotype can typically be homozygous (e.g., A/A) or heterozygous (e.g., A/B), though more complex genotypes are possible (e.g., AA/A, AA/B, etc.). Accordingly, "genotyping" or determin-ing the genotype for a particular locus means determining the nucleotide(s) at a particular gene locus. One example of this is "detecting" the genotype at a locus, which means determining through a a physical assay the physical presence (and optionally quantity) of the nucleotides at a given locus in a patient's genome or chromosomes. Genotyping can also be done by determining the amino acid variant at a particular position of a protein which can be used to deduce the corresponding nucleotide variant(s).

As used herein, "haplotype" means the genotype of an individual at a plurality of genetic loci on a single DNA strand. Typically, the genetic loci described by a haplotype are physically and genetically linked, i.e., on the same chromosome strand.

As used herein, "high stringency hybridization condi-tions," when used in connection with nucleic acid hybrid-ization, means conditions capable of restricting hybridiza-tion between nucleic acid molecules in a reaction to only those molecules sufficiently homologous to hybridize under the following conditions: hybridization conducted overnight at 42° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 0.1×SSC at about 65° C. In some embodiments "high stringency hybrid-ization conditions" means the preceding hybridization con-ditions. The term "moderate stringent hybridization condi-tions," when used in connection with nucleic acid hybridization, means conditions capable of restricting hybridization between nucleic acid molecules in a reaction to only those molecules sufficiently homologous to hybrid-ize under the following conditions: hybridization conducted overnight at 37° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 1×SSC at about 50° C. In some embodiments "moderate stringency hybridization conditions" means the preceding hybridization conditions. It is noted that many other hybrid-ization methods, solutions and temperatures can be used to achieve comparable stringent hybridization conditions as will be apparent to skilled artisans apprised of the present disclosure.

As used herein, a patient has an "increased risk" of a particular cancer if the probability of the patient developing that cancer (e.g., over the patient's lifetime, over some defined period of time (e.g., within 10 years), etc.) exceeds some reference probability or value. The reference probability may be the probability (i.e., prevalence) of the cancer across the general relevant patient population (e.g., all patients; all patients of a particular age, gender, ethnicity; patients having a particular cancer (and thus looking at the risk of a different cancer or an independent second primary of the same type as the first cancer); etc.). For example, if the lifetime probability of a particular cancer in the general population (or some specific subpopulation) is X % and a particular patient has been determined by the methods, systems or kits of the present disclosure to have a lifetime probability of that cancer of Y %, and if Y>X, then the patient has an "increased risk" of that cancer. Alternatively, the tested patient's probability may only be considered "increased" when it exceeds the reference probability by some threshold amount (e.g., at least 0.5, 0.75, 0.85, 0.90, 0.95, 1, 2, 3, 4, 5, 6, 7, 8, 9, or 10 or more fold or standard deviations greater than the reference probability; at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, 91%, 92%, 93%, 94%, 95%, 96%, 97%, 98%, or 99% greater than the reference probability).

The phrase "linkage disequilibrium" (LD) is used to describe the statistical correlation between two polymorphic genotypes (often neighboring). Non-limiting examples of loci in LD with test loci of the present disclosure are given in Table 1. Typically, LD refers to the correlation between the alleles of a random gamete at the two loci, assuming Hardy-Weinberg equilibrium (statistical independence) between gametes. LD can be quantified with either Lewontin's parameter of association (D') or with Pearson correlation coefficient (r) (Devlin and Risch, 1995). Two loci with a LD value of 1 are generally said to be in complete LD. At the other extreme, two loci with a LD value of 0 are generally termed to be in linkage equilibrium. Linkage disequilibrium can be calculated following the application of the expectation maximization algorithm (EM) for the estimation of haplotype frequencies (Slatkin and Excoffier, 1996). LD values according to the present disclosure for genotypes/loci are selected above 0.1, above 0.2, above 0.5, above 0.6, above 0.7, above 0.8, above 0.9, or about 1.0.

Another way one of skill in the art can identify SNPs in linkage disequilibrium with SNPs of the present disclosure is determining the LOD score for two loci. LOD stands for "logarithm of the odds", a statistical estimate of whether two loci (e.g., or a locus and a disease locus) are likely to be located near each other on a chromosome and are therefore likely to be inherited together. A LOD score of between about 2-3 or higher is generally understood to suggest that two genes are located close to each other on the chromosome. In some embodiments, LOD values according to the present disclosure for genotypes/loci are selected at least above 2, at least above 3, at least above 4, at least above 5, at least above 6, at least above 7, at least above 8, at least above 9, at least above 10, at least above 20 at least above 30, at least above 40, at least above 50.

In some embodiments, SNPs in linkage disequilibrium with the SNPs of the present disclosure can have a specified genetic recombination distance of less than or equal to about 20 centimorgan (cM) or less. For example, 15 cM or less, 10 cM or less, 9 CM or less, 8 CM or less, 7 cM or less, 6 CM or less, 5 CM or less, 4 cM or less, 3 CM or less, 2 CM or less, 1 cM or less, 0.75 cM or less, 0.5 CM or less, 0.25 cM or less, or 0.1 cM or less. For example, two linked loci within a single chromosome segment can undergo recombination during meiosis with each other at a frequency of less than or equal to about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.75%, about 0.5%, about 0.25%, or about 0.1% or less.

In some embodiments, SNPs in linkage disequilibrium with the SNPs of the present disclosure are within at least 100 kb (which correlates in humans to about 0.1 cM, depending on local recombination rate), at least 50 kb, at least 20 kb or less of each other.

One example approach for the identification of surrogate markers for a particular SNP involves a strategy that presumes that SNPs surrounding the target SNP are in linkage disequilibrium and can therefore provide information about disease susceptibility. Thus, as described herein, surrogate markers can therefore be identified from publicly available databases, such as HAPMAP, by searching for SNPs fulfilling certain criteria which have been found in the scientific community to be suitable for the selection of surrogate marker candidates.

As used herein, "locus" means a specific position or site in a gene (or protein), chromosomal region, chromosome, or genome. As used herein, a "test locus" is a genomic locus (e.g., single nucleotide at a specified position within a chromosome) whose sequence or genotype is assessed according to the present disclosure. A test locus in the present disclosure is often, though not necessarily, a single nucleotide polymorphism. As used herein, "single nucleotide polymorphism" or "SNP" means a genetic variation between individuals; e.g., a single nitrogenous base position in the DNA of organisms that is polymorphic or variable. As used herein, "SNPs" is the plural of SNP. The identifier used herein for SNP loci (e.g., in Tables 1 & 2) is the "rs" identifier often used in the art. This identifier is used, e.g., in the dbSNP database available through the NCBI website and may be updated for changed for any given locus over time. Thus, any "rs" identifier used herein is expressly meant to include new or modified "rs" identifiers assigned to the same locus (i.e., the locus to which the "rs" identifier is assigned in Tables 1 or 2 and in dbSNP as of the date of the filing of this disclosure. References to DNA herein may include derivatives of any given source of DNA such as amplicons, RNA transcripts thereof, etc. As used herein, a "polymorphism" or "polymorphic" locus or position is a locus or position that is variable; that is, within a population, the nucleotide sequence at a polymorphism has more than one version or allele. One example of a polymorphism is a "single nucleotide polymorphism."

As used herein, "marker," "molecular marker" or "marker nucleic acid" means to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, nRNA, mRNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence or to sequences adjacent to or near such marker locus sequence. Nucleic acids are "complementary" when they specifically hybridize in solution, e.g., according to Watson-Crick base pairing rules and at certain minimum hybridization conditions (e.g., medium stringency). A "marker locus" is a locus that can be used to track the presence of a second linked locus, e.g., a linked or correlated locus that encodes or contributes to the population variation of a phenotypic trait. For example, a marker locus can be used to monitor segregation of alleles at a locus that is genetically or physically linked to the marker locus. Thus, a "marker allele," alternatively an "allele of a marker locus" is one of a plurality of polymorphic nucleotide sequences found at a marker locus in a population that is polymorphic for the marker locus. Each of the identified markers is expected to be in close physical and genetic proximity (resulting in physical and/or genetic linkage) to a genetic element that contributes to the relevant phenotype. Markers corresponding to genetic polymorphisms between members of a population can be analyzed (e.g., detected, measured, quantified) by several techniques. These include, e.g., PCR-based sequence specific amplification methods, detection of restriction fragment length polymorphisms (RFLP), detection of isozyme markers, detection of allele specific hybridization (ASH), detection of single nucleotide extension, detection of amplified variable sequences of the genome, detection of self-sustained sequence replication, detection of simple sequence repeats (SSRs), detection of single nucleotide polymorphisms (SNPs), or detection of amplified fragment length polymorphisms (AFLPs).

As used herein, "next generation sequencing" or "NGS" refers to a variety of high-throughput sequencing technologies that parallelize the sequencing process, producing thousands or millions of sequences at once. NGS is generally conducted with the following steps: First, DNA sequencing libraries are generated by clonal amplification by PCR in vitro; second, the DNA is sequenced by synthesis, such that the DNA sequence is determined by the addition of nucleotides to the complementary strand rather through chain-termination chemistry typical of Sanger sequencing; third, the spatially segregated, amplified DNA templates are sequenced simultaneously in a massively parallel fashion, typically without the requirement for a physical separation step. NGS parallelization of sequencing reactions can generate hundreds of megabases to gigabases of nucleotide sequence reads in a single instrument run. Unlike conventional sequencing techniques, such as Sanger sequencing, which typically report the average genotype of an aggregate collection of molecules, NGS technologies typically digitally tabulate the sequence of numerous individual DNA fragments (sequence reads discussed in detail below), such that low frequency variants (e.g., variants present at less than about 10%, 5% or 1% frequency in a heterogeneous population of nucleic acid molecules) can be detected. The term "massively parallel" can also be used to refer to the simultaneous generation of sequence information from many different template molecules by NGS.

NGS strategies can include several methodologies, including, but not limited to: (i) microelectrophoretic methods; (ii) sequencing by hybridization; (iii) real-time observation of single molecules, and (iv) cyclic-array sequencing. Cyclic-array sequencing refers to technologies in which a sequence of a dense array of DNA is obtained by iterative cycles of template extension and imaging-based data collection. Commercially available cyclic-array sequencing technologies include, but are not limited to 454 sequencing, for example, used in 454 Genome Sequencers (Roche Applied Science; Basel), Solexa technology, for example, used in the Illumina Genome Analyzer, Illumina HiSeq, MiSeq, and NextSeq (San Diego, CA), the SOLiD platform (Applied Biosystems; Foster City, CA), the Polonator (Dover/Harvard) and HeliScope Single Molecule Sequencer technology (Helicos; Cambridge, MA). Other NGS methods include single molecule real time sequencing (e.g., Pacific Bio) and ion semiconductor sequencing (e.g., Ion Torrent sequencing). See, e.g., Shendure & Ji, *Next Generation DNA Sequencing*, NAT. BIOTECH. (2008) 26:1135-1145 for a more detailed discussion of NGS sequencing technologies.

As used herein, "patient" or "individual" or "subject" refers to a human. A subject can be male or female.

As used herein, "sample" or "biological sample" refers to samples such as biopsy or tissue samples, frozen samples, blood and blood fractions or products (e.g., serum, platelets, red blood cells, and the like), tumor samples, sputum, bronchoalveolar lavage, cultured cells, e.g., primary cultures, explants, and transformed cells, stool, urine, etc. A "biopsy" refers to the process of removing a tissue sample for diagnostic or prognostic evaluation, and to the tissue specimen derived from such a process. Any suitable biopsy technique can be applied to the methods of the present disclosure. The biopsy technique applied will depend on the tissue type to be evaluated (e.g., lung etc.), the size and type of the tumor, among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis made by endoscopy or fluoroscopy can require a "core-needle biopsy", or a "fine-needle aspiration biopsy" which generally obtains a suspension of cells from within a target tissue. A "bodily fluid" include all fluids obtained from a mammalian body, either processed (e.g., serum) or unprocessed, which can include, for example, blood, plasma, urine, lymph, gastric juices, bile, serum, saliva, sweat, and spinal and brain fluids. A biological sample is typically obtained from a subject. As used herein, "cancer cell samples" or "tumor sample" means a specimen comprising either at least one cancer cell or biomolecules derived therefrom, including without limitation, lung cancer (e.g., non-small cell lung cancer (NSCLC)), ovarian cancer, colorectal cancer, breast cancer, endometrial cancer, or prostate cancer. Non-limiting examples of such biomolecules include nucleic acids and proteins. Biomolecules "derived" from a cancer cell sample include molecules located within or extracted from the sample as well as artificially synthesized copies or versions of such biomolecules. One illustrative, non-limiting example of such artificially synthesized molecules includes PCR amplification products in which nucleic acids from the sample serve as PCR templates. "Nucleic acids of" a cancer cell sample include nucleic acids located in a cancer cell or biomolecules derived from a cancer cell.

As used herein, "sequence read" means the sequence of an individual DNA molecule sequenced in a sequencing reaction. Especially in next-generation sequencing, individual DNA molecules used for sequencing can be relatively short (e.g., ranging from 50 nt to 1,000 nt). These molecules are typically heavily overlapping in their sequences. Thus, any individual test locus is contained within numerous distinct DNA molecules in the sample. When each individual molecule is sequenced (often in parallel), the numerous resulting "sequence reads" can be aligned against each other and/or against a larger reference sequence (e.g., a reference human genome sequence such as the hg19 version of the human genome assembly available at the University of California Santa Clara's Genome Browser website). Generally speaking, a greater number of reliably sequenced (or "informative") reads containing (or "covering") any individual locus yields greater accuracy and confidence in the genotype/sequence at that locus. Thus, in some specific embodiments of each of the above aspects of the disclosure a test locus (or an allele at that locus) may be counted only if it is covered by at least some minimal number of sequence reads in the sequencing reaction(s).

As used herein, "score" means a value or set of values selected so as to provide a quantitative measure or assessment of a variable or characteristic of a subject or the subject's condition or physiology. The value(s) comprising the score can be based on, derived from or incorporate, for example, quantitative data resulting in a measured amount of one or more sample constituents obtained from the subject. In certain embodiments the score can be derived from a single constituent, parameter or assessment, while in other embodiments the score is derived from multiple constituents, parameters and/or assessments. The score can be based upon or derived from an interpretation function; e.g., an interpretation function derived from a particular predictive model using any of various statistical algorithms. A "change in score" can refer to the absolute change in score, e.g. from one time point to the next, or the percent change in score, or the change in the score per unit time (i.e., the rate of score change).

As used herein, the term "treatment" or "therapy" or "therapeutic regimen" includes all clinical management of a subject and interventions, whether biological, chemical, physical, or a combination thereof, intended to sustain, ameliorate, improve, or otherwise alter the condition of a subject. These terms may be used synonymously herein. Treatments include but are not limited to administration of prophylactics or therapeutic compounds (including small molecule and biologic drugs), exercise regimens, physical therapy, dietary modification and/or supplementation, bariatric surgical intervention, administration of therapeutic compounds (prescription or over-the-counter), and any other treatments known in the art as efficacious in preventing, delaying the onset of, or ameliorating disease characterized by HML. A "response to treatment" includes a subject's response to any of the above-described treatments, whether biological, chemical, physical, or a combination of the foregoing. A "treatment course" relates to the dosage, duration, extent, etc. of a particular treatment or therapeutic regimen. An initial therapeutic regimen as used herein is the first line of treatment.

As used herein, "variant allele ratio" means the proportion of informative sequence reads harboring a particular nucleotide at a specific locus as a proportion of the total sequence reads. For example, if a test locus is covered by 100 informative sequence reads in a particular sequencing reaction and 15 reads carry a particular nucleotide (e.g., a risk modifying allele), then the risk modifying allele ratio is 15%. In some contexts variant allele ratios that are too low or too high may indicate unreliability in an allele or genotype call (sometimes referred to herein as a call failure). For example, if the variant allele ratio is around 1%, this can in many cases be due to sequencing artifacts and noise (e.g., a small proportion of sequence reads simply contain sequencing errors). Thus, in some specific embodiments of each of the above aspects of the disclosure a test locus (or an allele or specific nucleotide at that locus) may be counted only if the variant allele ratio is within a specific (e.g., pre-specified) range.

16

Aspects of the Disclosure

The present disclosure generally relates to methods, systems and kits for detecting genotypes at polymorphic loci in a biological specimen and methods, systems and kits for clinically applying such genotype detection in detecting risk for developing cancer and, in turn, directing clinical management. Some disclosed methods generally involve analyzing a plurality of genomic loci to detect a subject's genotype at these loci and estimating the subject's risk for developing cancer based at least in part on the detection of these genotypes. The present disclosure reports data enabling methods, systems and kits utilizing the loci (and panels of loci) listed in Table 1.

TABLE 1

| SNP Designation | SNP Designation | SNP Designation | SNP Designation |
|---|---|---|---|
| Panel 1 | | | |
| chr17:29230520:D | rs12662670 | rs2236007 | rs6507583 |
| rs10069690 | rs12710696 | rs2363956 | rs6678914 |
| rs1011970 | rs1292011 | rs2380205 | rs6762644 |
| rs1045485 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11075995 | rs1353747 | rs3817198 | rs745570 |
| rs11199914 | rs1432679 | rs3903072 | rs75915166 |
| rs11242675 | rs1436904 | rs4245739 | rs7707921 |
| rs11249433 | rs1550623 | rs4593472 | rs7726159 |
| rs11552449 | rs16857609 | rs4808801 | rs78540526 |
| rs11571833 | rs17356907 | rs4849887 | rs7904519 |
| rs11621587 (LD SNP for rs11627032) | rs17529111 | rs4973768 | rs8170 |
| rs11627032 | rs17817449 | rs527616 | rs865686 |
| rs11780156 | rs17879961 | rs554219 | rs889312 |
| rs11814448 | rs186951 (LD SNP for rs13162653) | rs6001930 | rs9257408 |
| rs11820646 | rs2012709 | rs616488 | rs941764 |
| rs12048493 | rs2016394 | rs62070644 (LD SNP for chr17:29230520:D) | rs9693444 |
| rs12405132 | rs204247 | rs6472903 | rs9790517 |
| rs12422552 | rs2046210 | rs6504950 | rs999737 |
| rs12493607 | | | |
| Panel 2 | | | |
| rs10069690 | rs12710696 | rs2363956 | rs6507583 |
| rs1011970 | rs1292011 | rs2380205 | rs6678914 |
| rs1045485 | rs13162653 | rs2588809 | rs6762644 |
| rs10472076 | rs132390 | rs2736108 | rs6796502 |
| rs1053338 | rs13267382 | rs2823093 | rs6828523 |
| rs10759243 | rs13281615 | rs2943559 | rs6964587 |
| rs10771399 | rs13329835 | rs2981579 | rs704010 |
| rs10941679 | rs13365225 | rs3760982 | rs7072776 |
| rs10995190 | rs13387042 | rs3803662 | rs720475 |
| rs11075995 | rs1353747 | rs3817198 | rs72755295 |
| rs11199914 | rs1432679 | rs3903072 | rs745570 |
| rs11242675 | rs1436904 | rs4245739 | rs75915166 |
| rs11249433 | rs1550623 | rs4593472 | rs7707921 |
| rs11552449 | rs16857609 | rs4808801 | rs7726159 |
| rs11571833 | rs17356907 | rs4849887 | rs78540526 |
| rs11627032 | rs17529111 | rs4973768 | rs7904519 |
| rs11780156 | rs17817449 | rs527616 | rs8170 |
| rs11814448 | rs17879961 | rs554219 | rs865686 |

TABLE 1-continued

| SNP Designation | SNP Designation | SNP Designation | SNP Designation |
|---|---|---|---|
| rs11820646 | rs2012709 | rs6001930 | rs889312 |
| rs12405132 | rs2016394 | rs616488 | rs941764 |
| rs12422552 | rs204247 | rs62070644 (LD SNP for chr17:29230520:D) | rs9693444 |
| rs12493607 | rs2046210 | rs6472903 | rs9790517 |
| rs12662670 | rs2236007 | rs6504950 | rs999737 |

Panel 3

| | | | |
|---|---|---|---|
| rs10069690 | rs13162653 | rs2588809 | rs6796502 |
| rs1011970 | rs132390 | rs2736108 | rs6828523 |
| rs10472076 | rs13267382 | rs2823093 | rs6964587 |
| rs1053338 | rs13281615 | rs2943559 | rs704010 |
| rs10759243 | rs13329835 | rs2981579 | rs7072776 |
| rs10771399 | rs13365225 | rs3760982 | rs720475 |
| rs10941679 | rs13387042 | rs3803662 | rs72755295 |
| rs10995190 | rs1353747 | rs3817198 | rs745570 |
| rs11199914 | rs1432679 | rs3903072 | rs75915166 |
| rs11242675 | rs1436904 | rs4593472 | rs7707921 |
| rs11249433 | rs1550623 | rs4808801 | rs7726159 |
| rs11552449 | rs16857609 | rs4849887 | rs78540526 |
| rs11571833 | rs17356907 | rs4973768 | rs7904519 |
| rs11627032 | rs17529111 | rs527616 | rs8170 |
| rs11780156 | rs17817449 | rs554219 | rs865686 |
| rs11814448 | rs17879961 | rs6001930 | rs889312 |
| rs11820646 | rs2012709 | rs616488 | rs941764 |
| rs12405132 | rs2016394 | rs62070644 (LD SNP for chr17:29230520:D) | rs9693444 |
| rs12493607 | rs204247 | rs6472903 | rs9790517 |
| rs12662670 | rs2046210 | rs6504950 | rs999737 |
| rs12710696 | rs2236007 | rs6507583 | |
| rs1292011 | rs2363956 | rs6762644 | |

Panel 4

| | | | |
|---|---|---|---|
| rs10069690 | rs1292011 | rs2236007 | rs6762644 |
| rs1011970 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11199914 | rs1353747 | rs3817198 | rs745570 |
| rs11242675 | rs1432679 | rs3903072 | rs75915166 |
| rs11249433 | rs1436904 | rs4593472 | rs7707921 |
| rs11552449 | rs1550623 | rs4808801 | rs7726159 |
| rs11571833 | rs16857609 | rs4849887 | rs78540526 |
| rs11627032 | rs17356907 | rs4973768 | rs7904519 |
| rs11780156 | rs17529111 | rs527616 | rs865686 |
| rs11814448 | rs17817449 | rs554219 | rs889312 |
| rs11820646 | rs17879961 | rs6001930 | rs941764 |
| rs12048493 | rs2012709 | rs616488 | rs9693444 |
| rs12405132 | rs2016394 | rs6472903 | rs999737 |
| rs12493607 | rs204247 | rs6504950 | |
| rs12662670 | rs2046210 | rs6507583 | |

Accordingly, one aspect of the present disclosure relates to a method for genotyping a subject comprising: analyzing a sample of DNA obtained or derived from the subject to detect the genotype for a plurality of test genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more loci or a panel of loci listed in Table 1, and/or for one or more of such test genomic locus a locus in linkage disequilibrium with one or more thereof.

Another aspect of the present disclosure relates to a method for assessing risk for developing cancer comprising:

(1) analyzing a sample of DNA obtained or derived from a subject to detect the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test locus a locus in linkage disequilibrium with one or more thereof; and (2) determining (or estimating) the subject's risk for developing cancer based at least in part on the genotypes detected in (1).

In another aspect of the present disclosure, a combined determination (or estimate) of risk is made by combining clinical characteristics of the subject with the subject's genotypes for the test genomic loci. Accordingly, another aspect of the present disclosure relates to a method for assessing risk for developing cancer comprising:

(1) analyzing a sample of DNA obtained or derived from a subject to detect the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;

(2) evaluating one or more clinical characteristics of the subject; and (3) determining (or estimating) the subject's risk for developing cancer based at least in part on the genotypes detected in (1) and the clinical characteristic(s) evaluated in (2).

In another aspect of the present disclosure, the subject's genotypes for the test loci are incorporated into a test score (e.g., numerical value), which can in turn be used to diagnose a risk of cancer that is above (or not above) a reference risk level. Accordingly, another aspect of the present disclosure relates to a method for assessing risk for developing cancer comprising:

(1) analyzing a sample of DNA obtained or derived from a subject to detect the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;

(2) calculating a test score incorporating the genotypes detected in (1); and (3)(a) diagnosing a subject for whom the score in (2) exceeds a reference score as having a test likelihood of developing cancer that is higher than a reference likelihood of developing cancer; or (3)(b) diagnosing a subject for whom the score in (2) does not exceed a reference score as having a test likelihood of developing cancer that is equal to or lower than a reference likelihood of developing cancer.

In another aspect of the present disclosure, the test score is a combined score incorporating both the genotypes detected in the subject and the subject's clinical characteristics. Accordingly, another aspect of the present disclosure relates to a method for assessing risk for developing cancer comprising:

(1) analyzing a sample of DNA obtained or derived from a subject to detect the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;

(2) evaluating one or more clinical characteristics of the subject;

(3) calculating a test score incorporating the genotypes detected in (1) and the clinical characteristic(s) evaluated in (2); and (4)(a) diagnosing a subject for whom the score in (2) exceeds a reference score as having a test likelihood of developing cancer that is higher than a reference likelihood of developing cancer; or (4)(b) diagnosing a subject for whom the score in (2) does not exceed a reference score as having a test likelihood of developing cancer that is equal to or lower than a reference likelihood of developing cancer.

Another aspect of the present disclosure relates to a method of screening for cancer in a subject comprising assessing the risk of the subject for developing cancer as disclosed in any aspect of the present disclosure, and screening for cancer (or recommending or prescribing screening for cancer) in a subject determined to have a risk for developing breast cancer that is increased (e.g., over general population risk) or is above some threshold (e.g., greater than 15%, 20%, 25%, 30%, 35%, 40%, 50%, 60%, 70%, 80%, 90% or greater risk of developing cancer).

Another aspect of the present disclosure relates to methods of treating subjects. This may include a method for treating a subject comprising:

(1) determining the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;

(2) determining (or estimating) the subject's risk for developing cancer based at least in part on the genotypes determined in (1);

(3) prescribing or administering one or more treatment modalities indicated based at least in part on the risk determined (or estimated) in (2).

This may also include a method for preventing cancer in a subject comprising assessing the risk of the subject for developing cancer as disclosed in any aspect of the present disclosure, and administering an anti-cancer therapy (e.g., medical management that includes some action meant to prevent cancer) to a subject determined to have a risk for developing breast cancer that is increased (e.g., over general population risk) or is above some threshold (e.g., greater than 15%, 20%, 25%, 30%, 35%, 40%, 50%, 60%, 70%, 80%, 90% or greater risk of developing cancer).

This may also include an anti-breast cancer therapy for use in preventing breast cancer in a subject at risk thereof, wherein the risk of the subject for developing cancer is determined as disclosed in any aspect of the present disclosure. In some embodiments, the therapy inhibits estrogen.

Another aspect of the disclosure provides a kit for genotyping a subject comprising: a compartmentalized container; reagents for analyzing a sample of DNA obtained or derived from the subject to detect the genotype for a plurality of test genomic loci, wherein the plurality consists of at most X genomic loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test genomic locus a locus in linkage disequilibrium with one or more thereof; and instructions for use of the reagents.

Another aspect of the disclosure provides a system for genotyping a subject, comprising: (1) a sample analyzer for analyzing DNA in, extracted from or derived from a sample of the subject to detect the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof, wherein the sample analyzer contains (a) the sample, (b) genomic DNA from the sample, (c) transcript RNA from the sample, or (d) DNA derived (e.g., synthesized or amplified) from said genomic DNA; (2) one or more computer programs for performing any one, all, or any combination of the following functions (a) a computer program for querying the subject's genotype data; (b) calculating the subject's risk for developing cancer based at least on the subject's genotype data; (c) calculating a test score based on or derived from the subject's genotype data; (d) comparing the test score to one or more reference scores; (e) concluding whether there is an increased risk of cancer based at least in part on the comparison in (d); and (f) outputting (e.g., displaying) the conclusion in (e).

Another aspect of the present disclosure provides computer program products comprising a computer-usable medium having computer-readable program codes or instructions embodied thereon for enabling a processor to carry out the methods of the disclosure. Generally speaking, the computer-usable medium comprises (1) a computer program for receiving, storing, and/or retrieving a subject's genotype data for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof; and (2) one or more computer programs for performing any one, all, or any combination of the following functions (a) a computer program for querying the subject's genotype data; (b) calculating the subject's risk for developing cancer based at least on the subject's genotype data; (c) calculating a test score based on or derived from the subject's genotype data; (d) comparing the test score to one or more reference scores; (e) concluding whether there is an increased risk of cancer based at least in part on the comparison in (d); and (f) outputting (e.g., displaying) the conclusion in (e). In some embodiments this program for outputting the conclusion may comprise a computer program for informing a health care professional of the conclusion.

Another aspect of the present disclosure relates to a computer implemented method for assessing the risk of a subject for developing cancer, the method operable in a computing system comprising a processor and a memory, the method comprising:

(1) receiving genetic risk data for the subject, wherein the genetic risk data was obtained by detecting, in a sample derived from the subject, the genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof;

(2) optionally processing the data to combine the genetic risk data with clinical risk data to obtain the risk of the subject for developing cancer;

(3) outputting the risk of the subject for developing cancer.

In some embodiments, the clinical risk data and/or genetic risk data for the subject are received from a user interface coupled to the computing system. In some embodiments, the clinical risk data and/or genetic risk data for the subject are received from a remote device across a wireless communications network. In some embodiments, outputting comprises outputting information to a user interface coupled to the computing system. In some embodiments, outputting comprises transmitting information to a remote device across a wireless communications network.

Another aspect of the present disclosure relates to a system configured to perform the disclosed methods. This may include a system for assessing the risk of a subject for developing cancer comprising:

(a) system instructions for performing a genetic risk assessment of the subject according to any of the method aspects of the present disclosure; and (b) optionally system instructions for performing a clinical risk assessment of the subject;

(c) optionally system instructions for combining the clinical risk assessment with the genetic risk assessment to obtain the risk of a human female subject for developing breast cancer.

As will be apparent, at least some features of the methods, kits and systems can be used together in combination. For example, systems for identifying correlations between breast cancer susceptibility and polymorphisms can be used for practicing the methods herein. Kits can be used for practicing the methods herein. Thus, described features of the systems, methods and kits can be applied to the different systems, methods and kits herein.

FURTHER EMBODIMENTS OF THESE ASPECTS

The following section describes numerous specific embodiments of the more general aspects of the disclosure described in the preceding section. Unless expressly stated otherwise (i.e., unless an embodiment is expressly stated to apply to one ore more aspects and not to others), each description of each of these embodiments hereby incorporates by reference the details of each aspect described in the preceding section as if fully reproduced. As a non-limiting and illustrative example, the following paragraph describes specific embodiments in which the number of genomic loci analyzed is at most some specific number, without reproducing the other elements of any method described above (e.g., the step of analyzing a sample of DNA obtained or derived from the subject to detect the genotype for a plurality of test genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more loci or a panel of loci listed in Table 1, and/or for one or more of such test genomic locus a locus in linkage disequilibrium with one or more thereof). This is because such reproduction is not necessary to describe this embodiment since every such description of every specific embodiment, by virtue of this paragraph, already incorporates by reference all such additional elements of the method described in the preceding section. In other words, each description of a specific embodiment in the present section typically expands on and specifies one element of a more general aspect of the disclosure by substituting its more general counterpart (e.g., simply "at most X") in the preceding section with expanded specific versions in the present section (e.g., X is at most 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1,000, [ . . . ]). Another non-limiting, illustrative example involves specific embodiments of the step of "analyzing a sample of DNA obtained or derived from a subject to detect the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof". Any specific embodiments described in the present section (e.g., where "analyzing" comprises sequencing genomic DNA to detect genotypes, where "analyzing" comprises microarray analysis to detect genotypes, etc.) apply to and can be interchanged with each instance of this step described in every aspect of the disclosure in the preceding section that includes this step.

Accordingly, in some embodiments of each of the above aspects of the disclosure, X (the number of genomic loci analyzed) is at most 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1,000, 1,250, 1,500, 1,750, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275, 000, 300,000, 325,000, 350,000, 375,000, 400,000, 425,000, 450,000, 475,000, 500,000, 550,000, 600,000, 650,000, 700, 000, 750,000, 800,000, 850,000, 900,000, 950,000, 1,000, 000, 1,250,000, 1,500,000, 1,750,000, 2,000,000, 2,500,000, 3,000,000, 3,500,000, 4,000,000, 4,500,000, or 5,000,000 loci.

In some embodiments determining (or estimating) the subject's risk for developing cancer based at least in part on the genotypes detected in (1) comprises calculating the subject's percent probability of developing cancer based at least in part on the genotypes detected in (1). In some embodiments such calculating comprises calculating a test score incorporating the genotypes detected in (1) and calculating the subject's percent probability of developing cancer based at least in part on such test score. In some such embodiments calculating the subject's percent probability of developing cancer based at least in part on the test score comprises multiplying the test score by some other value. In some such embodiments such other value is another score (optionally termed a clinical score) that is (or corresponds to) the subject's percent probability of developing cancer attributable to any single, any set or all known factors other than the genotypes detected in (1). In some embodiments the subject's percent probability of developing cancer based at least in part on the test score is calculated according to either of the following formulae (I or II):

$$\text{Test Score}=1-(1-[\text{Clinical Score}])^{exp(C1*[\text{Test Score}])} \quad \text{Formula (I):}$$

$$\text{Test Score}=1-(1-[\text{Clinical Score}])^{(exp(C1*[\text{Test Score}]+C2)} \quad \text{Formula (II):}$$

where C1 and C2 are constants. Formula (I) is (or may be thought of as) Formula (II) where C2=0. In some embodiments C1 is 0.77, 0.75, or 0.752933. In some embodiments C1 is about 0.77, 0.75, or 0.752933. In some embodiments C1 is 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, or 0.9. In some embodiments C2 is −0.055607, or 0.056. In some embodiments C2 is about 0.77, 0.75, or 0.752933. In some embodiments C1 is 0.04, 0.041, 0.042, 0.043, 0.044, 0.045, 0.046, 0.047, 0.048, 0.049, 0.05, 0.051, 0.052, 0.053, 0.054, 0.055, 0.056, 0.057, 0.058, 0.059, 0.06, 0.061, 0.062, 0.063, 0.064, 0.065, 0.066, 0.067, 0.068, 0.069, or 0.07. In some embodiments the clinical score is the subject's Tyrer-Cuzick score or percent probability of developing cancer.

In some embodiments the test score is calculated by one or more or all of the following: assigning a coefficient or weight to each test locus (e.g., the coefficient in Table 2 corresponding to such test locus), assigning a genotype value to the presence or absence of one or more possible alleles at each locus, multiplying each genotype value by a coefficient to derive a weighted genotype value for each locus, summing the weighted genotype values to derive a raw test score, and scaling the raw test score to derive a final test score. In some embodiments the test score is calculated by assigning to each test locus (e.g., all or a panel of the loci in Table 1) a coefficient (e.g., the coefficient in Table 2 corresponding to such test locus), assigning a genotype value corresponding to number of risk modifying alleles detected at each locus, multiplying each genotype value by the coefficient to derive a weighted genotype value for each locus, summing the weighted genotype values to derive the test score. In some embodiments the weighted genotype value is derived by further centering each genotype value by a mean allele copy value. In some embodiments the coefficients, mean allele copy values, and risk modifying alleles are as shown in Table 2 (throughout this disclosure, unless stated otherwise or context indicates only one or both, any reference to "Table 2" includes Table 2A or Table 2B). Where a locus has been assigned a weight or coefficient of 0 in Table 2, in some embodiments such locus may be excluded from the assay (e.g., not tested in the genotyping portion of the method).

TABLE 2A

| Locus | Coefficient | Mean Allele Copy Value | Non-Risk Modifying Allele/Risk Modifying Allele |
|---|---|---|---|
| rs10069690 | 0.026958329 | 0.530201342 | C/T |
| rs1011970 | 0.049271027 | 0.35910288 | G/T |
| rs1045485 | 0 | 0.248577011 | G/C |
| rs10472076 | 0.041714166 | 0.746495625 | T/C |
| rs1053338 | 0.078324973 | 0.285022513 | A/G |
| rs10759243 | 0.049214158 | 0.612947073 | C/A |
| rs10771399 | −0.147414808 | 0.215784555 | A/G |
| rs10941679 | 0.108578125 | 0.511426387 | A/G |
| rs10995190 | −0.148535718 | 0.28944015 | G/A |
| rs11075995 | 0 | 1.535213661 | A/T |
| rs11199914 | −0.058933344 | 0.660521621 | C/T |
| rs11242675 | 0.051007202 | 1.277801376 | C/T |
| rs11249433 | 0.091673402 | 0.813354855 | A/G |

TABLE 2A-continued

| Locus | Coefficient | Mean Allele Copy Value | Non-Risk Modifying Allele/Risk Modifying Allele |
|---|---|---|---|
| rs11552449 | 0.071856175 | 0.332172288 | C/T |
| rs11571833 | 0.234868161 | 0.020049274 | A/T |
| rs11627032 | −0.061139792 | 0.513465296 | T/C |
| rs11780156 | 0.062130382 | 0.377453063 | C/T |
| rs11814448 | 0.192433421 | 0.056070003 | A/C |
| rs11820646 | 0.046036656 | 1.21400051 | T/C |
| rs12405132 | −0.047146158 | 0.72194376 | C/T |
| rs12422552 | 0 | 0.546342707 | G/C |
| rs12493607 | 0.05649894 | 0.668252485 | G/C |
| rs12662670 | 0.11230336 | 0.17254269 | T/G |
| rs12710696 | −0.036544636 | 1.254608784 | T/C |
| rs1292011 | −0.081428965 | 0.825928128 | A/G |
| rs13162653 | −0.046482691 | 0.886500722 | G/T |
| rs132390 | −0.091152573 | 1.927703679 | C/T |
| rs13267382 | −0.04495086 | 1.268966103 | A/G |
| rs13281615 | 0.08794035 | 0.854727721 | A/G |
| rs13329835 | 0.072706322 | 0.465041203 | A/G |
| rs13365225 | −0.056944707 | 0.368702744 | A/G |
| rs13387042 | −0.126364519 | 0.945629088 | A/G |
| rs1353747 | −0.070997825 | 0.18282219 | T/G |
| rs1432679 | −0.062648697 | 1.102795005 | C/T |
| rs1436904 | −0.053706699 | 0.775889899 | T/G |
| rs1550623 | 0.06328499 | 1.685413304 | G/A |
| rs16857609 | 0.062575146 | 0.534194206 | C/T |
| rs17356907 | −0.091945154 | 0.586696118 | A/G |
| rs17529111 | 0.044336223 | 0.421629428 | T/C |
| rs17817449 | −0.07523292 | 0.789482627 | T/G |
| rs17879961 | 0.305000109 | 0.006116728 | A/G |
| rs2012709 | 0.043409743 | 0.959136862 | C/T |
| rs2016394 | −0.045813528 | 0.925324951 | G/A |
| rs204247 | −0.042906751 | 1.118851414 | G/A |
| rs2046210 | 0.046490174 | 0.73332767 | G/A |
| rs2236007 | −0.08295447 | 0.410585337 | G/A |
| rs2363956 | −0.027486299 | 1.028884547 | T/G |
| rs2380205 | 0 | 0.867810721 | C/T |
| rs2588809 | −0.062601149 | 1.650157166 | T/C |
| rs2736108 | −0.053261024 | 0.584997027 | C/T |
| rs2823093 | −0.073638714 | 0.538696797 | G/A |
| rs2943559 | 0.127688411 | 0.164556962 | A/G |
| rs2981579 | −0.222437643 | 1.120040778 | A/G |
| rs3760982 | −0.055158121 | 1.061677003 | A/G |
| rs3803662 | −0.200423084 | 1.41568261 | A/G |
| rs3817198 | 0.072138405 | 0.64947753 | T/C |
| rs3903072 | −0.050653438 | 0.92362586 | G/T |
| rs4245739 | 0 | 1.444227338 | C/A |
| rs4593472 | −0.04863385 | 0.700365305 | C/T |
| rs4808801 | −0.064367687 | 0.67861694 | A/G |
| rs4849887 | 0.088084694 | 1.793050718 | T/C |
| rs4973768 | 0.081840295 | 0.971455271 | C/T |
| rs527616 | 0.036610672 | 1.286551695 | C/G |
| rs554219 | 0.122273766 | 0.264123694 | C/G |
| rs6001930 | 0.126088053 | 0.206949282 | T/C |
| rs616488 | −0.057756725 | 0.648882848 | A/G |
| rs62070644 | −0.070880132 | 0.535978252 | G/T |
| rs6472903 | 0.092201539 | 1.660436666 | G/T |
| rs6504950 | −0.066016297 | 0.555687707 | G/A |
| rs6507583 | −0.09350981 | 0.141194461 | A/G |
| rs6678914 | 0 | 0.810211537 | G/A |
| rs6762644 | 0.065043099 | 0.779627899 | A/G |
| rs6796502 | −0.079300047 | 0.198793645 | G/A |
| rs6828523 | −0.095482559 | 0.23192592 | C/A |
| rs6964587 | 0.048643535 | 0.788378218 | G/T |
| rs704010 | −0.06833486 | 1.223515419 | T/C |
| rs7072776 | −0.052827841 | 1.398181973 | A/G |
| rs720475 | −0.051421742 | 0.511171523 | G/A |
| rs72755295 | 0.147744371 | 0.07076714 | A/G |
| rs745570 | −0.047042413 | 1.015886501 | A/G |
| rs75915166 | 0.005158994 | 0.123863733 | C/A |
| rs7707921 | 0.061305396 | 1.500297341 | T/A |
| rs7726159 | 0.031804381 | 0.680995667 | C/A |
| rs78540526 | 0.160069987 | 0.154872143 | C/T |
| rs7904519 | 0.052948974 | 0.953020134 | A/G |
| rs8170 | 0.034707231 | 0.364624926 | G/A |
| rs865686 | 0.101266952 | 1.264633421 | G/T |
| rs889312 | −0.105582226 | 1.42035511 | C/A |
| rs941764 | 0.059962424 | 0.711324441 | A/G |

TABLE 2A-continued

| Locus | Coefficient | Mean Allele Copy Value | Non-Risk Modifying Allele/Risk Modifying Allele |
|---|---|---|---|
| rs9693444 | −0.068418087 | 1.32885906 | A/C |
| rs9790517 | 0.038352073 | 0.440999065 | C/T |
| rs999737 | −0.078119341 | 0.448050293 | C/T |

TABLE 2B

| Locus | Coefficient | Mean Allele Copy Value | Non-Risk Modifying Allele/Risk Modifying Allele |
|---|---|---|---|
| rs10069690 | 0.026958329 | 0.530201342 | C/T |
| rs10069690 | 0.026958 | 0.52 | C/T |
| rs1011970 | 0.049271 | 0.34 | G/T |
| rs1045485 | 0 | 0.26 | G/C |
| rs10472076 | 0.041714 | 0.76 | T/C |
| rs1053338 | 0.078325 | 0.26 | A/G |
| rs10759243 | 0.049214 | 0.58 | C/A |
| rs10771399 | −0.14741 | 0.24 | A/G |
| rs10941679 | 0.108578 | 0.5 | A/G |
| rs10995190 | −0.14854 | 0.32 | G/A |
| rs11075995 | 0 | 1.52 | A/T |
| rs11199914 | −0.05893 | 0.64 | C/T |
| rs11242675 | 0.051007 | 1.24 | C/T |
| rs11249433 | 0.091673 | 0.8 | A/G |
| rs11552449 | 0.071856 | 0.32 | C/T |
| rs11571833 | 0.234868 | 0.02 | A/T |
| rs11627032 | −0.06114 | 0.52 | T/C |
| rs11780156 | 0.06213 | 0.32 | C/T |
| rs11814448 | 0.192433 | 0.04 | A/C |
| rs11820646 | 0.046037 | 1.18 | T/C |
| rs12405132 | −0.04715 | 0.72 | C/T |
| rs12422552 | 0 | 0.52 | G/C |
| rs12493607 | 0.056499 | 0.68 | G/C |
| rs12662670 | 0.112303 | 0.14 | T/G |
| rs12710696 | −0.03654 | 1.28 | T/C |
| rs1292011 | −0.08143 | 0.84 | A/G |
| rs13162653 | −0.04648 | 0.9 | G/T |
| rs132390 | −0.09115 | 1.92 | C/T |
| rs13267382 | −0.04495 | 1.28 | A/G |
| rs13281615 | 0.08794 | 0.8 | A/G |
| rs13329835 | 0.072706 | 0.44 | A/G |
| rs13365225 | −0.05694 | 0.34 | A/G |
| rs13387042 | −0.12636 | 0.98 | A/G |
| rs1353747 | −0.071 | 0.2 | T/G |
| rs1432679 | −0.06265 | 1.14 | C/T |
| rs1436904 | −0.05371 | 0.8 | T/G |
| rs1550623 | 0.063285 | 1.68 | G/A |
| rs16857609 | 0.062575 | 0.52 | C/T |
| rs17356907 | −0.09195 | 0.6 | A/G |
| rs17529111 | 0.044336 | 0.44 | T/C |
| rs17817449 | −0.07523 | 0.8 | T/G |
| rs17879961 | 0.305 | 0.0098 | A/G |
| rs2012709 | 0.04341 | 0.92 | C/T |
| rs2016394 | −0.04581 | 0.96 | G/A |
| rs204247 | −0.04291 | 1.12 | G/A |
| rs2046210 | 0.04649 | 0.68 | G/A |
| rs2236007 | −0.08295 | 0.42 | G/A |
| rs2363956 | −0.02749 | 1.02 | T/G |
| rs2380205 | 0 | 0.88 | C/T |
| rs2588809 | −0.0626 | 1.68 | T/C |
| rs2736108 | −0.05326 | 0.58 | C/T |
| rs2823093 | −0.07364 | 0.54 | G/A |
| rs2943559 | 0.127688 | 0.14 | A/G |
| rs2981579 | −0.22244 | 1.2 | A/G |
| rs3760982 | −0.05516 | 1.08 | A/G |
| rs3803662 | −0.20042 | 1.48 | A/G |
| rs3817198 | 0.072138 | 0.62 | T/C |
| rs3903072 | −0.05065 | 0.94 | G/T |
| rs4245739 | 0 | 1.48 | C/A |
| rs4593472 | −0.04863 | 0.7 | C/T |
| rs4808801 | −0.06437 | 0.7 | A/G |
| rs4849887 | 0.088085 | 1.8 | T/C |
| rs4973768 | 0.08184 | 0.94 | C/T |

TABLE 2B-continued

| Locus | Coefficient | Mean Allele Copy Value | Non-Risk Modifying Allele/Risk Modifying Allele |
|---|---|---|---|
| rs527616 | 0.036611 | 1.24 | C/G |
| rs554219 | 0.122274 | 0.24 | C/G |
| rs6001930 | 0.126088 | 0.22 | T/C |
| rs616488 | −0.05776 | 0.66 | A/G |
| rs62070644 | −0.07088 | 0.4 | G/T |
| rs6472903 | 0.092202 | 1.64 | G/T |
| rs6504950 | −0.06602 | 0.56 | G/A |
| rs6507583 | −0.09351 | 0.14 | A/G |
| rs6678914 | 0 | 0.82 | G/A |
| rs6762644 | 0.065043 | 0.8 | A/G |
| rs6796502 | −0.0793 | 0.18 | G/A |
| rs6828523 | −0.09548 | 0.24 | C/A |
| rs6964587 | 0.048644 | 0.78 | G/T |
| rs704010 | −0.06833 | 1.24 | T/C |
| rs7072776 | −0.05283 | 1.42 | A/G |
| rs720475 | −0.05142 | 0.5 | G/A |
| rs72755295 | 0.147744 | 0.06 | A/G |
| rs745570 | −0.04704 | 1 | A/G |
| rs75915166 | 0.005159 | 0.12 | C/A |
| rs7707921 | 0.061305 | 1.54 | T/A |
| rs7726159 | 0.031804 | 0.68 | C/A |
| rs78540526 | 0.16007 | 0.16 | C/T |
| rs7904519 | 0.052949 | 0.92 | A/G |
| rs8170 | 0.034707 | 0.38 | G/A |
| rs865686 | 0.101267 | 1.24 | G/T |
| rs889312 | −0.10558 | 1.44 | C/A |
| rs941764 | 0.059962 | 0.68 | A/G |
| rs9693444 | −0.06842 | 1.36 | A/C |
| rs9790517 | 0.038352 | 0.44 | C/T |
| rs999737 | −0.07812 | 0.46 | C/T |

In some embodiments, the test score is calculated according to the following non-limiting example:

1. Inputs for each patient include test locus calls (0, 1 or 2 copies) for the risk modifying allele at each test locus.

EXAMPLE

| Test Locus | Genotype Value |
|---|---|
| rs10069690 | 0 |
| rs1011970 | 1 |
| rs1045485 | 2 |
| rs10472076 | Fail |
| rs1053338 | 1 |
| . . . | . . . |

2. If a patient has one or more failed test locus calls (i.e., the analysis was unable to reliably detect either the presence or absence of any risk modifying alleles at the locus), then one may optionally replace missing test locus calls with mean allele copy value.

EXAMPLE

| Test Locus | Genotype Value | Mean Allele Copy Value |
|---|---|---|
| rs10069690 | 0 | 0.53 |
| rs1011970 | 1 | 0.36 |
| rs1045485 | 2 | 0.25 |
| rs10472076 | 0.75 | 0.75 |
| rs1053338 | 1 | 0.29 |
| . . . | . . . | . . . |

3. For each test locus, one may calculate the difference between the observed copies and the mean allele copy value.

EXAMPLE

| Test Locus | Genotype Value | Mean Allele Copy Value | Difference from Mean |
|---|---|---|---|
| rs10069690 | 0 | 0.53 | −0.53 |
| rs1011970 | 1 | 0.36 | 0.64 |
| rs1045485 | 2 | 0.25 | 1.75 |
| rs10472076 | 0.75 | 0.75 | 0 |
| rs1053338 | 1 | 0.29 | 0.71 |
| . . . | . . . | . . . | . . . |

4. For each test, calculate a weighted difference using a coefficient.

EXAMPLE

| Test Locus | Genotype Value | Mean Allele Copy Value | Difference from Mean | Coefficient | Weighted Genotype Value |
|---|---|---|---|---|---|
| rs10069690 | 0 | 0.53 | −0.53 | 0.024 | −0.013 |
| rs1011970 | 1 | 0.36 | 0.64 | 0.049 | 0.031 |
| rs1045485 | 2 | 0.25 | 1.75 | −0.036 | −0.063 |
| rs10472076 | 0.75 | 0.75 | 0 | 0.041 | 0.000 |
| rs1053338 | 1 | 0.29 | 0.71 | 0.077 | 0.055 |
| . . . | . . . | . . . | . . . | . . . | . . . |

5. The test score (e.g., raw test score) may be calculated by summing the weighted genotype values. For this example (if the score were based on only the five test loci shown) the score would be 0.010.

Utilizing a larger number of informative loci can increase the scale of risk increases that are possible, especially since individual loci typically exert very small independent effects. Thus, assume a case where 82 test loci are utilized as described above to yield a test score of 0.10 (instead of the 0.010 yielded by using only five test loci). Using Formula (I) above, if the subject's clinical score was 0.19 (e.g., a Tyrer-Cuzick risk estimation of 19%) and C was set at 0.77, then the combined test (or risk score or percent probability of developing cancer) would be $RRS=1-(1-[0.19])^{exp(0.77*[0.10])}=0.204$ or 20.4%. This could be important for the subject since many medical societies set the cut-off at which increased surveillance (e.g., early mammograms, breast MRI, etc.) at 20%.

6. If any test loci were failed, then one may optionally perform a 'failure check' for the test score. This may involve calculating the "riskiest" and "least risky" scores that might possibly have been observed if there had been no failures. One may let $test\_score_{max}$ denote the riskiest possible score, and let $test\_score_{min}$ denote the least risky score.

To calculate $PRS_{max}$,
Plug in 2 copies for any failed test locus with a coefficient >0.
Plug in zero copies for any failed test locus with a coefficient <0.
In this example, $test\_score_{max}$ is 0.062.

EXAMPLE

| Test Locus | Genotype Value | Mean Allele Copy Value | Difference from Mean | Coefficient | Weighted Genotype Value |
|---|---|---|---|---|---|
| rs10069690 | 0 | 0.53 | −0.53 | 0.024 | −0.013 |
| rs1011970 | 1 | 0.36 | 0.64 | 0.049 | 0.031 |
| rs1045485 | 2 | 0.25 | 1.75 | −0.036 | −0.063 |
| rs10472076 | 2 | 0.75 | 1.25 | 0.041 | 0.051 |
| rs1053338 | 1 | 0.29 | 0.71 | 0.077 | 0.055 |
| . . . | . . . | . . . | . . . | . . . | . . . |

To calculate $test\_score_{min}$,
Plug in 2 copies for any failed test locus with a coefficient <0.
Plug in zero copies for any failed test locus with a coefficient >0.
In this example, $PRS_{min}$ is −0.020

EXAMPLE

| Test Locus | Genotype Value | Mean Allele Copy Value | Difference from Mean | Coefficient | Weighted Genotype Value |
|---|---|---|---|---|---|
| rs10069690 | 0 | 0.53 | −0.53 | 0.024 | −0.013 |
| rs1011970 | 1 | 0.36 | 0.64 | 0.049 | 0.031 |
| rs1045485 | 2 | 0.25 | 1.75 | −0.036 | −0.063 |
| rs10472076 | 0 | 0.75 | −0.75 | 0.041 | −0.031 |
| rs1053338 | 1 | 0.29 | 0.71 | 0.077 | 0.055 |
| . . . | . . . | . . . | . . . | . . . | . . . |

7. The test score may optionally be failed (disregarded, deemed invalid or not reliably indicating risk) for the subject if the risks associated with $test\_score_{max}$ or $test\_score_{min}$ differ from the test score risk by more than 10%. To check this, one may take the exponential function $(exp(x)=2.718^x)$ of each of the 3 scores. Thus, one may fail the test score if either of the following is true:

$exp(test\_score_{max}) \geq exp(test\ score)+0.1*exp(test\ score)$ $exp(test\_score_{min}) \leq exp(test\ score)-0.1*exp(test\ score)$ Another way one may fail the test score is if either of the following is true:

$exp(C1*test\_score_{max})>exp(C1*test\_score)+0.1*exp(C1*test\_score)$ $exp(C1*test\_score_{min})<exp(C1*test\_score)-0.1*exp(C1*test\_score)$ In some embodiments determining (or estimating or calculating) the subject's risk for developing cancer comprises determining (or estimating or calculating) the subject's risk for developing cancer attributable or allocable to the detected or determined genotypes. Embodiments where determining (or estimating) the subject's risk for developing cancer comprises combining the subject's risk for developing cancer attributable or allocable to the detected genotypes with a clinical risk assessment or other risk factors, calculations, scores, or estimations to yield a composite risk score or estimation. Thus, some embodiments further comprise performing a clinical risk assessment. In some such embodiments the clinical risk assessment comprises obtaining information from the subject on one or more of the following: medical history of breast cancer, ductal carcinoma or lobular carcinoma, age, age of first menstrual period, age at which the subject first gave birth, family history of breast cancer, results of previous breast biopsies, breast density, and race/ethnicity. In related embodiments, calculating a test score incorporating the genotypes detected in (1) and the clinical characteristic(s) evaluated in (2) comprises calculating a clinical score as described above. In some embodiments the clinical score is based at least in part on phenotypic risk factors including age, family history, reproductive history, and benign breast disease. In some embodiments the clinical score is calculated using: a Gail Model, a Claus Model, Claus Tables, BOADICEA, a Jonker Model, a Claus Extended Formula, a Tyrer-Cuzick Model, BRCAPRO, or a Manchester Scoring System. In some such embodiments the clinical score is a score or risk estimation calculated using a Tyrer-Cuzick Model (e.g., Tyrer-Cuzick version 7 or version 8).

In some embodiments such determining comprises determining whether the subject's probability of developing cancer exceeds some reference probability. In some such embodiments, such determining comprises comparing the test score to a reference score or probability. In some embodiments determining that the subject's probability of developing cancer exceeds some reference probability comprises calculating a test score incorporating the genotypes detected in (1) and calculating (or estimating) the subject's percent probability of developing cancer based at least in part on such test score exceeding some reference score. In some such embodiments such reference score corresponds to at least a 15%, 20%, 25%, 30%, 35%, 40%, 50%, 60%, 70%, 80%, 90% or greater probability of developing cancer.

In some embodiments of each aspect of the present disclosure the subject lacks or has been determined to not harbor a pathogenic variant in one or more genes. Some embodiments of the present disclosure further comprise (preferably before or concurrently with step (1) of the above-described methods) determining whether the patient harbors a pathogenic variant in one or more genes. In some embodiments one or more specimens is analyzed for both variants in such genes and to detect the genotype for the test loci and the determination of risk attributable or allocable to such genotypes is performed only if the patient is determined to not harbor any variants in such genes. In some embodiments determining whether the patient harbors a pathogenic variant in such genes comprises sequencing such genes (e.g., sequencing the coding portions of such genes). In some embodiments such sequencing is performed on the same sample as the genotype analysis while in other embodiments the sequencing is performed on another sample. In some embodiments such sequencing is performed using a next-generation sequencing technique.

In some embodiments such genes are one, a panel of, or all known cancer predisposition genes. In some embodiments such genes are one, a panel of, or all known moderate or high penetrance cancer predisposition genes. In some embodiments such genes are one, a panel of, or all known high penetrance cancer predisposition genes. In some embodiments a moderate penetrance cancer predisposition gene is a gene in which pathogenic variants have been shown in a peer-reviewed publication to increase a subject's risk of developing at least one cancer at least 2- or 3-fold over the average risk in a reference population. In some embodiments a high penetrance cancer predisposition gene is a gene in which pathogenic variants have been shown in a peer-reviewed publication to confer a risk of at least 25%, 30%, 35%, 40%, 45%, 50%, 60%, 70%, 80%, or 90% of developing at least one cancer. In some embodiments of each aspect of the present disclosure the subject lacks or has been determined to not harbor a pathogenic variant in one or more genes or gene panels in Table 3 (i.e., any genes or panels in any of Tables 3A, 3B, 3C, or 3D).

TABLE 3A

| Gene # | Panel B | Panel C | Panel D | Panel E | Panel F | Panel G |
|---|---|---|---|---|---|---|
| 1 | BRCA1 | BRCA1 | BRCA1 | MLH1 | BRCA1 | BRCA1 |
| 2 | BRCA2 | BRCA2 | BRCA2 | MSH2 | BRCA2 | BRCA2 |
| 3 | MLH1 | MLH1 | CHEK2 | MSH6 | MLH1 | MLH1 |
| 4 | MSH2 | MSH2 | ATM | PMS2 | MSH2 | MSH2 |
| 5 | MSH6 | MSH6 | NBN | BRCA1 | MSH6 | MSH6 |
| 6 | PMS2 | PMS2 | PALB2 | BRCA2 | PMS2 | PMS2 |
| 7 | EPCAM | EPCAM | BARD1 | ATM | EPCAM | EPCAM |
| 8 | MUTYH | MUTYH | BRIP1 | BARD1 | APC | APC |
| 9 | APC | APC | PMS2 | BRIP1 | MUTYH | MUTYH |
| 10 | CDKN2A | CDKN2A | MSH2 | CHEK2 | PALB2 | PALB2 |
| 11 | PALB2 | PALB2 | MSH6 | MUTYH | CDKN2A | CHEK2 |
| 12 | SMAD4 | SMAD4 | TP53 | RAD50 | CDK4 | PTEN |
| 13 | BMPR1A | BMPR1A | MUTYH | EPCAM* | TP53 | STK11 |
| 14 | TP53 | TP53 | | | PTEN | CDH1 |
| 15 | PTEN | PTEN | | | CDH1 | TP53 |
| 16 | STK11 | STK11 | | | STK11 | ATM |
| 17 | CDH1 | CDH1 | | | SMAD4 | RAD51C |
| 18 | NBN1 | NBN1 | | | BMPR1A | RAD51D |
| 19 | CHEK2 | CHEK2 | | | ATM | BRIP1 |
| 20 | RAD51C | RAD51C | | | CHEK2 | BARD1 |
| 21 | RAD51D | RAD51D | | | RAD51C | BMPR1A |
| 22 | BRIP1 | BRIP1 | | | RAD51D | SMAD4 |
| 23 | BARD1 | BARD1 | | | MLH3 | CDKN2A |
| 24 | ATM | ATM | | | BRIP1 | CDK4 |
| 25 | CDK4 | CDK4 | | | BARD1 | RAD50 |

TABLE 3A-continued

| Gene # | Panel B | Panel C | Panel D | Panel E | Panel F | Panel G |
|---|---|---|---|---|---|---|
| 26 | | RAD50* | | | NSB1 | NBN |
| 27 | | MRE11A* | | | RAD50 | MRE11 |
| 28 | | MLH3* | | | MRE11A | MLH3 |
| 29 | | MITF* | | | HOXB13* | |
| 30 | | ELAC2* | | | | |

*Optional in this panel

TABLE 3B

Panels H to N

| Gene # | Panel H | Panel I | Panel J | Panel K | Panel L | Panel M | Panel N |
|---|---|---|---|---|---|---|---|
| 1 | APC | ATM | APC | BLM | ATR | BRCA1 | BRCA1 |
| 2 | BRCA1 | BMPR1A | ATM | CEBPA | BARD1 | BRCA2 | BRCA2 |
| 3 | BRCA2 | CDH1 | BMPR1A | FLCN | BRAF | MLH1 | MLH1 |
| 4 | CDKN2A | CDK4 | BRCA1 | MEN1 | BRIP1 | MSH2 | MSH2 |
| 5 | EPCAM | CHEK2 | BRCA2 | PTCH | FANCA | MSH6 | MSH6 |
| 6 | MLH1 | HOXB13 | CDH1 | RET | FANCB | PMS2 | PMS2 |
| 7 | MSH2 | TP53 | CDK4 | SDHAF2 | FANCC | EPCAM | EPCAM |
| 8 | MSH6 | PTEN | CDKN2A | SDHB | FANCD2 | MUTYH | MUTYH |
| 9 | MUTYH | SMAD4 | CHEK2 | SDHC | FANCE | APC | APC |
| 10 | PALB2 | STK11 | EPCAM | SDHD | FANCF | CDKN2A | CDKN2A |
| 11 | PMS2 | | MLH1 | TMEM127 | FANCG | PALB2 | PALB2 |
| 12 | | | MSH2 | VHL | FANCI | SMAD4 | SMAD4 |
| 13 | | | MSH6 | | FANCL | BMPR1A | BMPR1A |
| 14 | | | MUTYH | | FANCM | TP53 | TP53 |
| 15 | | | TP53 | | KRAS | PTEN | PTEN |
| 16 | | | PALB2 | | MLH3 | STK11 | STK11 |
| 17 | | | PMS2 | | MRE11 | CDH1 | CDH1 |
| 18 | | | PTEN | | NBS1 | NBN1 | NBN1 |
| 19 | | | SMAD4 | | PIK3CA | CHEK2 | CHEK2 |
| 20 | | | STK11 | | PMS1 | RAD51C | RAD51C |
| 21 | | | | | RAD50 | RAD51D | RAD51D |
| 22 | | | | | RAD51C | BRIP1 | BRIP1 |
| 23 | | | | | | BARD1 | BARD1 |
| 24 | | | | | | ATM | ATM |
| 25 | | | | | | CDK4 | CDK4 |
| 26 | | | | | | | MITF |
| 27 | | | | | | | ELAC2 |

TABLE 3C

Panel O

| Gene # | Gene Symbol |
|---|---|
| 1 | BRCA1 |
| 2 | BRCA2 |
| 3 | MLH1 |
| 4 | MSH2 |
| 5 | PMS2 |
| 6 | MLH3 |
| 7 | EPCAM |
| 8 | MSH6 |
| 9 | APC |
| 10 | PMS1 |
| 11 | PTEN |
| 12 | STK11 |
| 13 | RET |
| 14 | SDHD |
| 15 | SDHC |
| 16 | SDHB |
| 17 | SDHAF2 |
| 18 | CDH1 |
| 19 | MUTYH |
| 20 | SMAD4 |
| 21 | MEN1 |

TABLE 3C-continued

Panel O

| Gene # | Gene Symbol |
|---|---|
| 22 | VHL |
| 23 | BMPR1A |
| 24 | PALB2 |
| 25 | TP53 |
| 26 | FANCL |
| 27 | BLM |
| 28 | CDK4 |
| 29 | CDKN2A |
| 30 | ATM |
| 31 | PTCH1 |
| 32 | CHEK2 |
| 33 | RAD51C |
| 34 | CEBPA |
| 35 | NBS1 |
| 36 | FANCA |
| 37 | FANCC |
| 38 | FANCD2 |
| 39 | FANCE |
| 40 | FANCG |
| 41 | FANCI |
| 42 | FANCM |

TABLE 3C-continued

| Panel O | |
|---|---|
| Gene # | Gene Symbol |
| 43 | RAD51D |
| 44 | FANCF |
| 45 | FANCB |
| 46 | BARD1 |
| 47 | RAD50 |
| 48 | MRE11 |
| 49 | BRIP1 |
| 50 | FLCN |
| 51 | TMEM127 |
| 52 | PIK3CA |
| 53 | KRAS |
| 54 | BRAF |
| 55 | HOXB13 |
| 56 | ATR |
| 57 | BAP1 |
| 58 | CFTR |
| 59 | CTRC |
| 60 | FGFR2 |
| 61 | FH |
| 62 | HRAS |
| 63 | KITLG |
| 64 | NF1 |
| 65 | NF2 |
| 66 | PRSS1 |
| 67 | RB1 |
| 68 | SPINK1 |
| 69 | TGFB2 |

TABLE 3D

| Panel P | |
|---|---|
| Gene # | Gene Symbol |
| 1 | BRCA1 |
| 2 | BRCA2 |
| 3 | MLH1 |
| 4 | MSH2 |
| 5 | MSH6 |
| 6 | PMS2 |
| 7 | EPCAM |
| 8 | APC |
| 9 | MUTYH |
| 10 | PALB2 |
| 11 | CDKN2A |
| 12 | CDK4 |
| 13 | TP53 |
| 14 | PTEN |
| 15 | CDH1 |
| 16 | STK11 |
| 17 | SMAD4 |
| 18 | BMPR1A |
| 19 | ATM |
| 20 | CHEK2 |
| 21 | RAD51C |
| 22 | RAD51D |
| 23 | MLH3 |
| 24 | VHL |
| 25 | MEN1 |
| 26 | RET |
| 27 | NF1 |
| 28 | NF2 |
| 29 | RB1 |
| 30 | PTCH1 |
| 31 | FH |
| 32 | BLM |
| 33 | CEBPA |
| 34 | FLCN |
| 35 | SDHB |
| 36 | SDHC |
| 37 | SDHD |

TABLE 3D-continued

| Panel P | |
|---|---|
| Gene # | Gene Symbol |
| 38 | SDHAF2 |
| 39 | TMEM127 |
| 40 | CFTR |
| 41 | PRSS1 |
| 42 | CTRC |
| 43 | SPINK1 |
| 44 | KRAS |
| 45 | BRIP1 |
| 46 | BARD1 |
| 47 | NBS1 |
| 48 | RAD50 |
| 49 | FANCA |
| 50 | FANCB |
| 51 | FANCC |
| 52 | FANCD2 |
| 53 | FANCE |
| 54 | FANCF |
| 55 | FANCG |
| 56 | FANCI |
| 57 | FANCL |
| 58 | FANCM |
| 59 | ATR |
| 60 | HRAS |
| 61 | TGFB2 |
| 62 | FGFR2 |
| 63 | BAP1 |
| 64 | KITLG |
| 65 | BRAF |
| 66 | MRE11 |
| 67 | PIK3CA |
| 68 | PMS1 |
| 69 | HOXB13 |

In some embodiments of each of the aspects of the present disclosure determining (or estimating) the subject's risk for developing cancer comprises determining (or estimating) the subject's percent probability of developing cancer within one or more specific periods of time. In some such embodiments, the period(s) of time may be the next five years; a plurality of five-, ten-, 15-, or 20-year intervals; the remainder of the subject's expected lifetime; any time before a specific age (e.g., 50, 55, 60, 65, 70, 75, 80, 85, 90 years of age); etc.

In some embodiments "analyzing a sample of DNA obtained or derived from a subject to detect the subject's genotype for a plurality of genomic loci (e.g., at most X genomic loci) comprising a plurality of test loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the loci listed in Table 1, and/or for one or more of such test genomic locus a locus in linkage disequilibrium with one or more thereof" comprises subjecting the sample to next-generation sequencing. In some such embodiments such sequencing comprises sequencing genomic regions flanking each genomic locus and/or each test locus. In some embodiments such regions include at least 5, 10, 15, 20, 30, 40, 50, 60, 70, 80, 90, 100, 125, 150, 175, 200, 250, 300, 350, 400, 450, or 500 nucleotides on one or both sides of the locus. In some embodiments such analyzing comprises subjecting the sample to microarray analysis. In some such embodiments the microarray comprises probes specific for a plurality of test genomic loci, wherein the plurality consists of at most X genomic loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test genomic locus a locus in linkage disequilibrium with one or more thereof.

In some embodiments of each of the aspects of the present disclosure the risk of developing cancer is determined (or estimated) for breast cancer. In some embodiments the subject has not had any previous cancer. In some embodiments the subject has not had breast cancer, lobular carcinoma or ductal carcinoma.

The risk conferred by any particular test locus may be affected by the ethnicity of the subject. Thus, in some embodiments of each of the aspects of the present disclosure the subject's race is Caucasian.

In some embodiments of each of the aspects of the present disclosure a second locus is in linkage disequilibrium with a first locus (e.g., a test locus in Table 1) if such second locus has linkage disequilibrium above 0.9 or 1.

In some embodiments of each of the aspects of the present disclosure the sample is, or is derived from, a bodily fluid. In some embodiments, the sample is, or is derived from, known or expected germline tissue (e.g., nucleated blood cells, fibroblasts, etc.).

In some embodiments of each of the aspects of the present disclosure screening for breast cancer comprises performing a clinical breast exam, mammogram, breast MRI, or enrolling the subject in a screening breast MRIC and mammography program.

In some embodiments of each of the aspects of the present disclosure a particular treatment modality is administered, recommended or prescribed in a subject whose risk of developing breast cancer (e.g., in the next five years, for the remainder of the subject life expectancy, before a certain age, etc.) is at least 15%, 20%, 25%, 30%, 35%, 40%, 50%, 60%, 70%, 80%, or 90%. In some embodiments the treatment modality is breast cancer screening. In some embodiments the treatment modality is an anti-cancer therapy (e.g., medical management that includes some action meant to prevent cancer). In some embodiments such anti-cancer therapy is administered, recommended or prescribed in a subject whose risk of developing breast cancer over the subsequent five years is greater than about 1.66%. In some embodiments the anti-cancer therapy comprises estrogen receptor therapy.

In some embodiments of each of the above aspects of the present disclosure, "analyzing DNA" can comprise either (a) analyzing (e.g., informatically) DNA data previously obtained from a patient sample or (b) obtaining DNA from a patient sample and performing a laboratory assay to obtain data regarding such DNA. Analogously, "determining the nucleotide sequence of" DNA includes either (a) analyzing (e.g., informatically) DNA sequence data previously obtained from a patient sample or (b) obtaining DNA from a patient sample and performing a laboratory assay to sequence such DNA.

Detection of Test Locus Genotypes

The present disclosure generally relates to the detection of genotypes for test loci. The methodology or technique for preparing nucleic acids in a form that is suitable for genotype detection can include, but are not limited to, PCR, detectable probes, sequencing and single base extensions, reverse transcriptase-PCR (RT-PCR), real-time PCR, allele-specific hybridization, reverse transcription quantitative real-time PCR (RT-qPCR) ligase chain reaction, strand displacement amplification (SDA), self-sustained sequence replication (3SR), or in situ PCR. Exemplary, but non-limiting, techniques for analysis of nucleic acid samples to detect test locus variants are briefly described below. One preferred technique is NGS.

DNA Sequencing and Single Base Extensions

Genotypes can also be detected by direct sequencing. Techniques include e.g., dideoxy sequencing-based methods and other methods such as Maxam and Gilbert sequence (see, e.g., Sambrook et al., supra).

Other detection techniques include Pyrosequencing™ of oligonucleotide-length products. Such techniques often employ amplification techniques such as PCR. For example, in pyrosequencing, a sequencing primer is hybridized to a single stranded, PCR-amplified, DNA template; and incubated with the enzymes, DNA polymerase, ATP sulfurylase, luciferase and apyrase, and the substrates, adenosine 5' phosphosulfate (APS) and luciferin. The first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a Pyrogram™. Each light signal is proportional to the number of nucleotides incorporated. Apyrase, a nucleotide degrading enzyme, continuously degrades unincorporated dNTPs and excess ATP. When degradation is complete, another dNTP is added.

Another similar technique for detecting genotypes does not require use of a complete PCR, but typically uses only the extension of a primer by a single, fluorescence-labeled dideoxyribonucleic acid molecule (ddNTP) that is complementary to the nucleotide to be investigated. The nucleotide at the polymorphic site can be identified via detection of a primer that has been extended by one base and is fluorescently labeled (e.g., Kobayashi et al, *Mol. Cell. Probes,* 9:175-182, 1995).

Distinguishing Test Locus Genotypes

Amplification products can be analyzed using techniques including, without limitation, electrophoretic analysis or sequence analysis. Non-limiting examples of electrophoretic analysis include slab gel electrophoresis such as agarose or polyacrylamide gel electrophoresis, capillary electrophoresis, and denaturing gradient gel electrophoresis (DGGE). Other methods of nucleic acid analysis include, but are limited to, hybridization with allele-specific oligonucleotide probes (Wallace et al., *Nucl. Acids Res.* (1978) 6:3543-3557), including immobilized oligonucleotides (Saiki et al., *PNAS* (1989) 86:6230-6234), oligonucleotide arrays (Maskos and Southern, *Nucl. Acids Res.* (1993) 21:2269-2270), oligonucleotide-ligation assay (OLA) (Landegren et al., *Science* (1988) 241:1077), allele-specific ligation chain reaction (LCR) (Barrany, *PNAS* (1991) 88:189-193), gap-LCR (Abavaya et al. *Nucl. Acids Res.* (1995) 23:675-682), single-strand-conformation-polymorphism detection (Orita et al., *Genomics* (1983) 5:874-879), RNAase cleavage at mismatched base-pairs (Myers et al., *Science* (1985) 230: 1242), genetic bit analysis (GBA) (Nikiforov et al., *Nucl. Acids Res.* (1994) 22:4167-4175), in situ hybridization, denaturing high performance liquid chromatography (DHPLC) (Kim et al., *Genetic Testing* (2008) 12:295-298). Non-limiting examples of sequence analysis include NGS (e.g., Chen et al., *Genome Res.* (2008) 18:1143-1149); Srivatsan et al. *PLOS Genet.* (2008) 4:e1000139), Maxam- Gilbert sequencing, Sanger sequencing, capillary array DNA sequencing, thermal cycle sequencing (Sears et al., *Biotechniques* (1992) 13:626-633), solid-phase sequencing (Zimmerman et al., *Methods Mol. Cell Biol.* (1992) 3:39-42), sequencing with mass spectrometry such as matrix-assisted laser desorption/ionization time-of-flight mass spectrometry (MALDI-TOF/MS; Fu et al., *Nat. Biotechnol.* (1998) 16:381-384), sequencing by hybridization (Chee et al., *Science* (1996) 274:610-614); Drmanac et al., *Science* (1993) 260:1649-1652); Drmanac et al., *Nat. Biotechnol.* (1998) 16:54-58), Polony sequencing (Porreca et al., *Curr. Protoc. Mol. Biol.* (2006) Chp. 7; Unit7.8), ion semiconductor sequencing (Elliott et al., *J. Biomol. Tech.* 1:24-30 (2010), DNA nanoball sequencing (Kaji et al., *Chem. Soc. Rev.* (2010) 39:948-56), single molecule real-time sequencing (Flusberg et al., *Nat. Methods* (2010) 6:461-5), or nanopore DNA sequencing (Wanunu, *Phys. Life Rev.* (2012) 9:125-58)

Allele-Specific Hybridization

This technique, also commonly referred to as allele specific oligonucleotide hybridization (ASO) (e.g., Stoneking et al., AM. J. HUM. GENET. (1991) 48:70-382; Saiki et al., NATURE (1986) 324, 163-166; EP 235,726; and WO/1989/011548), relies on distinguishing between two DNA molecules differing by one base by hybridizing an oligonucleotide probe that is specific for one of the variants to an amplified product obtained from amplifying the nucleic acid sample. This method typically employs short oligonucleotides, e.g., 15-20 bases in length. The probes are designed to differentially hybridize to one variant (e.g., from a reference sequence) versus another. Hybridization conditions should be sufficiently stringent that there is a significant difference in hybridization intensity between alleles, and producing an essentially binary response, whereby a probe hybridizes to only one of the alleles. Some probes are designed to hybridize to a segment of target DNA such that the polymorphic site aligns with a central position (e.g., in a 15-base oligonucleotide at the 7 position; in a 16-based oligonucleotide at either the 8 or 9 position) of the probe, but this design is not required.

The amount and/or presence of an allele is determined by measuring the amount of allele-specific oligonucleotide that is hybridized to the sample. Typically, the oligonucleotide comprises a label (e.g., a fluorescent label). For example, an allele-specific oligonucleotide is applied to immobilized oligonucleotides representing sequences with different nucleotides at the test locus. After stringent hybridization and washing conditions, fluorescence intensity is measured for each variant-specific oligonucleotide.

Suitable assay formats for detecting hybrids formed between probes and target nucleic acid sequences in a sample include, but are not limited to, the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

Detectable Probes

Hybridization probes useful in the methods, systems and kits of the present disclosure can include an allele-specific probe that discriminates between specific alleles of the test locus (e.g., hybridizes to the risk modifying allele but not to the non-risk modifying allele under certain hybridization conditions). The probes can be at least about 12, 15, 16, 18, 20, 22, 24, 25, 30 or more nucleotide fragments of a contiguous sequence surrounding the test locus. The probes can be produced by, for example, chemical synthesis, PCR amplification, generation from longer polynucleotides using restriction enzymes, or other techniques. The probes can be made completely complementary to the target nucleic acid or portion thereof (e.g., to all or a portion of a sequence encoding a target). Therefore, usually high stringency conditions are desirable in order to prevent or at least minimize false positives. However, conditions of high stringency may be best suited to situations where the probes are complementary to regions of the target which lack heterogeneity. The stringency of hybridization is determined by a number of factors during hybridization and during the washing procedure, including temperature, ionic strength, length of time, and concentration of formamide (Sambrook et al. (1989), "Molecular Cloning; A Laboratory Manual," Second Edition (Cold Spring Harbor Press, Cold Spring Harbor, N.Y.)).

Nucleic acid probes, or alternatively nucleic acid from the samples, can be provided in solution for such assays, or can be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

Probes detectable upon a secondary structural change are also suitable for detection of a test locus genotype. Exemplified secondary structure or stem-loop structure probes include molecular beacons or Scorpion® primer/probes. Molecular beacon probes are single-stranded oligonucleic acid probes that can form a hairpin structure in which a fluorophore and a quencher are usually placed on the opposite ends of the oligonucleotide. At either end of the probe short complementary sequences allow for the formation of an intramolecular stem, which enables the fluorophore and the quencher to come into close proximity. The loop portion of the molecular beacon is complementary to a target nucleic acid of interest. Binding of this probe to its target nucleic acid of interest forms a hybrid that forces the stem apart. This causes a conformation change that moves the fluorophore and the quencher away from each other and leads to a more intense fluorescent signal. See, e.g., Tyagi & Kramer, *Nat. Biotechnol.* (1996) 14:303-308; Tyagi et al., *Nat. Biotechnol.* (1998) 16:49-53; Piatek et al., *Nat. Biotechnol.* (1998) 16:359-363; Marras et al., *Genetic Analysis: Biomolecular Engineering* (1999) 14:151-156; Tpp et al, *BioTechniques* (2000) 28:732-738).

Clinical Management

The present disclosure also provides methods of administering, recommending, prescribing, etc. specific treatment modalities to subjects whose risk is determined as disclosed herein. These embodiments of the present disclosure thus will provide patient-specific biological information, which will be informative for treatment modality selection.

Reference Standards for Treatment

In many embodiments, the a patient's risk (or percent probability) of developing cancer is compared to a reference ("reference standard" or "reference level") in order to direct treatment decisions. Such risk can be derived from or embodied in a score. The reference standard used for any embodiment disclosed herein may comprise average, mean, or median scores or risks in a control population. The reference standard may further include an earlier time point for the same subject. For example, a reference standard may include a first time point, and risk can be examined again at second, third, fourth, fifth, sixth time points, etc. Any time point earlier than any particular time point can be considered a reference standard. Because the subject's germline genotype at any test locus is not expected to change over time, however, these time-dependent risks are generally expected to reflect changes in clinical characteristics (e.g., a different Tyrer-Cuzick score due to changed family or personal history). The reference standard may additionally comprise cutoff values or any other statistical attribute of the control population, or earlier time points of the same subject, such as a standard deviation from the mean score or risk. In some embodiments, the control population may comprise healthy individuals, cancer patients having a particular response profile, or the same test patient prior to the administration of any or a specific therapy.

Reference Therapy for Treatment

In some embodiments, a test subject is treated more or less aggressively than a reference therapy based on the difference between the test subject's risk (or genotypes) and the reference risk (or genotypes). In some embodiments a reference therapy is any therapy that is the standard of care for a reference subject of average risk for developing cancer. The standard of care can vary temporally and geographically, and a skilled person can determine the appropriate standard of care by consulting the relevant medical literature.

In some embodiments, a more aggressive therapy than the standard therapy comprises beginning treatment earlier than in the standard therapy. In some embodiments, a more aggressive therapy than the standard therapy comprises administering additional treatments beyond the standard therapy. In some embodiments, a more aggressive therapy than the standard therapy comprises administering alternative treatments instead of the standard therapy. In some embodiments, a more aggressive therapy than the standard therapy comprises treating on an accelerated schedule compared to the standard therapy (e.g., earlier initiation of mammograms or breast MRIs). In one embodiment a more aggressive therapy comprises increased frequency of the administration schedule (e.g., more frequent mammograms or breast MRIs).

Kits

In some aspects and embodiment the present disclosure describes novel kits. In some embodiments the kits of the present disclosure comprise detection reagents packaged together in the form of a kit for conducting any of the assays disclosed herein. In certain embodiments, the kits comprise oligonucleotides capable of specifically detecting one or more test loci genotypes (or alleles) as described herein. The oligonucleotide sequences may correspond to fragments of the biomarker nucleic acids. For example, the oligonucleotides can be more than 200, 200, 150, 100, 50, 25, 10, or fewer than 10 nucleotides in length. The kit can contain in separate containers a solution of nucleic acids, control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay can optionally be included in the kit.

In other embodiments of the present disclosure, the kit can contain a nucleic acid substrate array comprising one or more nucleic acid sequences. Such an array may comprise oligonucleotides capable of specifically detecting one or more test locus genotypes (or alleles) as described herein. In various embodiments, the presence or absence of one or more of the test locus alleles can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, TX), Cyvera (Illumina, San Diego, CA), RayBio Antibody Arrays (RayBiotech, Inc., Norcross, GA), CellCard (Vitra Bioscience, Mountain View, CA) and Quantum Dots' Mosaic (Invitrogen, Carlsbad, CA).

Systems, Computer-Related and Computer-Implemented Aspects of the Disclosure

The results of any analyses according to the disclosure will often be communicated to physicians, genetic counselors and/or patients (or other interested parties such as researchers) in a transmittable form that can be communicated or transmitted to any of the above parties. Such a form can vary and can be tangible or intangible (e.g., electronic). The results can be embodied in descriptive statements, diagrams, photographs, charts, images or any other visual forms. For example, graphs showing expression or activity level or sequence variation information for various genes can be used in explaining the results. Diagrams showing such information for additional target gene(s) are also useful in indicating some testing results. The statements and visual forms can be recorded on a tangible medium such as papers, computer readable media such as floppy disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when a sequencing (or genotyping) assay is conducted outside the United States, the information and data on a test result may be generated, cast in a transmittable form as described above, and then imported into the United States. Accordingly, the present disclosure also encompasses methods and systems for producing a transmittable form of sequence information for at least one patient sample. The method comprises the steps of (1) sequencing nucleic acids in a sample according to methods of the present disclosure; and (2) embodying the result of the sequencing step in a transmittable form. The transmittable form is a product of such a method.

Techniques for analyzing sequence data (indeed any data obtained according to the disclosure) may be implemented using hardware, software or a combination thereof in one or more computer systems or other processing systems capable of effectuating such analysis.

The sample analyzer in the systems of the disclosure can be any instrument useful in sequencing nucleic acids, including but not limited to, Illumina HiSeq™, Ion Torrent PGM, ABI SOLiD™ sequencer, PacBio RS, Helicos Heliscope™, or any instrument utilizing a sequencing system discussed above.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the Macintosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present disclosure relates to a computer program product comprising a computer-usable medium having computer-readable program codes or instructions embodied thereon for enabling a processor to carry out gene status analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Figure 4:
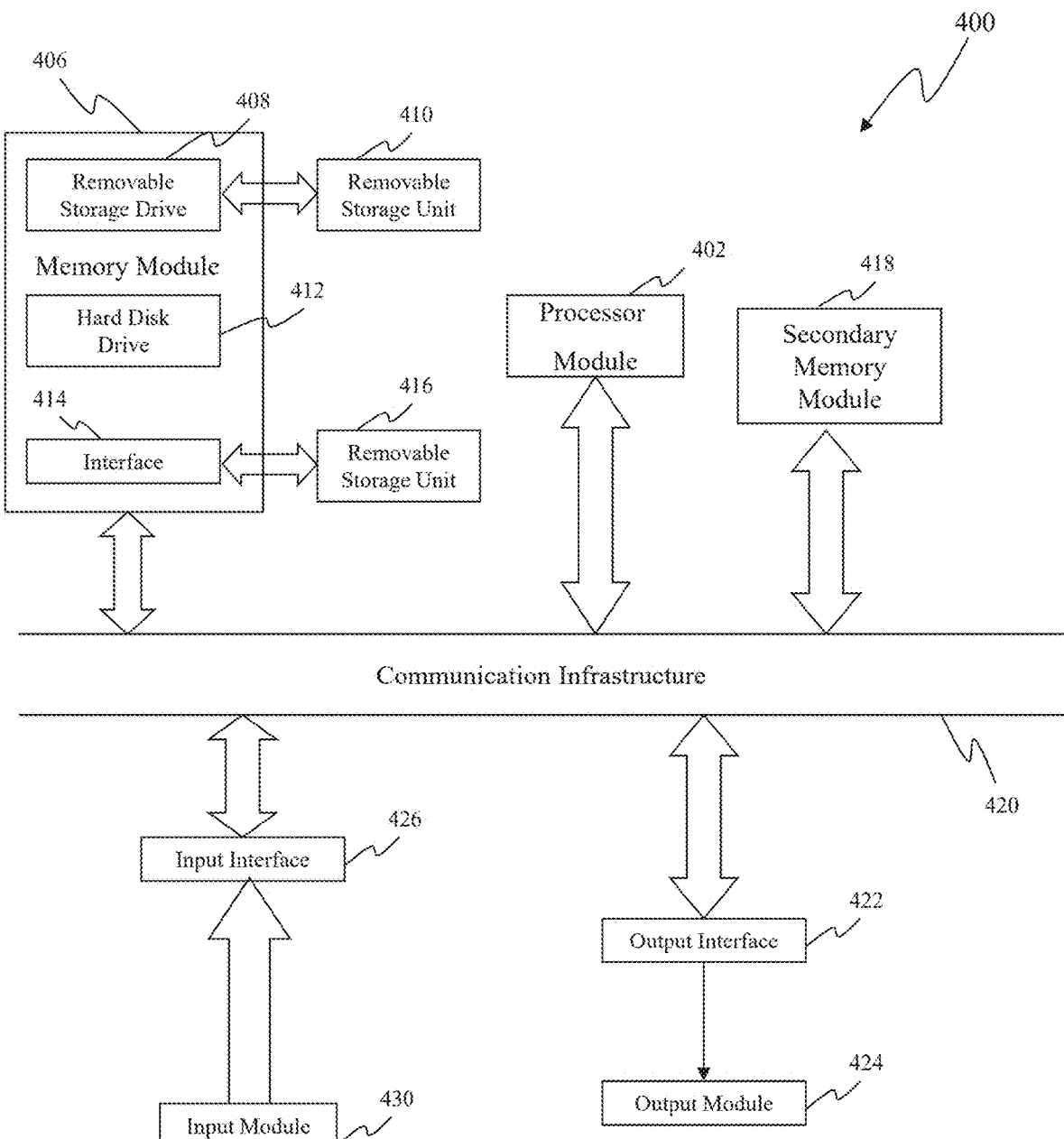
FIG. 4 is an illustration of an example of a system useful in certain aspects and embodiments of the invention.

One example of a computer system of the disclosure is the computer system [400] illustrated in FIG. 4. Computer system may include at least one input module for entering patient data into the computer system [400]. The computer system [400] may include at least one output module [424] for indicating whether a patient has an increased or decreased likelihood of response and/or indicating suggested treatments determined by the computer system [400]. Computer system [400] may include at least one memory module [406] in communication with the at least one input module [430] and the at least one output module [424].

The at least one memory module [406] may include, e.g., a removable storage drive [408], which can be in various forms, including but not limited to, a magnetic tape drive, a floppy disk drive, a VCD drive, a DVD drive, an optical disk drive, etc. The removable storage drive [408] may be compatible with a removable storage unit [410] such that it can read from and/or write to the removable storage unit [410]. Removable storage unit [410] may include a computer usable storage medium having stored therein computer-readable program codes or instructions and/or computer readable data. For example, removable storage unit [410] may store patient data. Example of removable storage unit [410] are well known in the art, including, but not limited to, floppy disks, magnetic tapes, optical disks, and the like. The at least one memory module [406] may also include a hard disk drive [412], which can be used to store computer readable program codes or instructions, and/or computer readable data.

Figure 2:
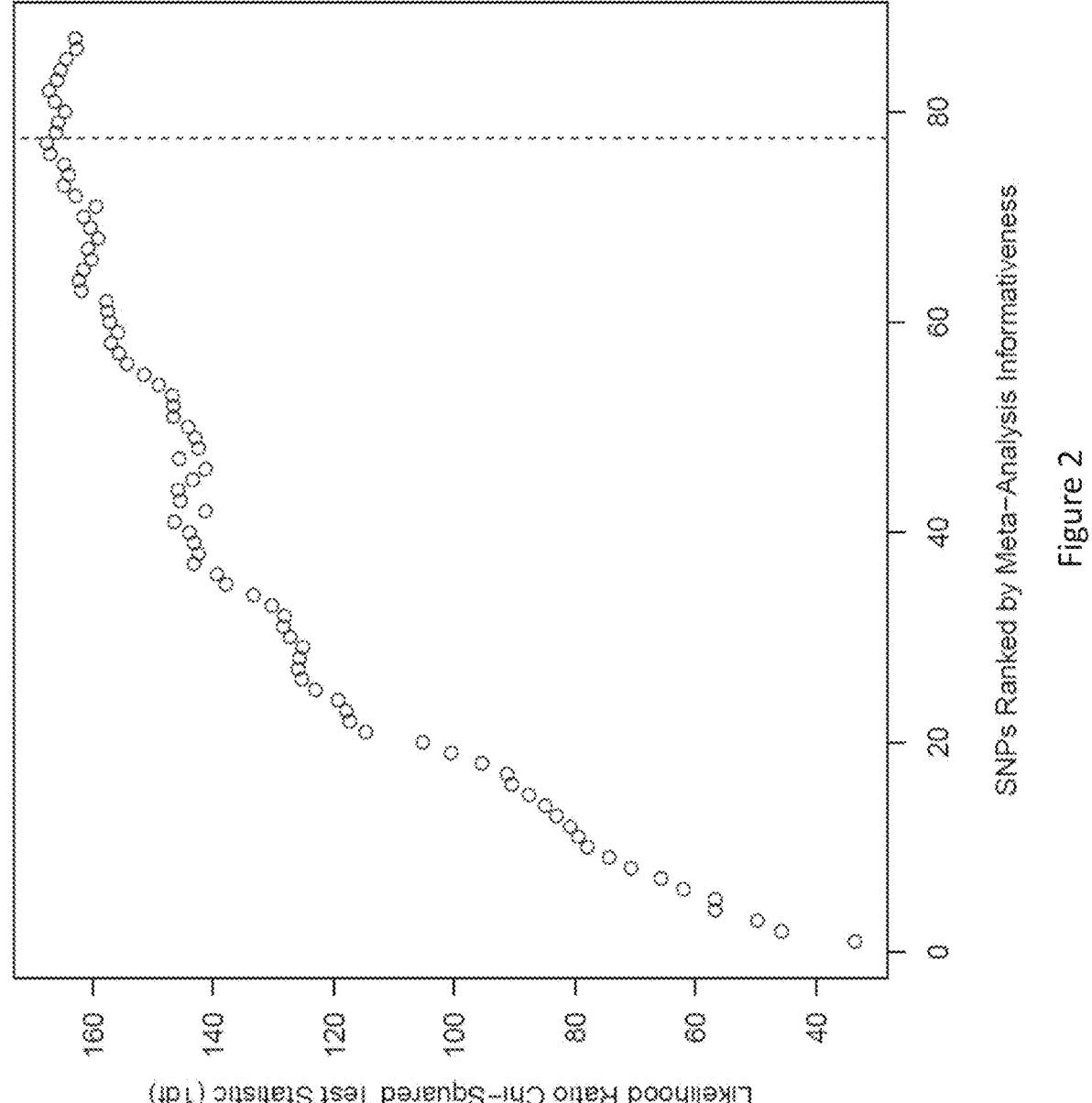
FIG. 2 shows the 82 most informative test loci (SNPs) that yielded the maximum of the likelihood ratios.

In addition, as shown in FIG. 2, the at least one memory module [406] may further include an interface [414] and a removable storage unit [416] that is compatible with interface [414] such that software, computer readable codes or instructions can be transferred from the removable storage unit [416] into computer system [400]. Examples of interface and removable storage unit [416] pairs include, e.g., removable memory chips (e.g., EPROMs or PROMs) and sockets associated therewith, program cartridges and cartridge interface, and the like. Computer system [400] may also include a secondary memory module [418], such as random access memory (RAM).

Computer system [400] may include at least one processor module [402]. It should be understood that the at least one processor module [402] may consist of any number of devices. The at least one processor module [402] may include a data processing device, such as a microprocessor or microcontroller or a central processing unit. The at least one processor module [402] may include another logic device such as a DMA (Direct Memory Access) processor, an integrated communication processor device, a custom VLSI (Very Large Scale Integration) device or an ASIC (Application Specific Integrated Circuit) device. In addition, the at least one processor module [402] may include any other type of analog or digital circuitry that is designed to perform the processing functions described herein.

As shown in FIG. 4, in computer system [400], the at least one memory module [404], the at least one processor module [402], and secondary memory module [418] are all operably linked together through communication infrastructure [420], which may be a communications bus, system board, cross-bar, etc.). Through the communication infrastructure [420], computer program codes or instructions or computer readable data can be transferred and exchanged. Input interface [426] may operably connect the at least one input module to the communication infrastructure [420]. Likewise, output interface [422] may operably connect the at least one output module [424] to the communication infrastructure [420].

The at least one input module [430] may include, for example, a keyboard, mouse, touch screen, scanner, and other input devices known in the art. The at least one output module [424] may include, for example, a display screen, such as a computer monitor, TV monitor, or the touch screen of the at least one input module [430]; a printer; and audio speakers. Computer system [400] may also include, modems, communication ports, network cards such as Ethernet cards, and newly developed devices for accessing intranets or the internet.

The at least one memory module [406] may be configured for storing patient data entered via the at least one input module [430] and processed via the at least one processor module [402]. Patient data relevant to the present disclosure may include sequence or variant information for one or more of the genes in any of Panels A-Y. Patient data relevant to the present disclosure may also include clinical parameters relevant to the patient (e.g., age, lifestyle and environmental risk factors for cancer, previously diagnosed diseases (including previously diagnosed cancers), tumor size, node status, tumor stage). Any patient data a physician might find useful in making treatment decisions/recommendations may also be entered into the system, including but not limited to age, gender, and race/ethnicity and lifestyle data such as diet information. Other possible types of patient data include symptoms currently or previously experienced, patient's history of illnesses, medications, and medical procedures.

The at least one memory module [406] may include a computer-implemented method stored therein. The at least one processor module [402] may be used to execute software or computer-readable instruction codes of the computer-implemented method. The computer-implemented method may be configured to, based upon the patient data, indicate whether the patient has an increased likelihood of recurrence, progression or response to any particular treatment, generate a list of possible treatments, etc.

In certain embodiments, the computer-implemented method may be configured to identify a patient as having or not having an increased risk of a particular cancer. For example, the computer-implemented method may be configured to inform a physician that a particular patient has an increased risk of a particular cancer. Alternatively or additionally, the computer-implemented method may be configured to actually suggest a particular course of treatment based on the answers to/results for various queries.

Figure 5:
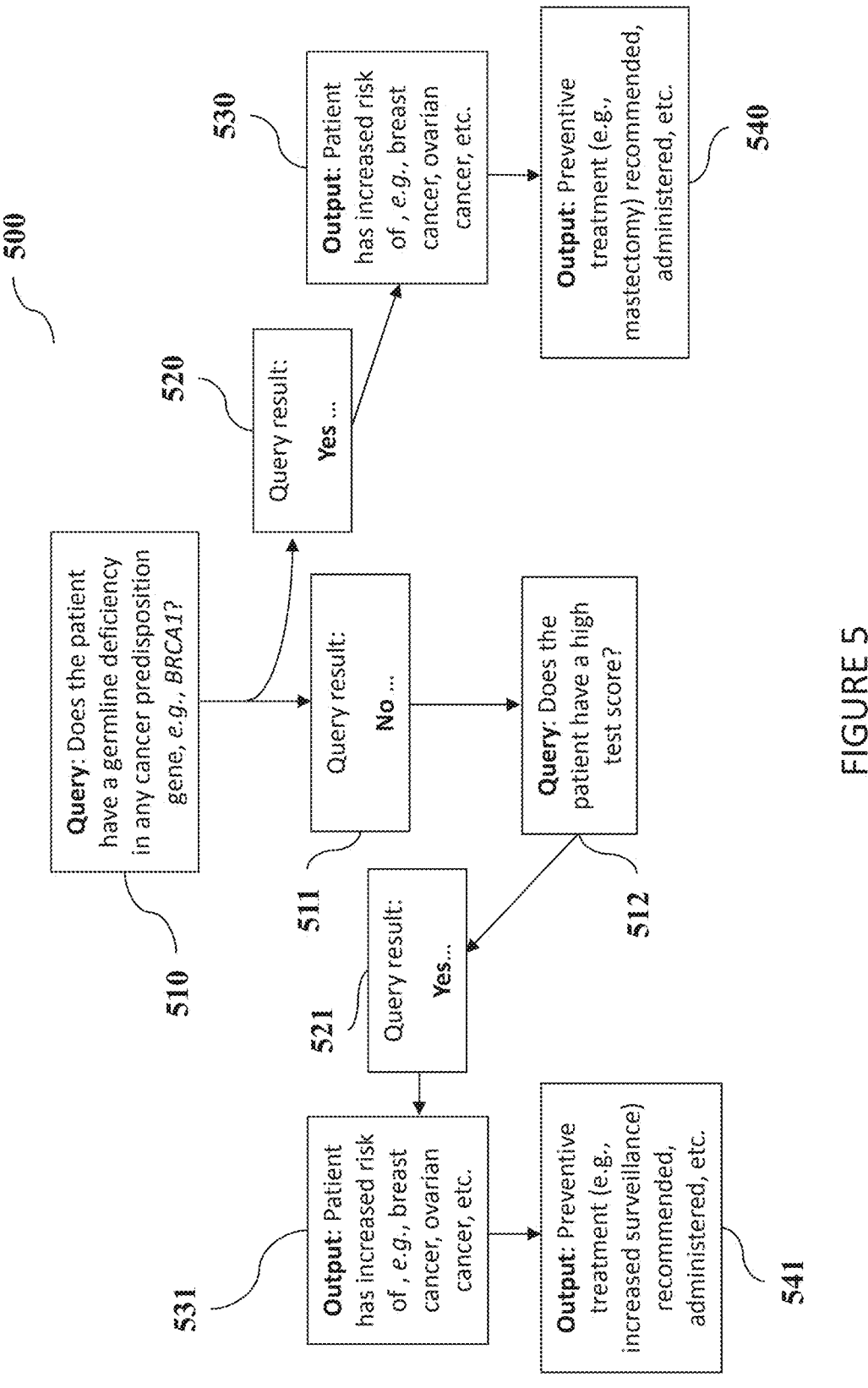
FIG. 5 is a flowchart illustrating an example of a computer-implemented method of the invention.

FIG. 5 illustrates one embodiment of a computer-implemented method [500] of the disclosure that may be implemented with the computer system [400] of the disclosure. The method begins with a query [510]. If the answer to/result for this query is "Yes" [520], then the method may diagnose [530] the patient as having an increased risk of a particular cancer (e.g., breast cancer if there is a germline deficiency in BRCA1). If the answer to/result for this query is "No" [511], then the method may perform another query [512]. If the answer to/result for this query is "Yes" [521], then the method may diagnose [531] the patient as having an increased risk of cancer. The method [500] may then proceed with more queries, make a particular treatment recommendation ([540], [541]), or simply end.

Though the queries are performed sequentially as suggested in FIG. 5, the laboratory analysis that provides data to answer these queries may be performed in any suitable order. Optionally, the method may query clinical parameters (e.g., age of menarche) before or after querying any of the molecular characteristics of cancer predisposition genes or test locus genotypes as shown. As mentioned above, the preceding order of queries may be modified. In some embodiments an answer of "yes" to one query (e.g., [510]) prompts one or more of the remaining queries to confirm that the patient has, e.g., increased risk of developing cancer.

In some embodiments, the computer-implemented method of the disclosure is open-ended. In other words, the apparent first step [510] in FIG. 5 may actually form part of a larger process and, within this larger process, need not be the first step/query. Additional steps may also be added onto the core methods discussed above. These additional steps include, but are not limited to, informing a health care professional (or the patient itself) of the diagnosis reached; combining the conclusion reached by the illustrated method [500] with other facts or conclusions to reach some additional or refined conclusion regarding the patient's diagnosis, prognosis, treatment, etc.; making a recommendation for treatment (e.g., "patient should/should not undergo earlier mammogram"); additional queries about additional biomarkers, clinical parameters, or other useful patient information (e.g., age, general patient health, etc.).

Regarding the above computer-implemented method [500], the answers to the queries may be determined by the method instituting a search of patient data for the answer. For example, to answer the respective queries ([510], [512]), patient data may be searched for germline sequence data for the cancer predisposition genes to be analyzed (e.g., two or more of the genes in Panel B or Panel N) and/or for genotype data for the test loci to be analyzed. The queries may be performed in no particular order or according to some desired order. If such a comparison has not already been performed, the method may compare these data to some reference (e.g., reference sequence) in order to determine if the patient has a germline deficiency in any of the cancer predisposition genes being analyzed. Additionally or alternatively, the method may present one or more of the queries ([510], [512]) to a user of the computer system [400] (e.g., a physician). For example, the questions ([510], [512]) may be presented via an output module [424]. The user may then answer "Yes" or "No" or provide some other value (e.g., test score) via an input module [430]. The method may then proceed based upon the answer received. Likewise, the conclusions ([530], [531]) may be presented to a user of the computer-implemented method via an output module [424].

The practice of the present disclosure may also employ conventional biology methods, software and systems. Computer software products of the disclosure typically include computer readable media having computer-executable instructions for performing the logic steps of the method of the disclosure. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., INTRODUCTION TO COMPUTATIONAL BIOLOGY METHODS (PWS Publishing Company, Boston, 1997); Salzberg et al. (Ed.), COMPUTATIONAL METHODS IN MOLECULAR BIOLOGY, (Elsevier, Amsterdam, 1998); Rashidi & Buehler, BIOINFORMATICS BASICS: APPLICATION IN BIOLOGICAL SCIENCE AND MEDICINE (CRC Press, London, 2000); and Ouelette & Bzevanis, BIOINFORMATICS: A PRACTICAL GUIDE FOR ANALYSIS OF GENE AND PROTEINS (Wiley & Sons, Inc., $2^{nd}$ ed., 2001); see also, U.S. Pat. No. 6,420,108.

The present disclosure may also make use of various computer program products and software for a variety of purposes, such as probe design, management of data, analysis, and instrument operation. See U.S. Pat. Nos. 5,593,839; 5,795,716; 5,733,729; 5,974,164; 6,066,454; 6,090,555; 6,185,561; 6,188,783; 6,223,127; 6,229,911 and 6,308,170. Additionally, the present disclosure may have embodiments that include methods for providing genetic information over networks such as the Internet as shown in U.S. Ser. No. 10/197,621 (U.S. Pub. No. 20030097222); Ser. No. 10/063, 559 (U.S. Pub. No. 20020183936), Ser. No. 10/065,856 (U.S. Pub. No. 20030100995); Ser. No. 10/065,868 (U.S. Pub. No. 20030120432); Ser. No. 10/423,403 (U.S. Pub. No. 20040049354).

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information or data relating to mutation load of a patient or population over time. Data comprising the presence of test locus variants can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices. The computer can be, for example, a personal computer, a microcomputer, or a workstation of conventional design.

The computer programs can be implemented in a high-level procedural or object-oriented programming language, to communicate with a computer system. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present disclosure can be considered to be implemented as a computer-readable storage medium, configured with a computer program, where the storage medium causes a computer to operate in a specific manner to perform various functions, as described herein.

The assays disclosed herein can be used to generate a "genotype profile." The test genotype profile can then be compared to a reference genotype profile. The biomarker profiles, reference and test, of embodiments of the present disclosure can be contained in a machine-readable medium, such as analog tapes like those readable by a CD-ROM or USB flash media, among others. The machine-readable media can also comprise subject information; e.g., the subject's medical or family history.

ADDITIONAL EMBODIMENTS

Embodiment 1. A method for genotyping a subject comprising: analyzing a sample of DNA obtained or derived from the subject to detect the genotype for a plurality of genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test locus a locus in linkage disequilibrium with one or more thereof.

Embodiment 2. A method for assessing risk for developing cancer comprising:
(1) analyzing a sample of DNA obtained or derived from a subject to detect the subject's genotype for a plurality of genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the test loci listed in Table 1, and/or for one or more of such test locus a locus in linkage disequilibrium with one or more thereof;
(2) determining (or estimating) the subject's risk for developing cancer based at least in part on the genotypes detected in (2).

Embodiment 3. A method for assessing risk for developing cancer comprising:
(1) analyzing a sample of DNA obtained or derived from a subject to detect the subject's genotype for a plurality of genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the test loci listed in Table 1, and/or for one or more of such test locus a locus in linkage disequilibrium with one or more thereof;
(2) calculating a test score incorporating (or derived from) the genotypes detected in (1); and
(3)(a) diagnosing a subject for whom the score in (2) exceeds a reference score as having a test likelihood of developing cancer that is higher than a reference likelihood of developing cancer; or
(3)(b) diagnosing a subject for whom the score in (2) does not exceed a reference score as having a test likelihood of developing cancer that is equal to or lower than a reference likelihood of developing cancer.

Embodiment 4. A method for treating a subject comprising:
(1) determining the subject's genotype for a plurality of genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the test loci listed in Table 1, and/or for one or more of such test locus a locus in linkage disequilibrium with one or more thereof;
(2) determining (or estimating) the subject's risk for developing cancer based at least in part on the genotypes determined in (1);
(3) prescribing or administering one or more treatment modalities indicated based at least in part on the risk determined (or estimated) in (2).

Embodiment 5. A kit for genotyping a subject comprising: a compartmentalized container; reagents for analyzing a sample of DNA obtained or derived from the subject to detect the genotype for a plurality of genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test genomic locus a locus in linkage disequilibrium with one or more thereof; and instructions for use of the reagents.

Embodiment 6. A system for assessing risk for genotyping a subject, comprising:
(1) a sample analyzer for analyzing DNA in, extracted from or derived from a sample of the subject to detect the subject's genotype for a plurality of genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the test loci listed in Table 1, and/or for one or more of such test locus a locus in linkage disequilibrium with one or more thereof, wherein the sample analyzer contains (a) the sample, (b) genomic DNA from the sample, (c) transcript RNA from the sample, or (d) DNA derived (e.g., synthesized or amplified) from said genomic DNA; and
(2) one or more computer programs for performing any one, all, or any combination of the following functions: (a) a computer program for querying the subject's genotype data; (b) calculating the subject's risk for developing cancer based at least on the subject's genotype data; (c) calculating a test score based on or derived from the subject's genotype data; (d) comparing the test score to one or more reference scores; (e) concluding whether there is an increased risk of cancer based at least in part on the comparison in (d); and (f) outputting (e.g., displaying) the conclusion in (e).

Embodiment 7. A computer program product comprising a computer-usable medium comprising:
(1) a computer program for receiving, storing, and/or retrieving a subject's genotype data for a plurality of genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the test loci listed in Table 1, and/or for one or more of such test locus a locus in linkage disequilibrium with one or more thereof; and (2) one or more computer programs for performing any one, all, or any combination of the following functions: (a) a computer program for querying the subject's genotype data; (b) calculating the subject's risk for developing cancer based at least on the subject's genotype data; (c) calculating a test score based on or derived from the subject's genotype data; (d) comparing the test score to one or more reference scores; (e) concluding whether there is an increased risk of cancer based at least in part on the comparison in (d); and (f) outputting (e.g., displaying) the conclusion in (e).

Embodiment 8. The method of Embodiment 2 or 4, wherein determining in (2) comprises determining (or estimating) the subject's percent probability of developing cancer within one or more specific periods of time.

Embodiment 9. The method of Embodiment 8, wherein the periods of time are chosen from the next five years; a plurality of five-, ten-, 15-, or 20-year intervals; the remainder of the subject's expected lifetime; or any time before a specific age (e.g., 50, 55, 60, 65, 70, 75, 80, 85, 90 years of age).

Embodiment 10. The method of any one of Embodiments 2, 4, 8, or 9, wherein determining in (2) comprises determining the subject's risk for developing cancer attributable or allocable to the genotypes detected in (1).

Embodiment 11. The method of Embodiment 10, wherein determining in (2) comprises combining the subject's risk for developing cancer attributable or allocable to the genotypes detected in (1) with other risk factors or calculations to yield a composite risk score or estimation.

Embodiment 12. The method of Embodiment 3, further comprising determining (or estimating) the subject's percent probability of developing cancer within one or more specific periods of time.

Embodiment 13. The method of Embodiment 12, wherein the periods of time are chosen from the next five years; a plurality of five-, ten-, 15-, or 20-year intervals; the remainder of the subject's expected lifetime; or any time before a specific age (e.g., 50, 55, 60, 65, 70, 75, 80, 85, 90 years of age).

Embodiment 14. The method of any one of Embodiments 3, 12, or 13, further comprising determining the subject's risk for developing cancer attributable or allocable to the genotypes detected in (1).

Embodiment 15. The method of Embodiment 14, further comprising combining the subject's risk for developing cancer attributable or allocable to the genotypes detected in (1) with other risk factors or calculations to yield a composite risk score or estimation.

Embodiment 16. The system of Embodiment 6 or the computer program product of Embodiment 7, further comprising a computer program for determining (or estimating) the subject's percent probability of developing cancer within one or more specific periods of time.

Embodiment 17. The system or computer program product of Embodiment 16, wherein the periods of time are chosen from the next five years; a plurality of five-, ten-, 15-, or 20-year intervals; the remainder of the subject's expected lifetime; or any time before a specific age (e.g., 50, 55, 60, 65, 70, 75, 80, 85, 90 years of age).

Embodiment 18. The system or computer program product of any one of Embodiments 6, 7, 16, or 17, further comprising a computer program for determining the subject's risk for developing cancer attributable or allocable to the genotypes detected in (1).

Embodiment 19. The system or computer program product of any one of Embodiments 6, 7, 16, 17, or 18, further comprising combining the subject's risk for developing cancer attributable or allocable to the genotypes detected in (1) with other risk factors or calculations to yield a composite risk score or estimation.

Embodiment 20. The method, system, or computer program product of any one of Embodiments 1 to 19, wherein the sample comprises germline genomic DNA of the subject or DNA derived therefrom.

Embodiment 21. The method, system, or computer program product of any one of Embodiments 1 to 19, wherein the subject does not or has been determined to not harbor a pathogenic or likely pathogenic variant in any cancer predisposition gene and the risk determined is the subject's residual risk of developing cancer.

Embodiment 22. The method, system, or computer program product of any one of Embodiments 1 to 19, wherein the subject does not or has been determined to not harbor a pathogenic or likely pathogenic variant in any gene or panel of genes listed in any of Tables 3A, 3B, 3C, or 3D.

Embodiment 23. A method for genotyping a subject comprising:

(1) analyzing a first sample of DNA obtained or derived from the subject to detect the sequence for a plurality of test genes comprising at least 2, 3, 4, 5, 6, 7, 8, 9, 10, 11, 12, 13, 14, 15, 16, 17, 18, 19, 20, 25, 30, 35, 40, 45, 50, 55, 60, or more genes or any panel of genes listed in any of Tables 3A, 3B, 3C, or 3D; and (2) analyzing either the first sample or a second sample of DNA obtained or derived from the subject to detect the genotype for a plurality of genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test locus a locus in linkage disequilibrium with one or more thereof.

Embodiment 24. A method for assessing risk for developing cancer comprising:

(1) analyzing a first sample of DNA obtained or derived from the subject to detect the sequence for a plurality of test genes comprising at least 2, 3, 4, 5, 6, 7, 8, 9, 10, 11, 12, 13, 14, 15, 16, 17, 18, 19, 20, 25, 30, 35, 40, 45, 50, 55, 60, or more genes or any panel of genes listed in any of Tables 3A, 3B, 3C, or 3D;

(2) analyzing either the first sample or a second sample of DNA obtained or derived from the subject to detect the genotype for a plurality of genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test locus a locus in linkage disequilibrium with one or more thereof; and (3) determining (or estimating) the subject's risk for developing cancer based at least in part on the genotypes detected in (2).

Embodiment 25. A method for assessing risk for developing cancer comprising:

(1) analyzing a first sample of DNA obtained or derived from the subject to detect the sequence for a plurality of test genes comprising at least 2, 3, 4, 5, 6, 7, 8, 9, 10, 11, 12, 13, 14, 15, 16, 17, 18, 19, 20, 25, 30, 35, 40, 45, 50, 55, 60, or more genes or any panel of genes listed in any of Tables 3A, 3B, 3C, or 3D;

(2) analyzing either the first sample or a second sample of DNA obtained or derived from the subject to detect the genotype for a plurality of genomic loci, wherein the plurality consists of at most X loci and comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more test loci listed in Table 1, and/or for one or more of such test locus a locus in linkage disequilibrium with one or more thereof;

(3) calculating a test score incorporating (or derived from) the genotypes detected in (2); and (4)(a) diagnosing a subject for whom the score in (3) exceeds a reference score as having a test likelihood of developing cancer that is higher than a reference likelihood of developing cancer; or (4)(b) diagnosing a subject for whom the score in (3) does not exceed a reference score as having a test likelihood of developing cancer that is equal to or lower than a reference likelihood of developing cancer.

Embodiment 26. A method for treating a subject comprising:

(1) determining whether a subject harbors any pathogenic or likely pathogenic variant in any of a plurality of test genes comprising at least 2, 3, 4, 5, 6, 7, 8, 9, 10, 11, 12, 13, 14, 15, 16, 17, 18, 19, 20, 25, 30, 35, 40, 45, 50, 55, 60, or more genes or any panel of genes listed in any of Tables 3A, 3B, 3C, or 3D;

(2) determining the subject's genotype for a plurality of genomic loci comprising at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or more of the test loci listed in Table 1, and/or for one or more of such test locus a locus in linkage disequilibrium with one or more thereof;

(3) determining (or estimating) the subject's risk for developing cancer based at least in part on the genotypes determined in (2); and (4) prescribing or administering one or more treatment modalities indicated based at least in part on the risk determined (or estimated) in (3).

Embodiment 27. The method of any one of Embodiments 23 to 26, wherein step (2) and any following step or steps is or are performed only in the case where no pathogenic or likely pathogenic variant is detected in step (1).

Embodiment 28. The method of any one of Embodiments 3, 12, 13, 14, or 15, wherein the test score is calculated according to an equation of the following general formula: $\Sigma_{(weighted\ genotype\ value\ for\ each\ test\ locus)}$, where weighted genotype value for each test locus=(Coefficient)*((Genotype Value)−(Mean Allele Copy Value)).

Embodiment 29. The method of any one of Embodiments 3, 12, 13, 14, or 15, wherein the test score is calculated according to Formula (I) or Formula (II).

EXAMPLES

Example 1

BACKGROUND

Women who are unaffected with cancer but have a significant family history of breast cancer are frequently referred for hereditary cancer testing with multi-gene panels. Despite being at high familial risk for development of breast cancer, fewer than 10% of such patients carry a clinically actionable mutation. Large-scale genotyping studies have identified common variants (primarily single-nucleotide polymorphisms, SNPs) that individually confer modest breast cancer risk, but together may explain the genetic susceptibility for breast cancer in many women without monogenic mutations. Here, we describe the development and validation of a polygenic residual risk score (RRS) in a large, consecutive cohort of women who tested negative for mutations in known breast cancer susceptibility genes.

Methods

Cohort

A consecutive series of women of European descent who had genetic testing with a multi-gene hereditary cancer risk panel was assessed. Clinical information was obtained from provider-completed test request forms and is summarized in Table A. Only women of European descent were included. The cohort was divided into a training (July-November 2016, N=11,771) and validation set (November 2016-March 2017, N=17,205).

TABLE A

| | Training Set | | Validation Set | |
|---|---|---|---|---|
| | All Patients (%) | BC Cases (%) | All Patients (%) | BC Cases (%) |
| Total Patients | 11,771 (100) | 2,089 (18) | 17,205 (100) | 2,917 (17) |
| | Age at Hereditary Cancer Testing | | | |
| Range | 18-84 | 22-84 | 18-84 | 22-84 |
| Median | 46 | 54 | 47 | 54 |
| % ≤50 | 61 | 7 | 61 | 7 |
| | Ancestry | | | |
| Western/Northern European | 8,744 (74) | 1,661 (80) | 12,722 (74) | 2,349 (81) |
| Central/Eastern European | 2,728 (23) | 385 (18) | 4,008 (23) | 509 (17) |
| Ashkenazi | 299 (3) | 43 (2) | 475 (3) | 59 (2) |
| | Cancer History in FDRs | | | |
| No BC or OC | 6,367 (54) | 1,349 (65) | 9,507 (55) | 1,919 (66) |
| ≥1 BC | 4,262 (36) | 642 (31) | 6,111 (36) | 892 (31) |
| ≥1 OC | 1,491 (13) | 132 (6) | 2,042 (12) | 160 (5) |
| ≥2 BC | 785 (7) | 143 (7) | 1,141 (7) | 193 (7) |
| ≥2 OC | 51 (<1) | 6 (<1) | 75 (<1) | 6 (<1) |
| ≥1 BC and ≥1 OC | 349 (3) | 34 (2) | 455 (3) | 54 (2) |

Next Generation Sequencing

A screening panel of 94 test loci and 3 loci in linkage disequilibrium with these loci was designed for the RainDance Thunderstorm NGS target enrichment system. Variant calls were obtained by NGS of amplicons on an Illumina HiSeq 2500 next generation sequencer to an average sequence depth of >1200x. Two of the polymorphic loci failed due to their location within repetitive elements and were discarded. Genotyping calls for non-failed 95 variants were validated using Sanger sequencing or the IonTorrent Ampliseq platform in 189 DNA samples. There was 100% concordance between the genotype calls generated using the RainDance Thunderstorm system and the comparator assays.

Statistical Analysis

Multivariable logistic regression models were used to evaluate the variants, develop a RRS as a predictor of personal breast cancer history in the training cohort, and assess the performance of the RRS in the validation cohort. Independent variables included age, personal/family cancer history, and ancestry (West/Northern European, Central/Eastern European, or Ashkenazi). Analysis of the validation cohort was conducted according to a pre-specified Statistical Analysis Plan.

RRS Development

Development Methods

SNP genotypes were coded as the number of the effect alleles (0, 1, or 2) (FIG. 1). The corresponding estimated coefficients were combined with log odds ratios (ORs) from the literature using weighted averaging with the weights inversely proportional to the squares of the corresponding confidence intervals. The resulting coefficients Bi were used to calculate SNP informativeness defined as $2f_i(1-f_i)\beta_i^2$, where $\beta_i$ is the effect allele frequency for $SNP_i$. To select the optimal number of variants in the final RRS, variants were ordered by informativeness. From 3 groups of linked SNPs in CCND1, ESR1 and TERT, we included only the most informative SNP from each group. Polygenic scores were constructed for cumulatively increasing numbers of variants and were evaluated with log likelihood ratios from logistic regression models.

Development Results

The maximum of the likelihood ratios was achieved with the 82 most informative SNPs (FIG. 2; Panel 4). The final RRS score was defined as $RRS=\Sigma\beta_i n_i$ Sum over the 82 most informative SNPs $n_i$ is the number of the effect alleles for $SNP_i$ $\beta_i$ is the coefficient estimated by combining results from the logistic regression model with 82 SNPs in the training cohort with published estimates as described above for 92 variants.

RRS Validation

Validation Results

RRS was strongly associated with personal history of breast cancer in the validation cohort (p<10-50). OR per unit standard deviation of the RRS of 1.42 (95% CI=1.36-1.49). This OR is lower than that of a published polygenic risk score (PRS) based on 77 SNPs (OR 1.55). This difference can be explained by the fact that OR for RRS was adjusted for family cancer history while the published OR for PRS was not.

Figure 3:
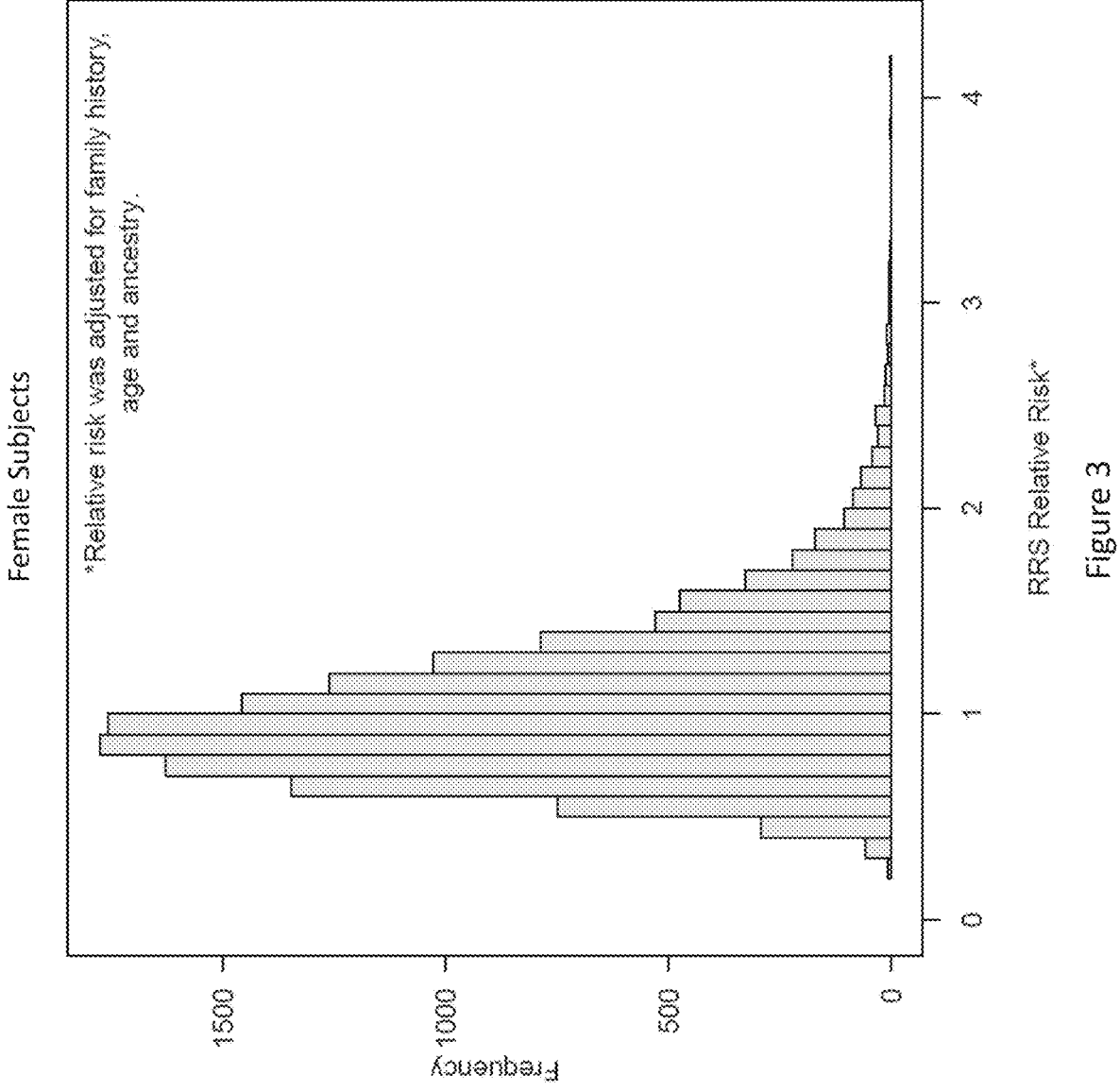
FIG. 3 shows the distribution of odds ratios associated with RRS (test score) in unaffected women from the validation cohort.

In a model with both scores included, the RRS score was significantly associated with breast cancer (p=3×10-5) while the PRS was not (p=0.2). FIG. 3 shows the distribution of odds ratios associated with RRS in unaffected women from the validation cohort.

CONCLUSIONS

A residual risk score was developed that is highly predictive of risk of development of future breast cancer in unaffected women with significant family history after testing negative for known high and intermediate risk mutations. The residual risk score significantly outperforms published polygenic risk score in this population of women due to the inclusion of a larger number of SNPs and the most informative SNPs as well as the refined OR estimates for individual SNPs. The clinical testing implementation of a residual risk score in women at risk for hereditary breast cancer may offer significant potential for the management of greater than 90% of high-risk women who test negative for monogenic breast cancer mutations.

Example 2

Methods

Residual Risk Score (RRS) and Combined RRS (cRRS)

Figure 6:
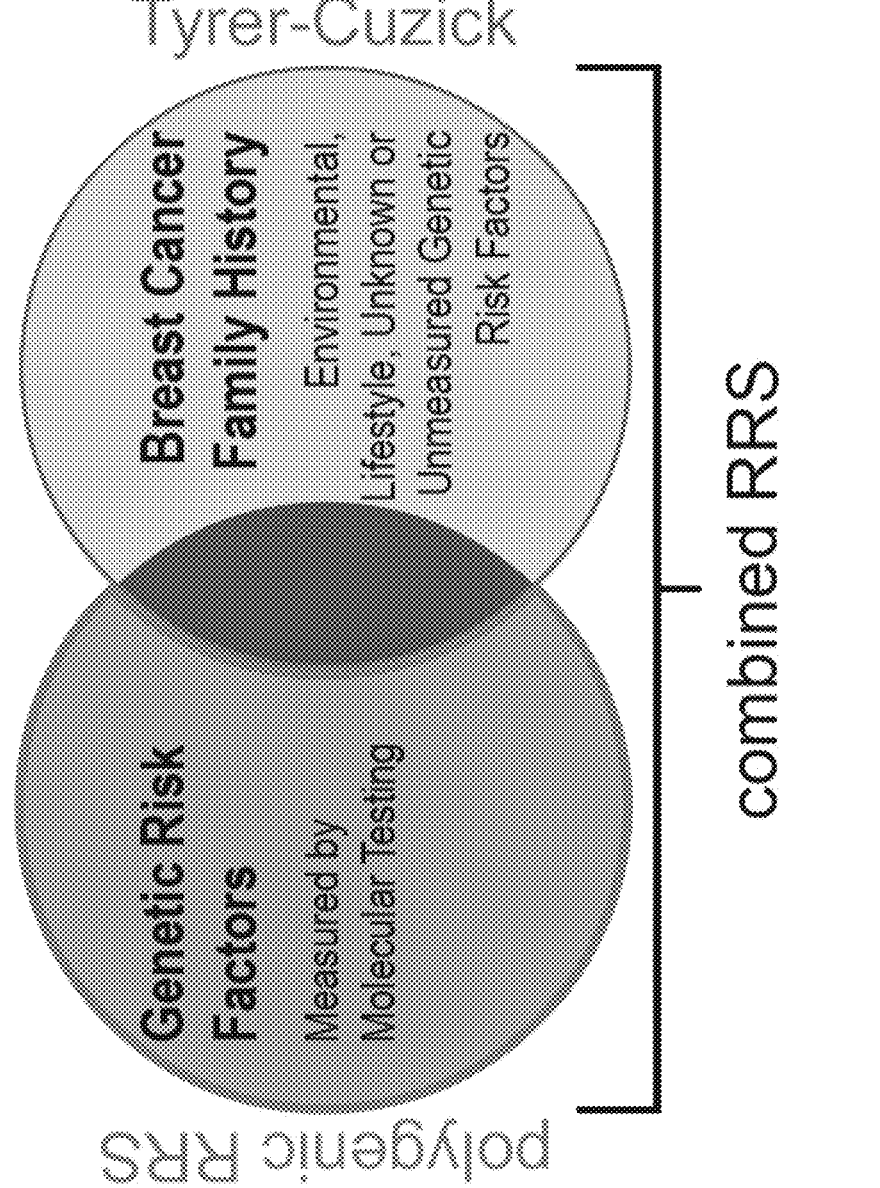
FIG. 6 is a diagram illustrating, conceptually, the combination of genetic and clinical factors into a combined residual risk score.

A polygenic RRS was developed and corrected for family history to determine breast cancer risk conferred by common genetic variants (see, e.g., Mavaddat et al. *J Natl Cancer Inst.* 2015; 107:djv036; Michalidou et al. *Nat Genet.* 2013; 45:353; Michailidou et al. *Nat Genet.* 2015; 47:373) independent of family history risk factors (FIG. 6). The cRRS was developed to account for genetic and family history risk factors by combining the RRS with the Tyrer-Cuzick model (Tyrer et al. *Stat Med.* 2004; 23:1111-30) (FIG. 6).

Cohorts

All patients had genetic testing for hereditary cancer risk and clinical information was obtained from provider-completed test request forms. Independent RRS training (N=24, 259) and validation (N=10,575) cohorts were composed of women of European descent who had multi-gene panel testing and were negative for mutations in breast cancer risk genes (BRCA1, BRCA2, TP53, PTEN, STK11, CDH1, PALB2, CHEK2, ATM, NBN, BARD1). The cRRS was validated in a case-control cohort (N=1,617). Breast cancer cases had a first diagnosis of pathologically confirmed ductal invasive breast cancer within 1 year of multi-gene panel testing. Unaffected controls had genetic testing for hereditary non-polyposis colon cancer (HNPCC) and no cancer history of any type. The cRRS and Tyrer-Cuzick models were also evaluated in a large clinical cohort of unaffected individuals who had multi-gene panel testing between June 2017 and July 2017 (N=6,479).

RRS Development and Validation

TABLE B

| | RRS Training and Validation Cohorts | | | |
|---|---|---|---|---|
| | RRS Development Set | | RRS Validation Set | |
| | All Patients (%) | BC Cases (%) | All Patients (%) | BC Cases (%) |
| Total Patients | 24,259 (100) | 4,291 (18) | 10,575 (100) | 1,627 (15) |
| | Age at Hereditary Cancer Testing | | | |
| Range | 18-84 | 22-84 | 18-84 | 25-84 |
| Median | 47 | 54 | 46 | 54 |
| % ≤50 | 61 | 7 | 63 | 6 |
| | Ancestry | | | |
| Western/Northern European | 18,079 (75) | 3,443 (80) | 7,717 (73) | 1,283 (79) |
| Central/Eastern European | 5,533 (23) | 762 (18) | 2,548 (24) | 310 (19) |
| Ashkenazi | 647 (3) | 86 (2) | 309 (3) | 34 (2) |
| | Cancer History in FDRs | | | |
| No BC or OC | 13,230 (55) | 2,800 (65) | 5,889 (56) | 1,044 (64) |
| ≥1 BC | 8,725 (36) | 1,315 (31) | 3,722 (35) | 524 (32) |
| ≥1 OC | 2,978 (12) | 251 (6) | 1,247 (12) | 80 (5) |
| ≥2 BC | 1,626 (7) | 293 (7) | 701 (7) | 106 (7) |
| ≥2 OC | 104 (<1) | 11 (<1) | 45 (<1) | 5 (<1) |
| ≥1 BC and ≥1 OC | 674 (3) | 75 (2) | 283 (3) | 21 (1) |

Figure 7:
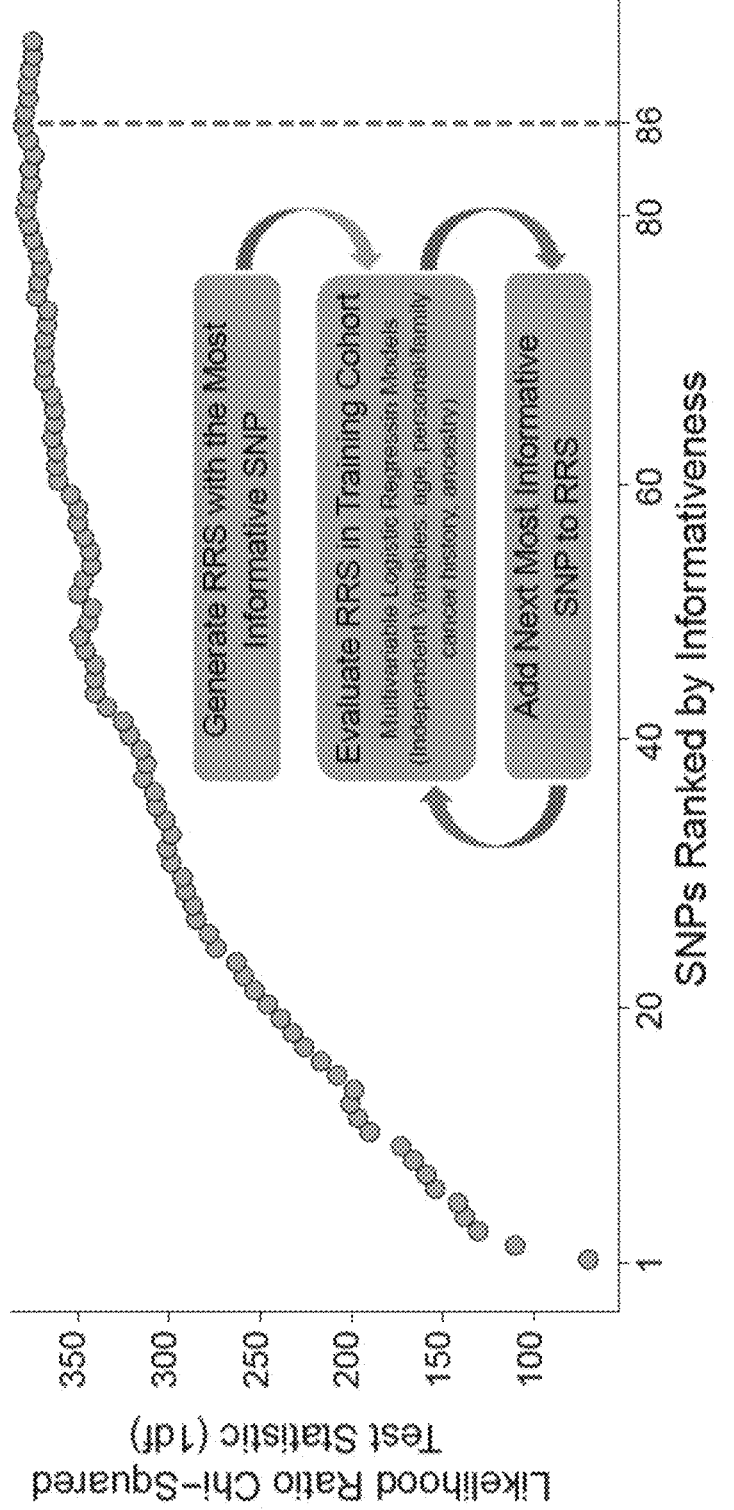
FIG. 7 is a diagram illustrating the process of determining (e.g., selecting SNPs for inclusion in) one optimal panel of SNPs (Panel 3) useful in various embodiments of this disclosure.

Abbreviations: FDR, First-degree relative; BC, Invasive ductal breast cancer; OC, Invasive epithelial ovarian cancer Genotypes were determined with Next Generation Sequencing and validated with Sanger sequencing for 97 variants and single-nucleotide polymorphisms (SNPs) with reported associations with breast cancer risk. (See, e.g., Mavaddat et al. *J Natl Cancer Inst.* 2015; 107:djv036; Michalidou et al. *Nat Genet.* 2013; 45:353; Michailidou et al. *Nat Genet.* 2015; 47:373) SNP genotypes were coded as the number of the effect alleles (0, 1, or 2). SNP coefficients (Bi) were estimated using weighted averaging of log odds ratios from the training cohort and published studies. (Id.) Weights were inversely proportional to squares of confidence intervals. SNP "informativeness" was defined as $2f_i(1-f_i)\beta_i^2$, where fi is the effect allele frequency for $SNP_i$. It was determined that the 86 most informative SNPs (the SNPs in Panel 3) provided the optimal RRS (FIG. 7). The RRS was strongly associated with personal history of breast cancer in the validation cohort (p<10-31). Odds Ratio per unit standard deviation of the RRS: 1.41 (95% CI=1.33-1.49).

cRRS Validation

TABLE C

| | cRRS Validation Cohort | | |
|---|---|---|---|
| | All Patients (%) | BC Cases (%) | Unaffected Controls (%) |
| Total Patients | (1,617) (100) | 990 (61) | 627 (39) |
| Age at Hereditary Cancer Testing | | | |
| Range | 18-84 | 18-84 | 18-73 |
| Median | 48 | 50 | 44 |
| % ≤ 50 | 57 | 52 | 67 |
| Ancestry | | | |
| Ashkenazi Jewish | 14 (1) | 4 (0) | 10 (2) |
| White/Non-Hispanic | 1,583 (98) | 977 (99) | 606 (97) |
| Ashkenazi Jewish and White/Non-Hispanic | 20 (1) | 9 (1) | 11 (2) |
| Family Cancer History | | | |
| One or More FDR with BC | 361 (22) | 302 (31) | 59 (9) |

FDR = First-degree relative; BC = Ductal invasive breast cancer.

TABLE D

| Association with Breast Cancer | | |
|---|---|---|
| BC Risk Prediction Model | Odds Ratio* (95% CI) | P-Value |
| Univariate Analysis | | |
| CRRS Remaining Lifetime Risk | 2.10 (1.85, 2.38) | $4.1 \times 10-35$ |
| Tyrer-Cuzick Remaining Lifetime Risk | 1.85 (1.63, 2.09) | $5.4 \times 10-24$ |
| CRRS 5-Year Risk | 4.64 (3.61, 5.95) | $5.2 \times 10-39$ |
| Tyrer-Cuzick 5-Year Risk | 5.14 (3.78, 6.99) | $3.5 \times 10-28$ |
| Multivariate Analysis | | |
| CRRS Remaining Lifetime Risk | 2.00 (1.64, 2.43) | $8.3 \times 10-13$ |
| CRRS 5-Year Risk | 3.91 (2.66, 5.75) | $1.0 \times 10-12$ |

*Odds ratios and Wald Confidence Interval (CIs) are reported per standard deviation of the log odds of BC risk prediction models in unaffected controls. Log odds of CRRS remaining lifetime risk had SD 0.61; CRRS 5-year risk had SD 1.12.

Figure 8:
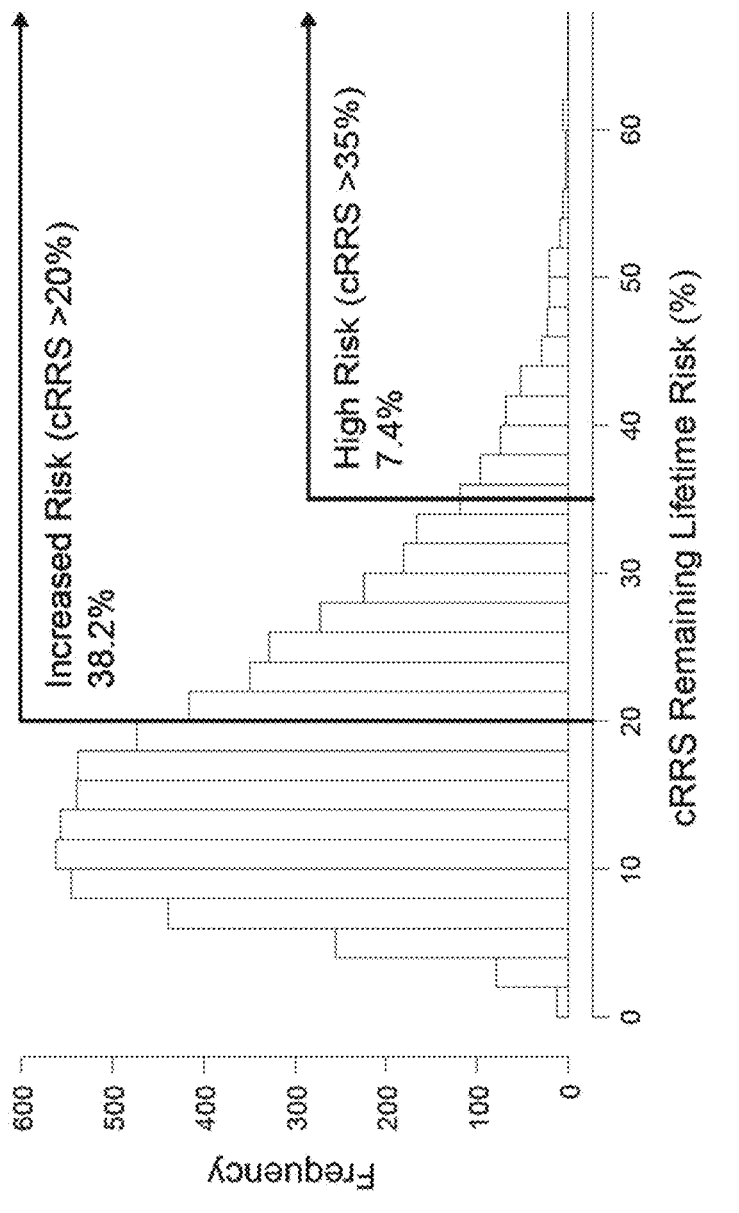
FIG. 8 is a histogram illustrating the cRRS remaining lifetime risk estimate range in Example 2 (from 0.88% to 66.4%), with 38.2% of patients having a lifetime risk >20% and 7.4% having a lifetime risk >35%. Such patients (i.e., with risk >20%) meet general guidelines, and are thus candidates, for increased screening for breast cancer (e.g., early and/or annual mammograms and/or breast MRI).

The remaining lifetime and 5-year breast cancer risk estimates determined by cRRS and Tyrer-Cuzick were highly significant (Table D). cRRS (RRS+Tyrer-Cuzick) was more strongly associated with breast cancer than Tyrer-Cuzick alone. cRRS added significant breast cancer risk discrimination independent of that captured by Tyrer-Cuzick for both remaining lifetime risk (p=8.3×10-13) and 5-year risk (p=1.0×10-12) (Table D). Mean cRRS and Tyrer-Cuzick breast cancer risk estimates among unaffected controls were concordant, indicating that the cRRS was properly calibrated. The cRRS remaining lifetime risk estimates ranged from 0.88% to 66.4% in the clinical testing cohort (FIG. 8). 38.2% of patients had a lifetime risk >20% and 7.4% had a lifetime risk >35%. Such patients (i.e., with risk >20%) meet general guidelines, and are thus candidates, for increased screening for breast cancer (e.g., early and/or annual mammograms and/or breast MRI).

CONCLUSIONS

A residual risk score was developed and is highly predictive of risk of development of future breast cancer in unaffected women with significant family history after testing negative for known high and intermediate risk mutations. When the genetic risk from the residual risk score was combined with the Tyrer-Cuzick model, the resulting cRRS was a superior predictor of breast cancer risk compared to Tyrer-Cuzick alone. The clinical testing implementation of a combined residual risk score in women at risk for hereditary breast cancer may offer significant potential for the management of greater than 90% of high-risk women who test negative for monogenic mutations in breast cancer susceptibility genes.

All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing disclosure has been described in some detail by way of illustration and example for purposes of clarity of understanding, it will be clear that certain changes and modifications may be practiced within the scope of the appended claims.

What is claimed is:

1. A method for assessing risk for developing breast cancer comprising:
(1) obtaining genomic DNA (gDNA) from a blood, saliva, or fibroblast sample from a subject;
(2) sequencing, via targeted next generation sequencing, the gDNA to detect both the subject's genotype for a plurality of test genomic loci comprising at least 90 or more test genomic loci and a locus in linkage disequilibrium with one or more of said test genomic loci, and wherein the test genomic loci are selected from:

| SNP Designation | SNP Designation | SNP Designation | SNP Designation |
|---|---|---|---|
| Panel 1 | | | |
| chr17:29230520:D | rs12662670 | rs2236007 | rs6507583 |
| rs10069690 | rs12710696 | rs2363956 | rs6678914 |
| rs1011970 | rs1292011 | rs2380205 | rs6762644 |
| rs1045485 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11075995 | rs1353747 | rs3817198 | rs745570 |
| rs11199914 | rs1432679 | rs3903072 | rs75915166 |
| rs11242675 | rs1436904 | rs4245739 | rs7707921 |
| rs11249433 | rs1550623 | rs4593472 | rs7726159 |
| rs11552449 | rs16857609 | rs4808801 | rs78540526 |
| rs11571833 | rs17356907 | rs4849887 | rs7904519 |
| rs11621587 | rs17529111 | rs4973768 | rs8170 |
| rs11627032 | rs17817449 | rs527616 | rs865686 |
| rs11780156 | rs17879961 | rs554219 | rs889312 |
| rs11814448 | rs186951 | rs6001930 | rs9257408 |
| rs11820646 | rs2012709 | rs616488 | rs941764 |
| rs12048493 | rs2016394 | rs62070644 | rs9693444 |
| rs12405132 | rs204247 | rs6472903 | rs9790517 |
| rs12422552 | rs2046210 | rs6504950 | rs999737 |
| rs12493607 | | | |
| Panel 2 | | | |
| rs10069690 | rs12710696 | rs2363956 | rs6507583 |
| rs1011970 | rs1292011 | rs2380205 | rs6678914 |
| rs1045485 | rs13162653 | rs2588809 | rs6762644 |
| rs10472076 | rs132390 | rs2736108 | rs6796502 |
| rs1053338 | rs13267382 | rs2823093 | rs6828523 |
| rs10759243 | rs13281615 | rs2943559 | rs6964587 |
| rs10771399 | rs13329835 | rs2981579 | rs704010 |
| rs10941679 | rs13365225 | rs3760982 | rs7072776 |
| rs10995190 | rs13387042 | rs3803662 | rs720475 |

-continued

-continued

| SNP Designation | SNP Designation | SNP Designation | SNP Designation |
|---|---|---|---|
| rs11075995 | rs1353747 | rs3817198 | rs72755295 |
| rs11199914 | rs1432679 | rs3903072 | rs745570 |
| rs11242675 | rs1436904 | rs4245739 | rs75915166 |
| rs11249433 | rs1550623 | rs4593472 | rs7707921 |
| rs11552449 | rs16857609 | rs4808801 | rs7726159 |
| rs11571833 | rs17356907 | rs4849887 | rs78540526 |
| rs11627032 | rs17529111 | rs4973768 | rs7904519 |
| rs11780156 | rs17817449 | rs527616 | rs8170 |
| rs11814448 | rs17879961 | rs554219 | rs865686 |
| rs11820646 | rs2012709 | rs6001930 | rs889312 |
| rs12405132 | rs2016394 | rs616488 | rs941764 |
| rs12422552 | rs204247 | rs62070644 | rs9693444 |
| rs12493607 | rs2046210 | rs6472903 | rs9790517 |
| rs12662670 | rs2236007 | rs6504950 | rs999737 |

Panel 3

| SNP Designation | SNP Designation | SNP Designation | SNP Designation |
|---|---|---|---|
| rs10069690 | rs13162653 | rs2588809 | rs6796502 |
| rs1011970 | rs132390 | rs2736108 | rs6828523 |
| rs10472076 | rs13267382 | rs2823093 | rs6964587 |
| rs1053338 | rs13281615 | rs2943559 | rs704010 |
| rs10759243 | rs13329835 | rs2981579 | rs7072776 |
| rs10771399 | rs13365225 | rs3760982 | rs720475 |
| rs10941679 | rs13387042 | rs3803662 | rs72755295 |
| rs10995190 | rs1353747 | rs3817198 | rs745570 |
| rs11199914 | rs1432679 | rs3903072 | rs75915166 |
| rs11242675 | rs1436904 | rs4593472 | rs7707921 |
| rs11249433 | rs1550623 | rs4808801 | rs7726159 |
| rs11552449 | rs16857609 | rs4849887 | rs78540526 |
| rs11571833 | rs17356907 | rs4973768 | rs7904519 |
| rs11627032 | rs17529111 | rs527616 | rs8170 |
| rs11780156 | rs17817449 | rs554219 | rs865686 |
| rs11814448 | rs17879961 | rs6001930 | rs889312 |
| rs11820646 | rs2012709 | rs616488 | rs941764 |
| rs12405132 | rs2016394 | rs62070644 | rs9693444 |
| rs12493607 | rs204247 | rs6472903 | rs9790517 |
| rs12662670 | rs2046210 | rs6504950 | rs999737 |
| rs12710696 | rs2236007 | rs6507583 | |
| rs1292011 | rs2363956 | rs6762644 | |

Panel 4

| SNP Designation | SNP Designation | SNP Designation | SNP Designation |
|---|---|---|---|
| rs10069690 | rs1292011 | rs2236007 | rs6762644 |
| rs1011970 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11199914 | rs1353747 | rs3817198 | rs745570 |
| rs11242675 | rs1432679 | rs3903072 | rs75915166 |

| SNP Designation | SNP Designation | SNP Designation | SNP Designation |
|---|---|---|---|
| rs11249433 | rs1436904 | rs4593472 | rs7707921 |
| rs11552449 | rs1550623 | rs4808801 | rs7726159 |
| rs11571833 | rs16857609 | rs4849887 | rs78540526 |
| rs11627032 | rs17356907 | rs4973768 | rs7904519 |
| rs11780156 | rs17529111 | rs527616 | rs865686 |
| rs11814448 | rs17817449 | rs554219 | rs889312 |
| rs11820646 | rs17879961 | rs6001930 | rs941764 |
| rs12048493 | rs2012709 | rs616488 | rs9693444 |
| rs12405132 | rs2016394 | rs6472903 | rs999737 |
| rs12493607 | rs204247 | rs6504950 | |
| rs12662670 | rs2046210 | rs6507583 | | and (3) determining or estimating the subject's risk for developing breast cancer based at least in part on the genotypes detected in (2), and a test score derived from the genotypes detected in (2), wherein calculating the test score comprises calculating, using a computer program, the following general formula: $\Sigma_{(weighted\ genotype\ value\ for\ each\ test\ locus)}$, where the weighted genotype value for each test locus=(Coefficient)*((Genotype Value)−(Mean Allele Copy Value)).

2. The method for assessing risk for developing breast cancer of claim 1, further comprising (4)(a) diagnosing a subject for whom the score in (3) exceeds a reference score as having a test likelihood of developing breast cancer that is higher than a reference likelihood of developing breast cancer, or (4)(b) diagnosing a subject for whom the score in (3) does not exceed a reference score as having a test likelihood of developing breast cancer that is equal to or lower than a reference likelihood of developing breast cancer.

3. The method of claim 2, further comprising determining or estimating the subject's percent probability of developing breast cancer within one or more specific periods of time.

4. The method of claim 3, wherein the periods of time are chosen from the next five years; a plurality of five-, ten-, 15-, or 20-year intervals; the remainder of the subject's expected lifetime; or any time before a specific age selected from 50, 55, 60, 65, 70, 75, 80, 85, or 90 years of age.

5. The method of claim 1, wherein the subject does not or has been determined to not harbor a pathogenic or likely pathogenic variant in one or more genes or panel of genes selected from:

| Gene # | Panel B | Panel C | Panel D | Panel E | Panel F | Panel G |
|---|---|---|---|---|---|---|
| 1 | BRCA1 | BRCA1 | BRCA1 | MLH1 | BRCA1 | BRCA1 |
| 2 | BRCA2 | BRCA2 | BRCA2 | MSH2 | BRCA2 | BRCA2 |
| 3 | MLH1 | MLH1 | CHEK2 | MSH6 | MLH1 | MLH1 |
| 4 | MSH2 | MSH2 | ATM | PMS2 | MSH2 | MSH2 |
| 5 | MSH6 | MSH6 | NBN | BRCA1 | MSH6 | MSH6 |
| 6 | PMS2 | PMS2 | PALB2 | BRCA2 | PMS2 | PMS2 |
| 7 | EPCAM | EPCAM | BARD1 | ATM | EPCAM | EPCAM |
| 8 | MUTYH | MUTYH | BRIP1 | BARD1 | APC | APC |
| 9 | APC | APC | PMS2 | BRIP1 | MUTYH | MUTYH |
| 10 | CDKN2A | CDKN2A | MSH2 | CHEK2 | PALB2 | PALB2 |
| 11 | PALB2 | PALB2 | MSH6 | MUTYH | CDKN2A | CHEK2 |
| 12 | SMAD4 | SMAD4 | TP53 | RAD50 | CDK4 | PTEN |
| 13 | BMPR1A | BMPR1A | MUTYH | EPCAM | TP53 | STK11 |
| 14 | TP53 | TP53 | | | PTEN | CDH1 |
| 15 | PTEN | PTEN | | | CDH1 | TP53 |
| 16 | STK11 | STK11 | | | STK11 | ATM |
| 17 | CDH1 | CDH1 | | | SMAD4 | RAD51C |
| 18 | NBN1 | NBN1 | | | BMPR1A | RAD51D |
| 19 | CHEK2 | CHEK2 | | | ATM | BRIP1 |
| 20 | RAD51C | RAD51C | | | CHEK2 | BARD1 |

-continued

| | | | | |
|---|---|---|---|---|
| 21 | RAD51D | RAD51D | RAD51C | BMPR1A |
| 22 | BRIP1 | BRIP1 | RAD51D | SMAD4 |
| 23 | BARD1 | BARD1 | MLH3 | CDKN2A |
| 24 | ATM | ATM | BRIP1 | CDK4 |
| 25 | CDK4 | CDK4 | BARD1 | RAD50 |
| 26 | | RAD50 | NSB1 | NBN |
| 27 | | MRE11A | RAD50 | MRE11 |
| 28 | | MLH3 | MRE11A | MLH3 |
| 29 | | MITF | HOXB13 | |
| 30 | | ELAC2 | | |

| Gene # | Panel H | Panel I | Panel J | Panel K | Panel L | Panel M | Panel N |
|---|---|---|---|---|---|---|---|
| 1 | APC | ATM | APC | BLM | ATR | BRCA1 | BRCA1 |
| 2 | BRCA1 | BMPR1A | ATM | CEBPA | BARD1 | BRCA2 | BRCA2 |
| 3 | BRCA2 | CDH1 | BMPR1A | FLCN | BRAF | MLH1 | MLH1 |
| 4 | CDKN2A | CDK4 | BRCA1 | MEN1 | BRIP1 | MSH2 | MSH2 |
| 5 | EPCAM | CHEK2 | BRCA2 | PTCH | FANCA | MSH6 | MSH6 |
| 6 | MLH1 | HOXB13 | CDH1 | RET | FANCB | PMS2 | PMS2 |
| 7 | MSH2 | TP53 | CDK4 | SDHAF2 | FANCC | EPCAM | EPCAM |
| 8 | MSH6 | PTEN | CDKN2A | SDHB | FANCD2 | MUTYH | MUTYH |
| 9 | MUTYH | SMAD4 | CHEK2 | SDHC | FANCE | APC | APC |
| 10 | PALB2 | STK11 | EPCAM | SDHD | FANCF | CDKN2A | CDKN2A |
| 11 | PMS2 | | MLH1 | TMEM127 | FANCG | PALB2 | PALB2 |
| 12 | | | MSH2 | VHL | FANCI | SMAD4 | SMAD4 |
| 13 | | | MSH6 | | FANCL | BMPR1A | BMPR1A |
| 14 | | | MUTYH | | FANCM | TP53 | TP53 |
| 15 | | | TP53 | | KRAS | PTEN | PTEN |
| 16 | | | PALB2 | | MLH3 | STK11 | STK11 |
| 17 | | | PMS2 | | MRE11 | CDH1 | CDH1 |
| 18 | | | PTEN | | NBS1 | NBN1 | NBN1 |
| 19 | | | SMAD4 | | PIK3CA | CHEK2 | CHEK2 |
| 20 | | | STK11 | | PMS1 | RAD51C | RAD51C |
| 21 | | | | | RAD50 | RAD51D | RAD51D |
| 22 | | | | | RAD51C | BRIP1 | BRIP1 |
| 23 | | | | | | BARD1 | BARD1 |
| 24 | | | | | | ATM | ATM |
| 25 | | | | | | CDK4 | CDK4 |
| 26 | | | | | | | MITF |
| 27 | | | | | | | ELAC2 |

| Gene # | Gene Symbol | Gene # | Gene Symbol | Gene # | Gene Symbol |
|---|---|---|---|---|---|
| 1 | BRCA1 | 24 | PALB2 | 47 | RAD50 |
| 2 | BRCA2 | 25 | TP53 | 48 | MRE11 |
| 3 | MLH1 | 26 | FANCL | 49 | BRIP1 |
| 4 | MSH2 | 27 | BLM | 50 | FLCN |
| 5 | PMS2 | 28 | CDK4 | 51 | TMEM127 |
| 6 | MLH3 | 29 | CDKN2A | 52 | PIK3CA |
| 7 | EPCAM | 30 | ATM | 53 | KRAS |
| 8 | MSH6 | 31 | PTCH1 | 54 | BRAF |
| 9 | APC | 32 | CHEK2 | 55 | HOXB13 |
| 10 | PMS1 | 33 | RAD51C | 56 | ATR |
| 11 | PTEN | 34 | CEBPA | 57 | BAP1 |
| 12 | STK11 | 35 | NBS1 | 58 | CFTR |
| 13 | RET | 36 | FANCA | 59 | CTRC |
| 14 | SDHD | 37 | FANCC | 60 | FGFR2 |
| 15 | SDHC | 38 | FANCD2 | 61 | FH |
| 16 | SDHB | 39 | FANCE | 62 | HRAS |
| 17 | SDHAF2 | 40 | FANCG | 63 | KITLG |
| 18 | CDH1 | 41 | FANCI | 64 | NF1 |
| 19 | MUTYH | 42 | FANCM | 65 | NF2 |
| 20 | SMAD4 | 43 | RAD51D | 66 | PRSS1 |
| 21 | MEN1 | 44 | FANCF | 67 | RB1 |
| 22 | VHL | 45 | FANCB | 68 | SPINK1 |
| 23 | BMPR1A | 46 | BARD1 | 69 | TGFB2 |

| Gene # | Gene Symbol | Gene # | Gene Symbol | Gene # | Gene Symbol |
|---|---|---|---|---|---|
| 1 | BRCA1 | 24 | VHL | 47 | NBS1 |
| 2 | BRCA2 | 25 | MEN1 | 48 | RAD50 |
| 3 | MLH1 | 26 | RET | 49 | FANCA |
| 4 | MSH2 | 27 | NF1 | 50 | FANCB |
| 5 | MSH6 | 28 | NF2 | 51 | FANCC |
| 6 | PMS2 | 29 | RB1 | 52 | FANCD2 |
| 7 | EPCAM | 30 | PTCH1 | 53 | FANCE |

-continued

| | | | | | |
|---|---|---|---|---|---|
| 8 | APC | 31 | FH | 54 | FANCF |
| 9 | MUTYH | 32 | BLM | 55 | FANCG |
| 10 | PALB2 | 33 | CEBPA | 56 | FANCI |
| 11 | CDKN2A | 34 | FLCN | 57 | FANCL |
| 12 | CDK4 | 35 | SDHB | 58 | FANCM |
| 13 | TP53 | 36 | SDHC | 59 | ATR |
| 14 | PTEN | 37 | SDHD | 60 | HRAS |
| 15 | CDH1 | 38 | SDHAF2 | 61 | TGFB2 |
| 16 | STK11 | 39 | TMEM127 | 62 | FGFR2 |
| 17 | SMAD4 | 40 | CFTR | 63 | BAP1 |
| 18 | BMPR1A | 41 | PRSS1 | 64 | KITLG |
| 19 | ATM | 42 | CTRC | 65 | BRAF |
| 20 | CHEK2 | 43 | SPINK1 | 66 | MRE11 |
| 21 | RAD51C | 44 | KRAS | 67 | PIK3CA |
| 22 | RAD51D | 45 | BRIP1 | 68 | PMS1 |
| 23 | MLH3 | 46 | BARD1 | 69 | HOXB13 |

6. The method of claim 5, wherein the plurality of test genes comprise: APC, ATM, BAP1, BARD1, BMPR1A, BRCA1, BRCA2, BRIP1, CDH1, CDK4, CDKN2A, CHEK2, EPCAM, FH, FLCN, HOXB13, MEN1, MITF, MLH1, MSH2, MSH6, MUTYH, PALB2, PMS2, PTEN, RAD51C, RAD51D, RET, SDHB, SDHC, SDHD, SMAD4, STK11, TP53, and VHL.

7. The method of claim 1, wherein determining in (3) comprises determining or estimating the subject's percent probability of developing breast cancer within one or more specific periods of time.

8. The method of claim 7, wherein the periods of time are chosen from the next five years; a plurality of five-, ten-, 15-, or 20-year intervals; the remainder of the subject's expected lifetime; or any time before a specific age selected from 50, 55, 60, 65, 70, 75, 80, 85, or 90 years of age.

9. The method of claim 1, wherein determining in (3) comprises determining the subject's risk for developing breast cancer attributable or allocable to the genotypes detected in (2) in combination with other risk factors or calculations to yield a composite risk score or estimation.

10. The method of claim 1, wherein the subject has a significant family history of breast cancer and tested negative for known high and intermediate risk mutations.

11. The method of claim 1, further comprising outputting the risk of the subject for developing breast cancer.

12. The method of claim 1, wherein the test genomic loci comprise: rs616488, rs11552449, rs11249433, rs12405132, rs6678914, rs4245739, rs72755295, rs12710696, rs4849887, rs2016394, rs1550623, rs1045485, rs13387042, rs16857609, rs6762644, rs4973768, rs12493607, rs6796502, rs1053338, rs9790517, rs6828523, rs10069690, rs7726159, rs2736108, rs13162653, rs2012709, rs10941679, rs889312, rs10472076, rs1353747, rs7707921, rs1432679, rs11242675, rs204247, rs17529111, rs12662670, rs2046210, rs6964587, rs4593472, rs720475, rs9693444, rs13365225, rs6472903, rs2943559, rs13267382, rs13281615, rs11780156, rs1011970, rs10759243, rs865686, rs2380205, rs7072776, rs11814448, rs10995190, rs704010, rs7904519, rs11199914, rs2981579, rs3817198, rs3903072, rs78540526, rs554219, rs75915166, rs11820646, rs12422552, rs10771399, rs17356907, rs1292011, rs11571833, rs2236007, rs2588809, rs999737, rs941764, rs11627032, rs3803662, rs17817449, rs11075995, rs13329835, rs6504950, rs745570, rs527616, rs1436904, rs6507583, rs8170, rs2363956, rs4808801, rs3760982, rs2823093, rs17879961, rs132390, and rs6001930.

13. A method for assessing risk for developing breast cancer comprising:

(1) obtaining genomic DNA (gDNA) from a blood, saliva, or fibroblast sample from a subject;

(2) sequencing, via next generation sequencing, the gDNA to detect the sequence for a plurality of test genes comprising at least 30 or more genes or any panel of genes selected from:

| Gene # | Panel B | Panel C | Panel D | Panel E | Panel F | Panel G |
|---|---|---|---|---|---|---|
| 1 | BRCA1 | BRCA1 | BRCA1 | MLH1 | BRCA1 | BRCA1 |
| 2 | BRCA2 | BRCA2 | BRCA2 | MSH2 | BRCA2 | BRCA2 |
| 3 | MLH1 | MLH1 | CHEK2 | MSH6 | MLH1 | MLH1 |
| 4 | MSH2 | MSH2 | ATM | PMS2 | MSH2 | MSH2 |
| 5 | MSH6 | MSH6 | NBN | BRCA1 | MSH6 | MSH6 |
| 6 | PMS2 | PMS2 | PALB2 | BRCA2 | PMS2 | PMS2 |
| 7 | EPCAM | EPCAM | BARD1 | ATM | EPCAM | EPCAM |
| 8 | MUTYH | MUTYH | BRIP1 | BARD1 | APC | APC |
| 9 | APC | APC | PMS2 | BRIP1 | MUTYH | MUTYH |
| 10 | CDKN2A | CDKN2A | MSH2 | CHEK2 | PALB2 | PALB2 |
| 11 | PALB2 | PALB2 | MSH6 | MUTYH | CDKN2A | CHEK2 |
| 12 | SMAD4 | SMAD4 | TP53 | RAD50 | CDK4 | PTEN |
| 13 | BMPR1A | BMPR1A | MUTYH | EPCAM | TP53 | STK11 |
| 14 | TP53 | TP53 | | | PTEN | CDH1 |
| 15 | PTEN | PTEN | | | CDH1 | TP53 |
| 16 | STK11 | STK11 | | | STK11 | ATM |
| 17 | CDH1 | CDH1 | | | SMAD4 | RAD51C |
| 18 | NBN1 | NBN1 | | | BMPR1A | RAD51D |
| 19 | CHEK2 | CHEK2 | | | ATM | BRIP1 |
| 20 | RAD51C | RAD51C | | | CHEK2 | BARD1 |
| 21 | RAD51D | RAD51D | | | RAD51C | BMPR1A |

-continued

| 22 | BRIP1 | BRIP1 | | | RAD51D | SMAD4 |
|----|-------|-------|--|--|--------|-------|
| 23 | BARD1 | BARD1 | | | MLH3 | CDKN2A |
| 24 | ATM | ATM | | | BRIP1 | CDK4 |
| 25 | CDK4 | CDK4 | | | BARD1 | RAD50 |
| 26 | | RAD50 | | | NSB1 | NBN |
| 27 | | MRE11A | | | RAD50 | MRE11 |
| 28 | | MLH3 | | | MRE11A | MLH3 |
| 29 | | MITF | | | HOXB13 | |
| 30 | | ELAC2 | | | | |

| Gene # | Panel H | Panel I | Panel J | Panel K | Panel L | Panel M | Panel N |
|--------|---------|---------|---------|---------|---------|---------|---------|
| 1 | APC | ATM | APC | BLM | ATR | BRCA1 | BRCA1 |
| 2 | BRCA1 | BMPR1A | ATM | CEBPA | BARD1 | BRCA2 | BRCA2 |
| 3 | BRCA2 | CDH1 | BMPR1A | FLCN | BRAF | MLH1 | MLH1 |
| 4 | CDKN2A | CDK4 | BRCA1 | MEN1 | BRIP1 | MSH2 | MSH2 |
| 5 | EPCAM | CHEK2 | BRCA2 | PTCH | FANCA | MSH6 | MSH6 |
| 6 | MLH1 | HOXB13 | CDH1 | RET | FANCB | PMS2 | PMS2 |
| 7 | MSH2 | TP53 | CDK4 | SDHAF2 | FANCC | EPCAM | EPCAM |
| 8 | MSH6 | PTEN | CDKN2A | SDHB | FANCD2 | MUTYH | MUTYH |
| 9 | MUTYH | SMAD4 | CHEK2 | SDHC | FANCE | APC | APC |
| 10 | PALB2 | STK11 | EPCAM | SDHD | FANCF | CDKN2A | CDKN2A |
| 11 | PMS2 | | MLH1 | TMEM127 | FANCG | PALB2 | PALB2 |
| 12 | | | MSH2 | VHL | FANCI | SMAD4 | SMAD4 |
| 13 | | | MSH6 | | FANCL | BMPR1A | BMPR1A |
| 14 | | | MUTYH | | FANCM | TP53 | TP53 |
| 15 | | | TP53 | | KRAS | PTEN | PTEN |
| 16 | | | PALB2 | | MLH3 | STK11 | STK11 |
| 17 | | | PMS2 | | MRE11 | CDH1 | CDH1 |
| 18 | | | PTEN | | NBS1 | NBN1 | NBN1 |
| 19 | | | SMAD4 | | PIK3CA | CHEK2 | CHEK2 |
| 20 | | | STK11 | | PMS1 | RAD51C | RAD51C |
| 21 | | | | | RAD50 | RAD51D | RAD51D |
| 22 | | | | | RAD51C | BRIP1 | BRIP1 |
| 23 | | | | | | BARD1 | BARD1 |
| 24 | | | | | | ATM | ATM |
| 25 | | | | | | CDK4 | CDK4 |
| 26 | | | | | | | MITF |
| 27 | | | | | | | ELAC2 |

| Gene # | Gene Symbol | Gene # | Gene Symbol | Gene # | Gene Symbol |
|--------|-------------|--------|-------------|--------|-------------|
| 1 | BRCA1 | 24 | PALB2 | 47 | RAD50 |
| 2 | BRCA2 | 25 | TP53 | 48 | MRE11 |
| 3 | MLH1 | 26 | FANCL | 49 | BRIP1 |
| 4 | MSH2 | 27 | BLM | 50 | FLCN |
| 5 | PMS2 | 28 | CDK4 | 51 | TMEM127 |
| 6 | MLH3 | 29 | CDKN2A | 52 | PIK3CA |
| 7 | EPCAM | 30 | ATM | 53 | KRAS |
| 8 | MSH6 | 31 | PTCH1 | 54 | BRAF |
| 9 | APC | 32 | CHEK2 | 55 | HOXB13 |
| 10 | PMS1 | 33 | RAD51C | 56 | ATR |
| 11 | PTEN | 34 | CEBPA | 57 | BAP1 |
| 12 | STK11 | 35 | NBS1 | 58 | CFTR |
| 13 | RET | 36 | FANCA | 59 | CTRC |
| 14 | SDHD | 37 | FANCC | 60 | FGFR2 |
| 15 | SDHC | 38 | FANCD2 | 61 | FH |
| 16 | SDHB | 39 | FANCE | 62 | HRAS |
| 17 | SDHAF2 | 40 | FANCG | 63 | KITLG |
| 18 | CDH1 | 41 | FANCI | 64 | NF1 |
| 19 | MUTYH | 42 | FANCM | 65 | NF2 |
| 20 | SMAD4 | 43 | RAD51D | 66 | PRSS1 |
| 21 | MEN1 | 44 | FANCF | 67 | RB1 |
| 22 | VHL | 45 | FANCB | 68 | SPINK1 |
| 23 | BMPR1A | 46 | BARD1 | 69 | TGFB2 |

| Gene # | Gene Symbol | Gene # | Gene Symbol | Gene # | Gene Symbol |
|--------|-------------|--------|-------------|--------|-------------|
| 1 | BRCA1 | 24 | VHL | 47 | NBS1 |
| 2 | BRCA2 | 25 | MEN1 | 48 | RAD50 |
| 3 | MLH1 | 26 | RET | 49 | FANCA |
| 4 | MSH2 | 27 | NF1 | 50 | FANCB |
| 5 | MSH6 | 28 | NF2 | 51 | FANCC |
| 6 | PMS2 | 29 | RB1 | 52 | FANCD2 |
| 7 | EPCAM | 30 | PTCH1 | 53 | FANCE |
| 8 | APC | 31 | FH | 54 | FANCF |

-continued

| 9 | MUTYH | 32 | BLM | 55 | FANCG |
|---|---|---|---|---|---|
| 10 | PALB2 | 33 | CEBPA | 56 | FANCI |
| 11 | CDKN2A | 34 | FLCN | 57 | FANCL |
| 12 | CDK4 | 35 | SDHB | 58 | FANCM |
| 13 | TP53 | 36 | SDHC | 59 | ATR |
| 14 | PTEN | 37 | SDHD | 60 | HRAS |
| 15 | CDH1 | 38 | SDHAF2 | 61 | TGFB2 |
| 16 | STK11 | 39 | TMEM127 | 62 | FGFR2 |
| 17 | SMAD4 | 40 | CFTR | 63 | BAP1 |
| 18 | BMPR1A | 41 | PRSS1 | 64 | KITLG |
| 19 | ATM | 42 | CTRC | 65 | BRAF |
| 20 | CHEK2 | 43 | SPINK1 | 66 | MRE11 |
| 21 | RAD51C | 44 | KRAS | 67 | PIK3CA |
| 22 | RAD51D | 45 | BRIP1 | 68 | PMS1 |
| 23 | MLH3 | 46 | BARD1 | 69 | HOXB13 |

(3) targeted next generation sequencing either the gDNA or a gDNA obtained or derived from a second blood, saliva, or fibroblast sample from the subject and genotyping (i) a plurality of test genomic loci comprising at least 90 or more test genomic loci wherein the test genomic loci comprise a Single Nucleotide Polymorphism (SNP), and (ii) one or more loci in linkage disequilibrium with a SNP, wherein the test genomic loci are selected from:

| SNP Designation | SNP Designation | SNP Designation | SNP Designation |
|---|---|---|---|
| | Panel 1 | | |
| chr17:29230520:D | rs12662670 | rs2236007 | rs6507583 |
| rs10069690 | rs12710696 | rs2363956 | rs6678914 |
| rs1011970 | rs1292011 | rs2380205 | rs6762644 |
| rs1045485 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11075995 | rs1353747 | rs3817198 | rs745570 |
| rs11199914 | rs1432679 | rs3903072 | rs75915166 |
| rs11242675 | rs1436904 | rs4245739 | rs7707921 |
| rs11249433 | rs1550623 | rs4593472 | rs7726159 |
| rs11552449 | rs16857609 | rs4808801 | rs78540526 |
| rs11571833 | rs17356907 | rs4849887 | rs7904519 |
| rs11621587 | rs17529111 | rs4973768 | rs8170 |
| rs11627032 | rs17817449 | rs527616 | rs865686 |
| rs11780156 | rs17879961 | rs554219 | rs889312 |
| rs11814448 | rs186951 | rs6001930 | rs9257408 |
| rs11820646 | rs2012709 | rs616488 | rs941764 |
| rs12048493 | rs2016394 | rs62070644 | rs9693444 |
| rs12405132 | rs204247 | rs6472903 | rs9790517 |
| rs12422552 | rs2046210 | rs6504950 | rs999737 |
| rs12493607 | | | |
| | Panel 2 | | |
| rs10069690 | rs12710696 | rs2363956 | rs6507583 |
| rs1011970 | rs1292011 | rs2380205 | rs6678914 |
| rs1045485 | rs13162653 | rs2588809 | rs6762644 |
| rs10472076 | rs132390 | rs2736108 | rs6796502 |
| rs1053338 | rs13267382 | rs2823093 | rs6828523 |
| rs10759243 | rs13281615 | rs2943559 | rs6964587 |
| rs10771399 | rs13329835 | rs2981579 | rs704010 |
| rs10941679 | rs13365225 | rs3760982 | rs7072776 |
| rs10995190 | rs13387042 | rs3803662 | rs720475 |
| rs11075995 | rs1353747 | rs3817198 | rs72755295 |
| rs11199914 | rs1432679 | rs3903072 | rs745570 |
| rs11242675 | rs1436904 | rs4245739 | rs75915166 |
| rs11249433 | rs1550623 | rs4593472 | rs7707921 |
| rs11552449 | rs16857609 | rs4808801 | rs7726159 |
| rs11571833 | rs17356907 | rs4849887 | rs78540526 |
| rs11627032 | rs17529111 | rs4973768 | rs7904519 |

-continued

| SNP Designation | SNP Designation | SNP Designation | SNP Designation |
|---|---|---|---|
| rs11780156 | rs17817449 | rs527616 | rs8170 |
| rs11814448 | rs17879961 | rs554219 | rs865686 |
| rs11820646 | rs2012709 | rs6001930 | rs889312 |
| rs12405132 | rs2016394 | rs616488 | rs941764 |
| rs12422552 | rs204247 | rs62070644 | rs9693444 |
| rs12493607 | rs2046210 | rs6472903 | rs9790517 |
| rs12662670 | rs2236007 | rs6504950 | rs999737 |
| | Panel 3 | | |
| rs10069690 | rs13162653 | rs2588809 | rs6796502 |
| rs1011970 | rs132390 | rs2736108 | rs6828523 |
| rs10472076 | rs13267382 | rs2823093 | rs6964587 |
| rs1053338 | rs13281615 | rs2943559 | rs704010 |
| rs10759243 | rs13329835 | rs2981579 | rs7072776 |
| rs10771399 | rs13365225 | rs3760982 | rs720475 |
| rs10941679 | rs13387042 | rs3803662 | rs72755295 |
| rs10995190 | rs1353747 | rs3817198 | rs745570 |
| rs11199914 | rs1432679 | rs3903072 | rs75915166 |
| rs11242675 | rs1436904 | rs4593472 | rs7707921 |
| rs11249433 | rs1550623 | rs4808801 | rs7726159 |
| rs11552449 | rs16857609 | rs4849887 | rs78540526 |
| rs11571833 | rs17356907 | rs4973768 | rs7904519 |
| rs11627032 | rs17529111 | rs527616 | rs8170 |
| rs11780156 | rs17817449 | rs554219 | rs865686 |
| rs11814448 | rs17879961 | rs6001930 | rs889312 |
| rs11820646 | rs2012709 | rs616488 | rs941764 |
| rs12405132 | rs2016394 | rs62070644 | rs9693444 |
| rs12493607 | rs204247 | rs6472903 | rs9790517 |
| rs12662670 | rs2046210 | rs6504950 | rs999737 |
| rs12710696 | rs2236007 | rs6507583 | |
| rs1292011 | rs2363956 | rs6762644 | |
| | Panel 4 | | |
| rs10069690 | rs1292011 | rs2236007 | rs6762644 |
| rs1011970 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11199914 | rs1353747 | rs3817198 | rs745570 |
| rs11242675 | rs1432679 | rs3903072 | rs75915166 |
| rs11249433 | rs1436904 | rs4593472 | rs7707921 |
| rs11552449 | rs1550623 | rs4808801 | rs7726159 |
| rs11571833 | rs16857609 | rs4849887 | rs78540526 |
| rs11627032 | rs17356907 | rs4973768 | rs7904519 |
| rs11780156 | rs17529111 | rs527616 | rs865686 |
| rs11814448 | rs17817449 | rs554219 | rs889312 |
| rs11820646 | rs17879961 | rs6001930 | rs941764 |
| rs12048493 | rs2012709 | rs616488 | rs9693444 |
| rs12405132 | rs2016394 | rs6472903 | rs999737 |
| rs12493607 | rs204247 | rs6504950 | |
| rs12662670 | rs2046210 | rs6507583 | |

(4) calculating a test score incorporating or derived from the genotypes detected in (3), wherein calculating the test score comprises calculating, using a computer program, the following general formula: $\Sigma_{(weighted\ genotype\ value\ for\ each\ test\ locus)}$, where the weighted genotype value for each test locus=(Coefficient)*((Genotype Value)−(Mean Allele Copy Value)); and (5)(a) diagnosing a subject for whom the score in (4) exceeds a reference score as having a test likelihood of developing breast cancer that is higher than a reference likelihood of developing breast cancer, or (5)(b) diagnosing a subject for whom the score in (4) does not exceed a reference score as having a test likelihood of developing breast cancer that is equal to or lower than a reference likelihood of developing breast cancer.

14. The method of claim 13, further comprising determining or estimating the subject's percent probability of developing breast cancer within one or more specific periods of time.

15. The method of claim 14, wherein the periods of time are chosen from the next five years; a plurality of five-, ten-, 15-, or 20-year intervals; the remainder of the subject's expected lifetime; or any time before a specific age selected from 50, 55, 60, 65, 70, 75, 80, 85, or 90 years of age.

16. The method of claim 14, wherein the percent probability of developing breast cancer is calculated according to Formula (I): Test score=1−(1−[Clinical Score])$^{exp(C1*[Test\ Score])}$, or Formula (II): Test score=1−(1−[Clinical Score])$^{(exp(C1*[Test\ Score]+C2))}$.

17. The method of claim 13, further comprising determining the subject's risk for developing breast cancer attributable or allocable to the genotypes detected in (3) in combination with other risk factors or calculations to yield a composite risk score or estimation.

18. The method of claim 13, further comprising outputting the risk of the subject for developing breast cancer.

19. The method of claim 13, wherein the test genomic loci comprise: rs616488, rs11552449, rs11249433, rs12405132, rs6678914, rs4245739, rs72755295, rs12710696, rs4849887, rs2016394, rs1550623, rs1045485, rs13387042, rs16857609, rs6762644, rs4973768, rs12493607, rs6796502, rs1053338, rs9790517, rs6828523, rs10069690, rs7726159, rs2736108, rs13162653, rs2012709, rs10941679, rs889312, rs10472076, rs1353747, rs7707921, rs1432679, rs11242675, rs204247, rs17529111, rs12662670, rs2046210, rs6964587, rs4593472, rs720475, rs9693444, rs13365225, rs6472903, rs2943559, rs13267382, rs13281615, rs11780156, rs1011970, rs10759243, rs865686, rs2380205, rs7072776, rs11814448, rs10995190, rs704010, rs7904519, rs11199914, rs2981579, rs3817198, rs3903072, rs78540526, rs554219, rs75915166, rs11820646, rs12422552, rs10771399, rs17356907, rs1292011, rs11571833, rs2236007, rs2588809, rs999737, rs941764, rs11627032, rs3803662, rs17817449, rs11075995, rs13329835, rs6504950, rs745570, rs527616, rs1436904, rs6507583, rs8170, rs2363956, rs4808801, rs3760982, rs2823093, rs17879961, rs132390, and rs6001930.

20. The method of claim 13, wherein the plurality of test genes comprise: APC, ATM, BAP1, BARD1, BMPR1A, BRCA1, BRCA2, BRIP1, CDH1, CDK4, CDKN2A, CHEK2, EPCAM, FH, FLCN, HOXB13, MEN1, MITF, MLH1, MSH2, MSH6, MUTYH, PALB2, PMS2, PTEN, RAD51C, RAD51D, RET, SDHB, SDHC, SDHD, SMAD4, STK11, TP53, and VHL.

21. A method of calculating a test score comprising:

(1) targeted next generation sequencing genomic DNA (gDNA) obtained or derived from a blood, saliva, or fibroblast sample from a subject to detect both the subject's genotype for a plurality of test genomic loci comprising at least 90 or more test genomic loci and a locus in linkage disequilibrium with one or more of said test genomic loci, and wherein the test genomic loci are selected from:

| SNP Designation | SNP Designation | SNP Designation | SNP Designation |
|---|---|---|---|
| Panel 1 | | | |
| chr17:29230520:D | rs12662670 | rs2236007 | rs6507583 |
| rs10069690 | rs12710696 | rs2363956 | rs6678914 |
| rs1011970 | rs1292011 | rs2380205 | rs6762644 |
| rs1045485 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11075995 | rs1353747 | rs3817198 | rs745570 |
| rs11199914 | rs1432679 | rs3903072 | rs75915166 |
| rs11242675 | rs1436904 | rs4245739 | rs7707921 |
| rs11249433 | rs1550623 | rs4593472 | rs7726159 |
| rs11552449 | rs16857609 | rs4808801 | rs78540526 |
| rs11571833 | rs17356907 | rs4849887 | rs7904519 |
| rs11621587 | rs17529111 | rs4973768 | rs8170 |
| rs11627032 | rs17817449 | rs527616 | rs865686 |
| rs11780156 | rs17879961 | rs554219 | rs889312 |
| rs11814448 | rs186951 | rs6001930 | rs9257408 |
| rs11820646 | rs2012709 | rs616488 | rs941764 |
| rs12048493 | rs2016394 | rs62070644 | rs9693444 |
| rs12405132 | rs204247 | rs6472903 | rs9790517 |
| rs12422552 | rs2046210 | rs6504950 | rs999737 |
| rs12493607 | | | |
| Panel 2 | | | |
| rs10069690 | rs12710696 | rs2363956 | rs6507583 |
| rs1011970 | rs1292011 | rs2380205 | rs6678914 |
| rs1045485 | rs13162653 | rs2588809 | rs6762644 |
| rs10472076 | rs132390 | rs2736108 | rs6796502 |
| rs1053338 | rs13267382 | rs2823093 | rs6828523 |
| rs10759243 | rs13281615 | rs2943559 | rs6964587 |
| rs10771399 | rs13329835 | rs2981579 | rs704010 |
| rs10941679 | rs13365225 | rs3760982 | rs7072776 |
| rs10995190 | rs13387042 | rs3803662 | rs720475 |
| rs11075995 | rs1353747 | rs3817198 | rs72755295 |
| rs11199914 | rs1432679 | rs3903072 | rs745570 |
| rs11242675 | rs1436904 | rs4245739 | rs75915166 |
| rs11249433 | rs1550623 | rs4593472 | rs7707921 |
| rs11552449 | rs16857609 | rs4808801 | rs7726159 |
| rs11571833 | rs17356907 | rs4849887 | rs78540526 |
| rs11627032 | rs17529111 | rs4973768 | rs7904519 |
| rs11780156 | rs17817449 | rs527616 | rs8170 |
| rs11814448 | rs17879961 | rs554219 | rs865686 |
| rs11820646 | rs2012709 | rs6001930 | rs889312 |
| rs12405132 | rs2016394 | rs616488 | rs941764 |
| rs12422552 | rs204247 | rs62070644 | rs9693444 |
| rs12493607 | rs2046210 | rs6472903 | rs9790517 |
| rs12662670 | rs2236007 | rs6504950 | rs999737 |
| Panel 3 | | | |
| rs10069690 | rs13162653 | rs2588809 | rs6796502 |
| rs1011970 | rs132390 | rs2736108 | rs6828523 |
| rs10472076 | rs13267382 | rs2823093 | rs6964587 |
| rs1053338 | rs13281615 | rs2943559 | rs704010 |
| rs10759243 | rs13329835 | rs2981579 | rs7072776 |
| rs10771399 | rs13365225 | rs3760982 | rs720475 |
| rs10941679 | rs13387042 | rs3803662 | rs72755295 |
| rs10995190 | rs1353747 | rs3817198 | rs745570 |
| rs11199914 | rs1432679 | rs3903072 | rs75915166 |
| rs11242675 | rs1436904 | rs4593472 | rs7707921 |
| rs11249433 | rs1550623 | rs4808801 | rs7726159 |
| rs11552449 | rs16857609 | rs4849887 | rs78540526 |

-continued

| SNP Designation | SNP Designation | SNP Designation | SNP Designation |
|---|---|---|---|
| rs11571833 | rs17356907 | rs4973768 | rs7904519 |
| rs11627032 | rs17529111 | rs527616 | rs8170 |
| rs11780156 | rs17817449 | rs554219 | rs865686 |
| rs11814448 | rs17879961 | rs6001930 | rs889312 |
| rs11820646 | rs2012709 | rs616488 | rs941764 |
| rs12405132 | rs2016394 | rs62070644 | rs9693444 |
| rs12493607 | rs204247 | rs6472903 | rs9790517 |
| rs12662670 | rs2046210 | rs6504950 | rs999737 |
| rs12710696 | rs2236007 | rs6507583 | |
| rs1292011 | rs2363956 | rs6762644 | |
| Panel 4 | | | |
| rs10069690 | rs1292011 | rs2236007 | rs6762644 |
| rs1011970 | rs13162653 | rs2588809 | rs6796502 |
| rs10472076 | rs132390 | rs2736108 | rs6828523 |
| rs1053338 | rs13267382 | rs2823093 | rs6964587 |
| rs10759243 | rs13281615 | rs2943559 | rs704010 |
| rs10771399 | rs13329835 | rs2981579 | rs7072776 |
| rs10941679 | rs13365225 | rs3760982 | rs720475 |
| rs10995190 | rs13387042 | rs3803662 | rs72755295 |
| rs11199914 | rs1353747 | rs3817198 | rs745570 |
| rs11242675 | rs1432679 | rs3903072 | rs75915166 |
| rs11249433 | rs1436904 | rs4593472 | rs7707921 |
| rs11552449 | rs1550623 | rs4808801 | rs7726159 |
| rs11571833 | rs16857609 | rs4849887 | rs78540526 |
| rs11627032 | rs17356907 | rs4973768 | rs7904519 |
| rs11780156 | rs17529111 | rs527616 | rs865686 |
| rs11814448 | rs17817449 | rs554219 | rs889312 |
| rs11820646 | rs17879961 | rs6001930 | rs941764 |
| rs12048493 | rs2012709 | rs616488 | rs9693444 |
| rs12405132 | rs2016394 | rs6472903 | rs999737 |
| rs12493607 | rs204247 | rs6504950 | |
| rs12662670 | rs2046210 | rs6507583 | |

(2) determining or estimating the subject's risk for developing breast cancer based at least in part on the genotypes detected in (1), and a test score derived from the genotypes detected in (1), wherein calculating the test score comprises calculating, using a computer program, the following general formula: $\Sigma_{(weighted\ genotype\ value\ for\ each\ test\ locus)}$, where weighted genotype value for each test locus=(Coefficient)* ((Genotype Value)−(Mean Allele Copy Value)).

22. The method of claim 21, further comprising outputting the risk of the subject for developing breast cancer.

23. The method of claim 21, wherein the test genomic loci comprise: rs616488, rs11552449, rs11249433, rs12405132, rs6678914, rs4245739, rs72755295, rs12710696, rs4849887, rs2016394, rs1550623, rs1045485, rs13387042, rs16857609, rs6762644, rs4973768, rs12493607, rs6796502, rs1053338, rs9790517, rs6828523, rs10069690, rs7726159, rs2736108, rs13162653, rs2012709, rs10941679, rs889312, rs10472076, rs1353747, rs7707921, rs1432679, rs11242675, rs204247, rs17529111, rs12662670, rs2046210, rs6964587, rs4593472, rs720475, rs9693444, rs13365225, rs6472903, rs2943559, rs13267382, rs13281615, rs11780156, rs1011970, rs10759243, rs865686, rs2380205, rs7072776, rs11814448, rs10995190, rs704010, rs7904519, rs11199914, rs2981579, rs3817198, rs3903072, rs78540526, rs554219, rs75915166, rs11820646, rs12422552, rs10771399, rs17356907, rs1292011, rs11571833, rs2236007, rs2588809, rs999737, rs941764, rs11627032, rs3803662, rs17817449, rs11075995, rs13329835, rs6504950, rs745570, rs527616, rs1436904, rs6507583, rs8170, rs2363956, rs4808801, rs3760982, rs2823093, rs17879961, rs132390, and rs6001930.

24. A method for assessing risk for developing breast cancer of a subject comprising:
(1) obtaining genomic DNA (gDNA) obtained or derived from a blood, saliva, or fibroblast sample from a subject;
(2) sequencing, via next generation sequencing, the gDNA to detect the sequence for a plurality of test genes comprising at least 30 or more genes, wherein the plurality of test genes comprise: APC, ATM, BAP1, BARD1, BMPR1A, BRCA1, BRCA2, BRIP1, CDH1, CDK4, CDKN2A, CHEK2, EPCAM, FH, FLCN, HOXB13, MEN1, MITF, MLH1, MSH2, MSH6, MUTYH, PALB2, PMS2, PTEN, RAD51C, RAD51D, RET, SDHB, SDHC, SDHD, SMAD4, STK11, TP53, and VHL;
(3) targeted next generation sequencing either the gDNA or gDNA obtained or derived from a second blood, saliva, or fibroblast sample from the subject and genotyping (i) a plurality of test genomic loci comprising at least 90 or more test genomic loci wherein the test genomic loci comprise a SNP, and (ii) one or more loci in linkage disequilibrium with a SNP, wherein the test genomic loci comprise: rs616488, rs11552449, rs11249433, rs12405132, rs6678914, rs4245739, rs72755295, rs12710696, rs4849887, rs2016394, rs1550623, rs1045485, rs13387042, rs16857609, rs6762644, rs4973768, rs12493607, rs6796502, rs1053338, rs9790517, rs6828523, rs10069690, rs7726159, rs2736108, rs13162653, rs2012709, rs10941679, rs889312, rs10472076, rs1353747, rs7707921, rs1432679, rs11242675, rs204247, rs17529111, rs12662670, rs2046210, rs6964587, rs4593472, rs720475, rs9693444, rs13365225, rs6472903, rs2943559, rs13267382, rs13281615, rs11780156, rs1011970, rs10759243, rs865686, rs2380205, rs7072776, rs11814448, rs10995190, rs704010, rs7904519, rs11199914, rs2981579, rs3817198, rs3903072, rs78540526, rs554219, rs75915166, rs11820646, rs12422552, rs10771399, rs17356907, rs1292011, rs11571833, rs2236007, rs2588809, rs999737, rs941764, rs11627032, rs3803662, rs17817449, rs11075995, rs13329835, rs6504950, rs745570, rs527616, rs1436904, rs6507583, rs8170, rs2363956, rs4808801, rs3760982, rs2823093, rs17879961, rs132390, and rs6001930;
(4) calculating a test score incorporating or derived from the genotypes detected in (3), wherein calculating the test score comprises calculating, using the a computer program, the following general formula: $\Sigma_{(weighted\ genotype\ value\ for\ each\ test\ locus)}$, where the weighted genotype value for each test locus=(Coefficient)*((Genotype Value)−(Mean Allele Copy Value)); and
(5)(a) diagnosing a subject for whom the score in (4) exceeds a reference score as having a test likelihood of developing breast cancer that is higher than a reference likelihood of developing breast cancer; or
(5)(b) diagnosing a subject for whom the score in (4) does not exceed a reference score as having a test likelihood of developing breast cancer that is equal to or lower than a reference likelihood of developing breast cancer.

25. A method for genotyping a subject determined to have a risk for developing breast cancer, comprising:
(1) sequencing a gDNA from a blood, saliva, or fibroblast sample from the subject for a plurality of test genes comprising 30-50 genes, wherein the plurality of test genes comprises: APC, ATM, BAP1, BARD1, BMPR1A, BRCA1, BRCA2, BRIP1, CDH1, CDK4, CDKN2A, CHEK2, EPCAM, FH, FLCN, HOXB13, MEN1, MITF, MLH1, MSH2, MSH6, MUTYH, PALB2, PMS2, PTEN, RAD51C, RAD51D, RET, SDHB, SDHC, SDHD, SMAD4, STK11, TP53, and VHL; and (2) targeted sequencing either the gDNA or gDNA from a second blood, saliva, or fibroblast sample from the subject and genotyping (i) a plurality of test genomic loci comprising 90-150 test genomic loci, wherein the test genomic loci comprise a SNP or (ii) one or more loci in linkage disequilibrium with the test genomic loci, wherein the test genomic loci comprise: rs616488, rs11552449, rs11249433, rs12405132, rs6678914, rs4245739, rs72755295, rs12710696, rs4849887, rs2016394, rs1550623, rs1045485, rs13387042, rs16857609, rs6762644, rs4973768, rs12493607, rs6796502, rs1053338, rs9790517, rs6828523, rs10069690, rs7726159, rs2736108, rs13162653, rs2012709, rs10941679, rs889312, rs10472076, rs1353747, rs7707921, rs1432679, rs11242675, rs204247, rs17529111, rs12662670, rs2046210, rs6964587, rs4593472, rs720475, rs9693444, rs13365225, rs6472903, rs2943559, rs13267382, rs13281615, rs11780156, rs1011970, rs10759243, rs865686, rs2380205, rs7072776, rs11814448, rs10995190, rs704010, rs7904519, rs11199914, rs2981579, rs3817198, rs3903072, rs78540526, rs554219, rs75915166, rs11820646, rs12422552, rs10771399, rs17356907, rs1292011, rs11571833, rs2236007, rs2588809, rs999737, rs941764, rs11627032, rs3803662, rs17817449, rs11075995, rs13329835, rs6504950, rs745570, rs527616, rs1436904, rs6507583, rs8170, rs2363956, rs4808801, rs3760982, rs2823093, rs17879961, rs132390, and rs6001930;

thereby providing a genotype for each of the test genes and test genomic loci.

26. A method of sequencing genomic DNA (gDNA) from a sample, comprising:

(1) sequencing a gDNA from a blood, saliva, or fibroblast sample for a plurality of test genes comprising 30-50 genes, wherein the plurality of test genes comprises: APC, ATM, BAP1, BARD1, BMPR1A, BRCA1, BRCA2, BRIP1, CDH1, CDK4, CDKN2A, CHEK2, EPCAM, FH, FLCN, HOXB13, MEN1, MITF, MLH1, MSH2, MSH6, MUTYH, PALB2, PMS2, PTEN, RAD51C, RAD51D, RET, SDHB, SDHC, SDHD, SMAD4, STK11, TP53, and VHL; and (2) targeted sequencing the gDNA for (i) a plurality of test genomic loci comprising 90-150 test genomic loci, wherein the test genomic loci comprise a SNP or (ii) one or more loci in linkage disequilibrium with the test genomic loci, wherein the test genomic loci comprise: rs616488, rs11552449, rs11249433, rs12405132, rs6678914, rs4245739, rs72755295, rs12710696, rs4849887, rs2016394, rs1550623, rs1045485, rs13387042, rs16857609, rs6762644, rs4973768, rs12493607, rs6796502, rs1053338, rs9790517, rs6828523, rs10069690, rs7726159, rs2736108, rs13162653, rs2012709, rs10941679, rs889312, rs10472076, rs1353747, rs7707921, rs1432679, rs11242675, rs204247, rs17529111, rs12662670, rs2046210, rs6964587, rs4593472, rs720475, rs9693444, rs13365225, rs6472903, rs2943559, rs13267382, rs13281615, rs11780156, rs1011970, rs10759243, rs865686, rs2380205, rs7072776, rs11814448, rs10995190, rs704010, rs7904519, rs11199914, rs2981579, rs3817198, rs3903072, rs78540526, rs554219, rs75915166, rs11820646, rs12422552, rs10771399, rs17356907, rs1292011, rs11571833, rs2236007, rs2588809, rs999737, rs941764, rs11627032, rs3803662, rs17817449, rs11075995, rs13329835, rs6504950, rs745570, rs527616, rs1436904, rs6507583, rs8170, rs2363956, rs4808801, rs3760982, rs2823093, rs17879961, rs132390, and rs6001930;

wherein blood, saliva, or fibroblast sample is obtained from a subject suspected to be at risk of developing breast cancer.

* * * * *